US011539506B2

(12) United States Patent
Lee et al.

(10) Patent No.: US 11,539,506 B2
(45) Date of Patent: *Dec. 27, 2022

(54) SYSTEM AND METHOD FOR HEALTHCARE SECURITY AND INTEROPERABILITY

(71) Applicant: Janssen Pharmaceutica NV, Beerse (BE)

(72) Inventors: Jessica Lee, Edison, NJ (US); Jun Morimura, Tokyo (JP); Michael Moschetti, Montville, NJ (US); John Vig, Irvine, CA (US); Marvin Quesada, Princeton, NJ (US)

(73) Assignee: Janssen Pharmaceutica NV, Beerse (BE)

( * ) Notice: Subject to any disclaimer, the term of this patent is extended or adjusted under 35 U.S.C. 154(b) by 169 days.

This patent is subject to a terminal disclaimer.

(21) Appl. No.: 17/149,703

(22) Filed: Jan. 14, 2021

(65) Prior Publication Data

US 2021/0135841 A1 May 6, 2021

Related U.S. Application Data

(63) Continuation-in-part of application No. 16/703,848, filed on Dec. 4, 2019, now Pat. No. 10,931,437.
(Continued)

(51) Int. Cl.
*H04L 9/06* (2006.01)
*G16H 15/00* (2018.01)
(Continued)

(52) U.S. Cl.
CPC .......... *H04L 9/0618* (2013.01); *G16H 10/60* (2018.01); *G16H 15/00* (2018.01); *H04L 9/50* (2022.05)

(58) Field of Classification Search
CPC ..... H04L 9/0618; H04L 9/50; H04L 2209/42; H04L 2209/88; H04L 9/3239;
(Continued)

(56) References Cited

U.S. PATENT DOCUMENTS

2017/0091397 A1* 3/2017 Shah ................. H04L 63/20
2018/0198624 A1* 7/2018 Bisti ................. H04L 9/3239

* cited by examiner

*Primary Examiner* — Huan V Doan
(74) *Attorney, Agent, or Firm* — McDermott Will & Emery LLP

(57) ABSTRACT

Embodiments facilitate interoperability and secure determination of healthcare costs. An entity may receive a first Electronic Health Record (EHR) sub-block with patient medical coverage information and first treatments and may transmit a first Device Drug Information (DIR) sub-block comprising first treatment classes corresponding to each first treatment, first treatment class members corresponding to each first treatment class, and corresponding first treatment class member cost information. In response, the entity may receive a second EHR sub-block comprising second treatments each: associated with a corresponding first treatment, and selected from corresponding first treatment class members. Upon receipt of a transaction confirmation, the entity may augment a multi-dimensional blockchain with a multi-dimensional block formed by linking: a DIR block including second treatment information, an EHR block including information based on the second EHR sub-block and a transaction block. Payment assistance information determined from the second EHR block may be transmitted to a patient.

20 Claims, 15 Drawing Sheets

Related U.S. Application Data which is a continuation of application No. 16/251,980, filed on Jan. 18, 2019, now Pat. No. 10,541,807.

(51) Int. Cl.
*G16H 10/60* (2018.01)
*H04L 9/00* (2022.01)

(58) Field of Classification Search
CPC ...... G16H 10/60; G16H 15/00; G06F 21/602; G06F 21/64; G06F 21/6245
See application file for complete search history.

1000

START

1010
Obtain, from at least one encrypted first Health Transaction Record (HTR) sub-block decryptable by the first entity, a first set of first treatments for the patient over a time period, wherein each first treatment comprises a first diagnosis code and a first treatment code

1015
Obtain, based on the first set: (a) one or more second sets of second treatments, wherein each corresponding second treatment is associated with: a distinct first treatment in the first set, and (b) a corresponding number of recurrences for each second treatment

1020
Obtain a set of available insurance plans available to the patient and corresponding coverage related information for each available insurance plan

1025
Obtain, based on the set of second treatments and corresponding coverage related information for each insurance plan, corresponding estimated plan-specific cost metrics for the patient

1030
Transmit, a first encrypted Drug-Device Information Record (DIR) sub-block decryptable by at least one second entity, wherein the DIR sub-block comprises the plan-specific cost metrics for the patient

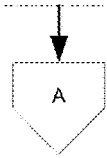

FIG. 10A

SYSTEM AND METHOD FOR HEALTHCARE SECURITY AND INTEROPERABILITY

CROSS REFERENCE TO RELATED APPLICATIONS

This application is a continuation-in-part of U.S. patent application Ser. No. 16/703,848 entitled "SYSTEM AND METHOD FOR HEALTHCARE SECURITY AND INTEROPERABILITY," filed Dec. 4, 2019, which is a continuation of U.S. patent application Ser. No. 16/251,980 entitled "SYSTEM AND METHOD FOR HEALTHCARE SECURITY AND INTEROPERABILITY," filed Jan. 18, 2019 (now U.S. Pat. No. 10,541,807). The above-identified applications are hereby incorporated by reference herein in their entireties.

FIELD

The subject matter disclosed herein relates to healthcare system security and interoperability, while facilitating treatment selection and transparency in cost determination.

BACKGROUND

Healthcare information systems face compliance challenges that limit interoperability. For example, stored information may be subject to various privacy regulations such as Health Insurance Portability and Accountability Act (HIPAA). Privacy rules under HIPAA establish national standards to protect individual medical records and other personal health information when health care transactions are conducted electronically. These regulations may cover privacy (e.g. which entities have access to information), content (what information an authorized entity may access), security (how the information is protected from unauthorized access when stored and during electronic communication) and integrity (the accuracy and authenticity of information). In addition, commercially valuable information may be protected under an organizational policy that may limit sharing of the information with third parties (e.g. as trade secrets, and/or for business or commercial reasons). Regulations such as the European Union (EU) General Data Protection Regulation (GDPR) and state regulations may also impact information collection, storage, sharing, and communication. These regulations have affected the information available to healthcare marketplace participants and led to the creation of organizational "data silos," where information available to an entity is isolated, even when it could be useful systemically (e.g. to another non-competitive entity). Such compartmentalization of information has led to increased systemic costs (e.g. by a patient or medical provider considering the costs of treatment alternatives, treatment locations, etc.), raised patient risk (e.g. from drug interactions, prescription abuse etc.), and limited the efficacy of outcome based approaches to medical treatment or remediation (e.g. making it more difficult and expensive to determine when a desired outcome has been achieved or compare metrics in approaches that achieve similar outcomes). Systems and techniques to address one or more of the above issues that would help facilitate healthcare information security while promoting interoperability between marketplace participants are therefore desirable.

SUMMARY

In some embodiments, a processor-implemented method may comprise: receiving at least one encrypted first Electronic Health Record (EHR) sub-block decryptable by the first entity, wherein the at least one EHR sub-block comprises patient medical coverage information for a patient and one or more first treatments; transmitting, in response to the first EHR sub-block, at least one encrypted first Drug/Device Information (DIR) sub-block decryptable by at least one corresponding second entity, wherein the at least one first DIR sub-block comprises, for each of the one or more first treatments, a corresponding first treatment class, one or more corresponding first treatment class members associated with each corresponding first treatment class, and for each first treatment class member, corresponding first treatment class member cost information; receiving, in response to the first DIR sub-block, an encrypted second EHR sub-block decryptable by the first entity, wherein the second EHR sub-block comprises one or more second treatments, wherein each of the one or more second treatments is associated with a corresponding first treatment and each second treatment is selected from the corresponding first treatment class members associated with the corresponding first treatment; and augmenting, in response to a transaction confirmation, a multi-dimensional blockchain, wherein the multi-dimensional blockchain is augmented with a multi-dimensional block formed by linking: a DIR block comprising information associated with the one or more second treatments, an EHR block comprising information associated with the second EHR sub-block, and a transaction block.

In another aspect, a computing device for a first entity may comprise: a memory, a communications interface, and a processor coupled to the memory and the communications interface. In some embodiments, the processor may be configured to: receive at least one encrypted first Electronic Health Record (EHR) sub-block decryptable by the first entity, wherein the at least one EHR sub-block comprises patient medical coverage information for a patient and one or more first treatments; transmit, in response to the first EHR sub-block, at least one encrypted first Drug/Device Information (DIR) sub-block decryptable by at least one corresponding second entity, wherein the at least one first DIR sub-block comprises, for each of the one or more first treatments, a corresponding first treatment class, one or more corresponding first treatment class members associated with each corresponding first treatment class, and for each first treatment class member, corresponding first treatment class member cost information; receive, in response to the first DIR sub-block, an encrypted second EHR sub-block decryptable by the first entity, wherein the second EHR sub-block comprises one or more second treatments, wherein each of the one or more second treatments is associated with a corresponding first treatment and each second treatment is selected from the corresponding first treatment class members associated with the corresponding first treatment; and augment, in response to a transaction confirmation, a multi-dimensional blockchain, wherein the multi-dimensional blockchain is augmented with a multi-dimensional block formed by linking: a DIR block comprising information associated with the one or more second treatments, an EHR block comprising information associated with the second EHR sub-block, and a transaction block.

In a further aspect, an apparatus may comprise: means for receiving at least one encrypted first Electronic Health Record (EHR) sub-block decryptable by a first entity, wherein the at least one EHR sub-block comprises patient medical coverage information for a patient and one or more first treatments; means for transmitting, in response to the first EHR sub-block, at least one encrypted first Drug/Device Information (DIR) sub-block decryptable by at least one corresponding second entity, wherein the at least one first DIR sub-block comprises, for each of the one or more first treatments, a corresponding first treatment class, one or more corresponding first treatment class members associated with each corresponding first treatment class, and for each first treatment class member, corresponding first treatment class member cost information; means for receiving, in response to the first DIR sub-block, an encrypted second EHR sub-block decryptable by the first entity, wherein the second EHR sub-block comprises one or more second treatments, wherein each of the one or more second treatments is associated with a corresponding first treatment and each second treatment is selected from the corresponding first treatment class members associated with the corresponding first treatment; and means for augmenting, in response to a transaction confirmation, a multi-dimensional blockchain, wherein the multi-dimensional blockchain is augmented with a multi-dimensional block formed by linking: a DIR block comprising information associated with the one or more second treatments, an EHR block comprising information associated with the second EHR sub-block, and a transaction block.

In some embodiments, a non-transitory computer-readable medium may comprise executable instructions to configure a processor to: receive at least one encrypted first Electronic Health Record (EHR) sub-block decryptable by the first entity, wherein the at least one EHR sub-block comprises patient medical coverage information for a patient and one or more first treatments; transmit, in response to the first EHR sub-block, at least one encrypted first Drug/Device Information (DIR) sub-block decryptable by at least one corresponding second entity, wherein the at least one first DIR sub-block comprises, for each of the one or more first treatments, a corresponding first treatment class, one or more corresponding first treatment class members associated with each corresponding first treatment class, and for each first treatment class member, corresponding first treatment class member cost information; receive, in response to the first DIR sub-block, an encrypted second EHR sub-block decryptable by the first entity, wherein the second EHR sub-block comprises one or more second treatments, wherein each of the one or more second treatments is associated with a corresponding first treatment and each second treatment is selected from the corresponding first treatment class members associated with the corresponding first treatment; and augment, in response to a transaction confirmation, a multi-dimensional blockchain, wherein the multi-dimensional blockchain is augmented with a multi-dimensional block formed by linking: a DIR block comprising information associated with the one or more second treatments, an EHR block comprising information associated with the second EHR sub-block, and a transaction block.

Further, in another aspect, a processor-implemented method may comprise: obtaining, from at least one encrypted first Health Transaction Record (HTR) sub-block decryptable by the first entity, a first set of first treatments for the patient over a time period, wherein each first treatment comprises a first diagnosis code and a first treatment code; obtaining, based on the first set: (a) one or more second sets of second treatments, wherein each corresponding second treatment is associated with: a distinct first treatment in the first set, and (b) a corresponding number of recurrences for each second treatment; obtaining a set of available insurance plans available to the patient and corresponding coverage related information for each available insurance plan; obtaining, based on the set of second treatments and corresponding coverage related information for each insurance plan, corresponding estimated plan-specific cost metrics for the patient; and transmitting, a first encrypted Drug/Device Information Record (DIR) sub-block decryptable by at least one second entity, wherein the DIR sub-block comprises the plan-specific cost metrics for the patient.

In some embodiments, a computing device for a first entity may comprise: a memory, a communications interface, and a processor coupled to the memory and the communications interface. In some embodiments, the processor may be configured to: obtain, from at least one encrypted first Health Transaction Record (HTR) sub-block decryptable by the first entity, a first set of first treatments for the patient over a time period, wherein each first treatment comprises a first diagnosis code and a first treatment code; obtain, based on the first set: (a) one or more second sets of second treatments, wherein each corresponding second treatment is associated with: a distinct first treatment in the first set, and (b) a corresponding number of recurrences for each second treatment; obtain a set of available insurance plans available to the patient and corresponding coverage related information for each available insurance plan; obtain, based on the set of second treatments and corresponding coverage related information for each insurance plan, corresponding estimated plan-specific cost metrics for the patient; and transmit, a first encrypted Drug/Device Information Record (DIR) sub-block decryptable by at least one second entity, wherein the DIR sub-block comprises the plan-specific cost metrics for the patient.

In a further aspect, an apparatus may comprise: means for obtaining, from at least one encrypted first Health Transaction Record (HTR) sub-block decryptable by the first entity, a first set of first treatments for the patient over a time period, wherein each first treatment comprises a first diagnosis code and a first treatment code; means for obtaining, based on the first set: (a) one or more second sets of second treatments, wherein each corresponding second treatment is associated with: a distinct first treatment in the first set, and (b) a corresponding number of recurrences for each second treatment; means for obtaining a set of available insurance plans available to the patient and corresponding coverage related information for each available insurance plan; means for obtaining, based on the set of second treatments and corresponding coverage related information for each insurance plan, corresponding estimated plan-specific cost metrics for the patient; and means for transmitting, a first encrypted Drug/Device Information Record (DIR) sub-block decryptable by at least one second entity, wherein the DIR sub-block comprises the plan-specific cost metrics for the patient.

In some embodiments, a non-transitory computer-readable medium may comprise executable instructions to configure a processor to: obtain, from at least one encrypted first Health Transaction Record (HTR) sub-block decryptable by the first entity, a first set of first treatments for the patient over a time period, wherein each first treatment comprises a first diagnosis code and a first treatment code; obtain, based on the first set: (a) one or more second sets of second treatments, wherein each corresponding second treatment is associated with: a distinct first treatment in the first set, and (b) a corresponding number of recurrences for each second treatment; obtain a set of available insurance plans available to the patient and corresponding coverage related information for each available insurance plan; obtain, based on the set of second treatments and corresponding coverage related information for each insurance plan, corresponding estimated plan-specific cost metrics for the patient; and transmit, a first encrypted Drug/Device Information Record (DIR) sub-block decryptable by at least one second entity, wherein the DIR sub-block comprises the plan-specific cost metrics for the patient.

The methods disclosed may be performed by one or more of mobile computing devices, computers, including servers, cloud-based systems, etc. using computer-readable media or computer-readable memory.

BRIEF DESCRIPTION OF THE DRAWINGS

Embodiments of the invention will be described, by way of example only, with reference to the drawings.

FIGS. 10A and 10B show a flowchart of an exemplary method to facilitate healthcare insurance selection and cost determination, while maintaining healthcare information security and facilitate interoperability between a plurality of entities.

In the figures, like reference numbers and symbols in the various figures, which depict certain example embodiments indicate like elements. For example, sub-blocks with similar information are referred to with the same reference numbers. In addition, multiple instances of an element may be indicated by following a first number for the element with a letter or with a hyphen and a second number. For example, multiple instances of an element 280 may be indicated as 280-1, 280-2, etc. When referring to such an element using only the first number, any instance of the element is to be understood (e.g. element 280 in the previous example would refer to elements 280-1, 280-2 . . . and/or 280-N). Further, in the figures below, an asterisk symbol ("*") associated with a reference number indicates that the element (or some portion thereof) may be repeated (e.g. for each instance of the element). For example, a prescription may include several drug instances, and a dosage field may be repeated for each drug instance.

The figures below also show hierarchies of records, which may comprise fields and sub-fields. Records include any fields (and some or all parts of sub-blocks) that are part of the record. Similarly, a field includes any sub-fields. Sub-fields may include additional sub-fields.

DETAILED DESCRIPTION

Disclosed embodiments facilitate healthcare system security while promoting healthcare system integrity, interoperability, treatment selection, and cost transparency.

Figure 1:
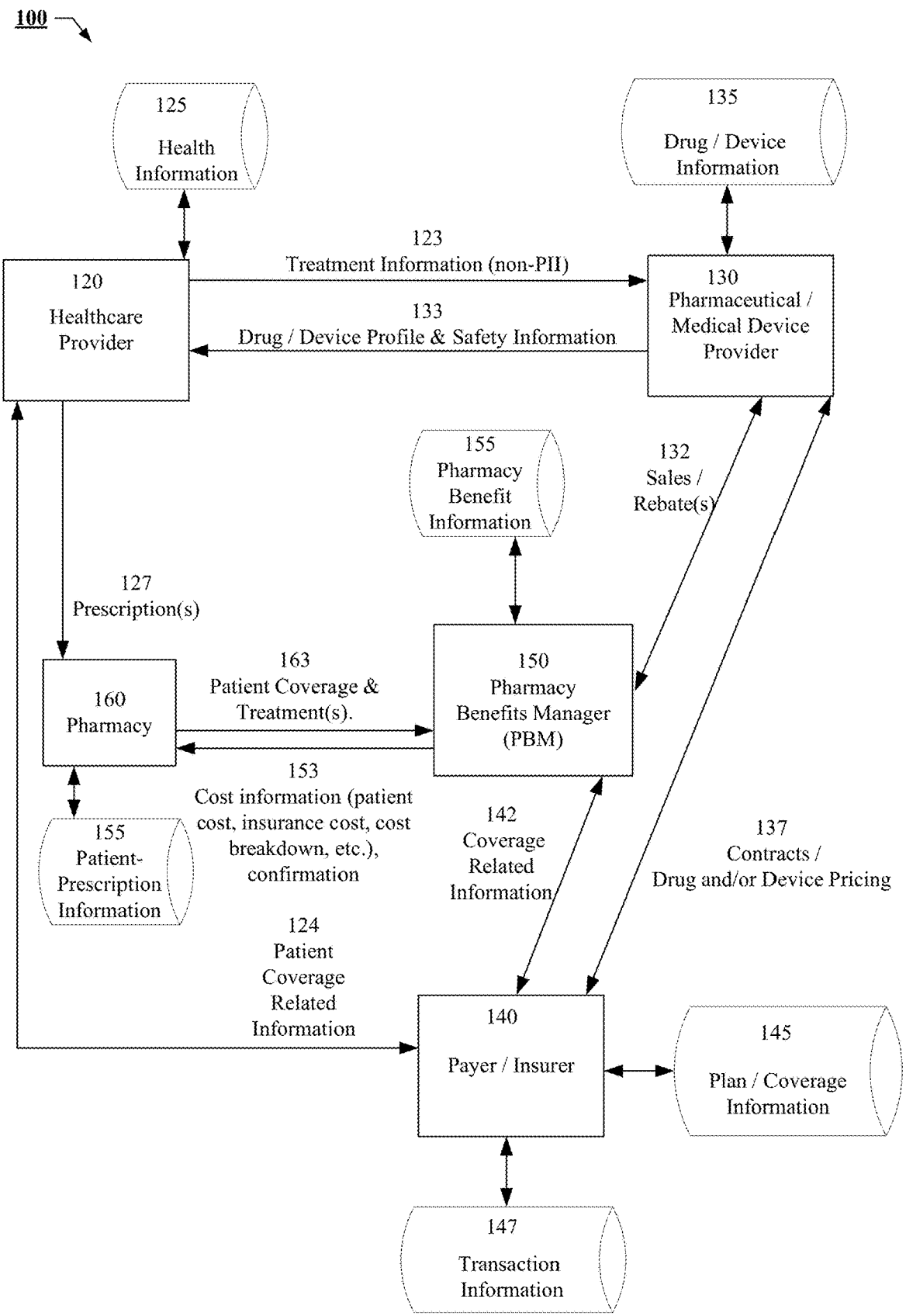
FIG. 1 shows a schematic block diagram illustrating interactions between some entities associated with a conventional healthcare information system.

FIG. 1 shows a schematic block diagram illustrating interactions between some entities associated with a conventional healthcare information system 100. Healthcare transactions may involve several entities, where each entity may have some transaction-relevant information, which may be used to complete the transaction. Thus, in conventional systems, some limited information (e.g. limited by regulation, contract, privacy considerations, confidentiality, and/or for competitive reasons) may be exchanged between the transacting entities in order to complete a transaction. The term "entity," as used herein, may refer to an individual (such as a patient or groups of patients) or an organization or that participates in a healthcare marketplace and/or to computing and information systems (e.g. hardware and/or software) associated with that individual/group/organization, which may participate in the healthcare marketplace on behalf of the individual/group/organization. For example, the computing systems associated with one entity may process and/or exchange information with computing systems associated with other entities. The exchange of information between entities may occur over secure communication networks and/or in a secure manner (e.g. using encryption) over the Internet and/or on an electronic platform (e.g. such as an information exchange and/or transaction exchange).

An entity such as a patient (not shown in FIG. 1) may seek treatment from another entity such as Healthcare Provider (HCP) 120 for a medical condition afflicting the patient. HCP 120 may determine patient treatment information and patient insurance using health information (HI) database 125, which may be maintained by HCP 120 and include patient coverage related information 124. Further, HCP 120 may propose a treatment for the patient's medical condition. When proposing a treatment to be prescribed, HCP 120 may send treatment information 123 to Pharmaceutical Provider and/or Medical Device Provider (PMDP) 130. Treatment information 123 sent to PMDP 130 may not include any patient personally identifiable information (PII).

Personally identifiable information (PII) is any data that could potentially be used to identify specific individuals. The term "non-PII" is used herein to qualify information that does not include PII. For example, a patient data record (with PII) may include a patient's name, full address, other identifiers (e.g. insurance identifier, driver's license number, social security number, and/or other identifying information) along with health related information. PII in the patient's data record may be removed to obtain a non-PII patient data record (without name, full address, and other identifying information). For example, the non-PII patient data record may include age, sex, medical history (e.g.

medical conditions afflicting the patient, other medication being used by the patient, etc.), treatment(s), and optionally (e.g. when appropriate) a city, state, and/or zip code, and may include full address of HCP 120 (where the care was delivered).

In response, PMDP 130 may send Drug/Device profile and safety information 133 to HCP 120 based on information in Drug/Device Information Record (DIR) database 135. DIR database 135 may include drug/device profile and safety information 133. Drug/device profile and safety information 133 may include information about drug characteristics such as dosage, mode of administration, absorption, metabolism, duration of action, toxicity, and interactions with foods or other medications. Upon receiving drug/device profile and safety information 133, HCP may prescribe one or more drugs and/or medical devices and/or procedures, or may revise the prescription based on the received Drug/Device profile and safety information 133.

As shown in FIG. 1, HCP 120 may also securely send stored patient insurance and treatment (e.g. medical procedure related) information 124 to Payer/Insurer (hereinafter "Payer") 140 and prescription information 127 to Pharmacy 160. Prescription information 132 may include patient ID and treatment (e.g. drug and/or device) information. Insurance related and treatment information 124 may include patient identification (ID) information, insurance plan information, group ID information, proposed treatment information (e.g. one or more of: medical procedure related information, drug related information, medical device related information, etc.). While insurance related and treatment information 124 may include some personally identifiable information (PII), the PII information shared may be limited. For example, patient insurance and treatment information 124 may not include patient family history and/or other patient information (which may be part of HI database 125) but may not be relevant to coverage determination, and/or cost determination, and/or precluded (e.g. by law/regulations) from being shared with Payer 140.

Pharmacy 160 may enter and/or update Patient-Prescription information (PPI) database 155 using the received patient prescription information 127 and may send patient insurance coverage and treatment related information 163 to Pharmacy Benefit Manager (PBM) 150.

PBMs 150 are entities that play a role in patient access to pharmaceutical products (drugs and/or devices). PBMs 150 determine pharmaceutical prices based PBMs 150 may set or determine retail prices for pharmaceutical products, obtain payments or rebates from manufacturers based on the sales volumes of a particular product or a basket of products, and, in some instances, may also obtain post-sale price concessions and payments from pharmacies on "formularies" for Payers 140. Formularies may determine: the drugs available to a patient based on their coverage and the distribution of drug costs (e.g. proportion of payment to be provided by a patient and the proportion to be paid by Payer 140 for each covered drug). Further, formularies typically assign drugs to one of a plurality of cost-sharing tiers. The drug prescribed and the drug's cost-sharing tier (which may both depend on a patient's health or prescription coverage) may determine the patient's out-of-pocket cost at the pharmacy. For example, drugs in a preferred tier may have lower cost-sharing requirements (e.g. lower coinsurance).

Thus, the patient's eventual share of a drug's cost at the pharmacy may depend on: (a) the plan's deductible (some specified amount to be paid each plan term by the patient before the payer cost shares); (b) co-payment (fixed out of pocket payment for each transaction as specified by the patient's health plan), and (c) coinsurance (percentage of a drug's cost to be borne by the patient after the deductible and co-payment requirements have been met). In some instances, based on patient qualification information, Pharmaceutical/Medical Device Provide (PMDP) 130 may provide upfront payment assistance to the patient. Patient qualification information may include one or more of: health insurance coverage information, patient out-of-pocket cost (which may include one or more of copayment, coinsurance, and deductibles for an individual prescription or over some time period), and demographic information associated with the patient (e.g. one or more of patient location, age, disability information, income, prescription costs, etc.). Conventionally, the patient payment assistance may be provided as a physical patient-specific discount card that is applied to the patient's out-of-pocket cost. The patient payment assistance may be provided by PMDP 130 through a patient access program, which, in some instances, may be administered separately in accordance with applicable laws and regulations. Partly because of the complexity of cost determination due to the number of entities involved and data compartmentalization by entities, patient cost information is typically not available to HCP 120 and/or to a patient at the time of prescription by the HCP (and may only be available after Pharmacy 160 and/or PBM 150 determine patient cost share).

For medical procedures, payer 140 may compare the received patient coverage related information 124 with information in Plan/Coverage database 145 to determine coverage for the patient. Based on the coverage information, Payer 140 may update transaction information database 147 and reply with a confirmation and/or additional/updated patient coverage related information 124 to HCP 120. Patient coverage related information 124 may include approval/denial information, coverage information related to the proposed treatment, and cost and payment related information such as patient co-pays, billing codes, etc. If the Payer withholds approval or the coverage for the proposed treatment is inadequate and/or does not meet the patient's cost criteria, HCP 120 may propose revisions, which may lead to further exchange of information between HCP 120 and Payer 140. The interactions between HCP 120, Payer 140, and PMDP 130 may continue until HCP 120 finalizes a treatment plan that: (a) is acceptable to the patient, (b) meets safety and efficacy considerations, and (c) may be covered and/or approved by Payer 140.

For drugs and/or devices, PBM 150 may use coverage related information received from the patient (or HCP) with information in Pharmacy Benefit Information (PBI) database 155 to determine patient coverage, whether the prescribed drug(s) are covered, the out-of-pocket patient drug cost, insurance share of drug cost, etc. When the treatment (e.g. drugs and/or devices) are covered, PBM 150 may send cost information 153 to Pharmacy 160. Cost information 153 (which may include one or more of patient out-of-pocket cost, insurance cost, cost breakdown, and/or other information) may be sent to Pharmacy 160, which may use the received cost information 153 to update PPI database 155. If the patient later wishes to change the prescription (e.g. to different or lower cost drug based on out-of-pocket cost information obtained by the patient from the pharmacy 160) the process may need to be repeated, which may lead to further exchange of information between the patient, HCP 120, Pharmacy 160, and/or PBM 150. Because cost information is not conventionally available to HCP 120 and/or to a patient at the time of prescription by the HCP, patients and/or HCPs 120 may be unaware of the cost-related aspects of prescriptions until out-of-pocket costs are determined by Pharmacy 160 (e.g. based on information provided by PBM 150). Thus, a prescribed treatment may need to be changed (or may go unfulfilled) if the cost is not acceptable to the patient thereby leading to systemic inefficiencies and poor resource utilization.

In addition, there may be other exchanges of information, for example, between Payer 140 and PBM 150 to exchange/verify patient coverage (e.g. whether the patient is currently covered), payment information (e.g. remaining patient deductible etc.). PBM 150 may send patient coverage information 142 to Payer 150 and receive confirmation on whether coverage is current and deductible related information, which may be used by PBM to determine out-of-pocket patient cost. Further, PMDP 130 and PBM may exchange sales and rebate related information 132, while PMDP 130 and Payer 140 may exchange contract related information and/or drug/device pricing related information 137.

Thus, conventional healthcare information systems suffer from several drawbacks. While each entity obtains and maintains information that may be relevant for operating its business, very little of that information may be shared (e.g. due to legal, privacy, and/or business considerations) and when information is shared, it is often piecemeal, devoid of context, untimely, and may not be useful for decision making/planning purposes. For example, HCP 120 and/or patient may not have cost information related to a treatment at the time of prescription. As another example, treatment alternatives and the costs of the various treatment alternatives may not be available to the patient or HCP 120 at the time when a prescription or treatment plan is being developed.

As another example, HCP 120 may not provide details of adverse drug effects that may be reported by the patient to PMDP 130 (e.g. due to privacy concerns). As another example, when adverse drug effect information is provided to PMDP 130 by HCP 120, the information may not include non-PII demographic information (e.g. age, location, medical condition, etc. for a patient—again out of privacy concerns) so the information may be of limited value to PMDP 130. In addition, in some instances, when adverse drug effects are reported by an entity (e.g. a patient), validation of adverse drug effects may often be performed by another entity to determine if the adverse event can be attributed to a prescribed drug. Validation, which may involve additional entities, can introduce additional complexities that can further delay reporting and/or create additional silos thereby further limiting the utility of the information (e.g. to PMDP 130).

Further, because the information exchanged may be compartmentalized and provided on an ad-hoc basis, aggregating the received information with information stored by the receiving entity may be cumbersome. Moreover, because each entity may index the information differently, it may be difficult or impossible for the receiving entity (or the sending entity) to the received (or sent) information to an information record stored by the sending entity (or stored by the receiving entity). For example, if HCP 120 provides adverse drug effect information to a PMDP 130 at some point in time, it may be difficult for HCP 120 and/or PMDP 130 to obtain additional patient or patient medical condition information pertaining to the adverse drug effect—even when that information may be legally shared. For example, compartmentalization of information may prevent or limit access by PMDP 130 to aggregate demographic information that may be of use in tailoring drug utilization. As a further example, it may be difficult for HCPs 120 and/or Payer's 140 to determine prescription abuse by patients.

Many modern machine learning (ML) and other artificial intelligence (AI) systems can process large amounts of data to determine hazards, identify patterns that may lead to desired outcomes, etc., which may lead to increased efficiencies, lower costs, and/or better outcomes. The siloing and compartmentalization of information also limits the applicability of such ML and AI techniques thereby contributing to additional inefficiencies.

Some attempts to introduce efficiencies into healthcare delivery focus on outcome based approaches. Payers 140 may tie reimbursement to the achievement of some agreed upon outcomes. For example, an outcome based contract may specify that HCP 120 will be reimbursed at some agreed upon rate based on a lowering of a patient's blood pressure to some defined range within some time period. Tracking and managing such outcome based contracts can be notoriously difficult in conventional systems because several exchanges of information may need to occur between HCP 120 and Payer 140 where each exchange is in compliance with legal, regulatory, privacy and business related guidelines.

While the use of blockchains to store health related information can facilitate ensuring the integrity and authenticity of the stored information, conventional techniques do not address issues raised by data sharing between entities in an environment of increasing transactional and regulatory complexity—such as maintaining data privacy while decreasing information compartmentalization. Moreover, conventional techniques also do not ensure timely information availability (e.g. to one or more entities in a manner compliant with legal and regulatory obligations) to facilitate transaction finalization. Further, conventional techniques do not ensure that entities have a coherent and consistent view of completed transactions. The lack of a coherent and consistent view of completed transactions across entities can constrain interoperability, data utilization, and the quest for increased operational efficiencies. In addition, the constraints on interoperability often limit organizational ability to maintain a customer-centric focus because customer (e.g. patient) requests for information to aid or enhance decision-making (e.g. independently or in coordination with HCPs) may be difficult to accommodate.

Disclosed embodiments facilitate healthcare system security while promoting healthcare system integrity, interoperability, and facilitate healthcare cost transparency. Some disclosed techniques facilitate timely exchange (e.g. at the time of a transaction) of appropriate data (e.g. compliant with legal, privacy, and business guidelines) to appropriate entities (e.g. authorized entities associated with a transaction), while facilitating a consistent and coherent view of the information across healthcare marketplace entities.

Interoperability is facilitated in part because multiple entities associated with a transaction may be able to tie appropriate relevant information shared during a transaction to the completed transaction using an agreed upon reference. Consistency and coherency are facilitated because locally recorded data (e.g. locally at an entity) may correspond to reference data (e.g. maintained on a shared platform) and each entity's view of the reference data (or portions of the reference data viewable by the entity) may be consistent with another authorized entity's view of the data (and/or with the other authorized entity's locally recorded data). In some embodiments, the reference data may be based on and/or take the form of a decentralized ledger. In some embodiments, the decentralized ledger may be accessible to authorized entities and each entity's view of the decentralized ledger may be compliant with legal, privacy, business, and/or contractual obligations. Further, efficiency is promoted because information relevant to decision-making is made available to entities early in the transaction cycle to facilitate early consideration of alternatives thereby decreasing the likelihood of and inefficiencies associated with transaction finalization and decreasing decision revisitation.

In some embodiments, a first entity (e.g. PMDP 130) may receive at least one encrypted first Electronic Health Record (EHR) sub-block (e.g. for a patient) that is decryptable by the first entity. The first EHR sub-block(s) may comprise patient medical coverage information for a patient and one or more first treatments (e.g. proposed drugs and/or devices, denoted by $F\_p$, $1 \leq p \leq P$. The encrypted first EHR sub-block may be received (e.g. by PMDP 130) with a transaction ID for a current transaction and, in some instances, may not include PII information for the patient. In other instances, (e.g. when authorized and/or when PMDP 130 determines or uses patient eligibility for a payment assistance program administered by PMDP 130), encrypted first EHR sub-block may be received (e.g. by PMDP 130) with a transaction ID for a current transaction and may further include PII information for the patient. In situations where patient PII information is received (e.g. by PMDP 130), then PMDP 130 may administer and fund the payment assistance program and may use a locally maintained blockchain consistent with disclosed embodiments to maintain patient privacy on behalf of PMDP so that access to patient PII information is restricted to program administrators and/or authorized personnel. Authorization to provide PII information may be obtained (e.g. in advance by HCP 120 or PMDP 130 or another entity) from the patient. In some embodiments, the first EHR sub-block may further indicate that the patient has provided assent to use of information in the first EHR sub-block to determine clinical trial participation eligibility.

The first entity (e.g. PMDP 130) may transmit, in response to the first EHR sub-block, at least one encrypted first Device Drug Information (DIR) sub-block that is decryptable by at least one corresponding second entity (e.g. HCP 120), wherein the DIR sub-block(s) comprise, for each of the one or more first treatments ($F\_p$, $1 \leq p \leq P$): a corresponding first treatment class (e.g. $K\_p$ representing drugs/devices that are in the same class as $F\_p$). Each treatment class $K\_p$ may include one or more corresponding first treatment class members (individual drugs/devices denoted by $C\_pd$, ($1 \leq p \leq P$, $1 \leq d \leq D\_p$), and each first treatment class member ($C\_pd$) may be associated with corresponding first treatment class member cost information ($M\_pd$). The first treatment class member cost information ($M\_pd$) for a corresponding first treatment class member ($C\_pd$) may include out of pocket costs, a total cost over an expected treatment duration, treatment, cost over some specified time period, etc.). $D\_p$ may represent the number of class members in treatment class $K\_p$.

For example, upon receiving the first EHR sub-block, the first entity (e.g. PMDP 130) may determine, for each of the one or more first treatments ($F\_p$), the corresponding first treatment class ($K\_p$). Further, in some embodiments, the first EHR sub-block may comprise patient-specific parameters and the corresponding first treatment class may be determined based on the patient-specific parameters. The patient-specific parameters may comprise one or more of: patient co-morbidity information, route of administration information, safety and efficacy information, and/or patient location information. Thus, members $C\_pd$ in a corresponding first treatment class ($K\_p$—corresponding to a treatment $F\_p$) may be determined (e.g. by the first entity) based on the patient-specific parameters.

Each first treatment class ($K\_p$) may comprise the one or more corresponding first treatment class members ($C\_pd$). Further, the first entity may determine, for each of the one or more first treatment class members ($C\_pd$), one or more corresponding first treatment class member cost information ($M\_pd$). The first entity (e.g. PMDP 130) may then transmit the encrypted first DIR sub-block(s) decryptable by at least one corresponding second entity (e.g. HCP 120).

The one or more corresponding first treatment class member cost metrics ($M\_pd$) include one or more of: a patient specific out-of-pocket cost corresponding to each corresponding first treatment class member ($C\_pd$) for a corresponding treatment unit; or a patient-specific estimated total out-of-pocket cost corresponding to each corresponding first treatment class member for a typical or prescribed treatment duration; or a patient-specific estimated total out-of-pocket cost corresponding to each corresponding first treatment class member ($C\_pd$) for the remaining duration of a medical coverage plan associated with the patient, or a combination thereof.

The first entity (e.g. PMDP 130) may receive, in response to the transmitted first DIR sub-block(s), an encrypted second EHR sub-block decryptable by the first entity, wherein the second EHR sub-block comprises one or more second treatments (e.g. one or more selected drugs/devices, $S\_p$, $1 \leq p \leq P$), wherein each of the one or more second treatments $S\_p$ is selected from corresponding first treatment class members ($C\_pd$) associated with a corresponding first treatment class ($K\_p$). For example, the set of second treatments $S$ may comprise, for each first treatment class ($K\_p$ corresponding to a first treatment $F\_p$) one selected corresponding first treatment class member ($C\_pd$). For example, the second EHR sub-block may comprise one or more selected devices/drugs, where each selected device/drug $S\_p$ is associated with a distinct corresponding class $K\_p$. As an example, the first EHR sub-block may include first treatments ($F\_1$, $F\_2$, $F\_3$) while the second EHR block may include second treatments $G\_1$, $F\_2$, $H\_4$} where $G\_1$ and $F\_1$ are both in treatment class $K\_1$, $F\_2$ is in treatment class $K\_2$, and $F\_3$ and $H\_4$ are in treatment class $K\_3$. As outlined above, each treatment classes may include one or more members. In some embodiments, the selection of the one or more second treatments ($S\_p$) may be based on patient-specific cost metrics.

In some embodiments, the first entity (e.g. PMDP 130) may then augment a multi-dimensional blockchain, wherein the multi-dimensional blockchain is augmented with a multi-dimensional block formed by linking: a DD1 block comprising information associated with the one or more second treatments, an EHR block comprising information associated with the second EHR sub-block, and a transaction block, which may comprise a transaction ID.

In some embodiments, upon receiving the second EHR sub-block, the first entity (e.g. PMDP 130) may transmit the transaction block with the transaction confirmation wherein the transaction block comprises at least one prescription for the one or more second treatments at one or more corresponding specified second treatment locations. In some embodiments, the transaction block may comprise a prescription for the second treatment at the specified location at a specified patient cost. In some embodiments, the first entity may further transmit a confirmation of the transaction along with the at least one prescription to the patient (e.g. associated with the first EHR sub-block and second EHR sub-block).

The term sub-block indicates a portion of a data record or a block. which (when encrypted) may be decryptable by some specific entity or entities (but not by other entities). Information in sub-block(s) decrypted by a specific entity (or entities) may be incorporated into data records (or data blocks in blockchains) that are being maintained by that specific entity (or entities) when a transaction is finalized. For example, a transaction with a transaction ID U may involve entities A, B, C, and D, which may be owners of data records W, X, Y, and Z, respectively, in a multi-dimensional blockchain. In the example above, a data record W (owned by A) and related to transaction U may be encrypted and readable by the owning entity A (but not by other entities). However, the data record W may include (in addition to transaction ID U) a portion of the information in other data records (e.g. data records X, Y, and/or Z, which may not be readable by entity A). For example, data from the one or more other data records (e.g. data records X, Y, and/or Z) that is present in W may have been received (e.g. by entity A) prior to transaction finalization as decryptable sub-blocks. Similarly, the other entities B through D may also include (in addition to transaction ID U) transaction related information present in a non-owned data records. For example, for entity B, information present in one or more of data records W, Y and/or Z, may have been received in the form of sub-blocks decryptable by entity B prior to transaction finalization. Thus, each entity A, B, C, and D may maintain distinct independent blockchains that include (for transaction U) data records W, X, Y, and Z, respectively, as blocks in their respective blockchains. The data records (or blocks) W, X, Y, and Z, associated with transaction U may also collectively form a multi-dimensional block in a multi-dimensional blockchain. Thus, a coherent and consistent view of the transaction is available to all marketplace entities that may be associated with a transaction while maintaining compliance with legal, privacy and/or other regulations/business considerations, and promoting data integrity.

The term "blockchain" as used herein, refers to a growable list of records or "information blocks" or "blocks," where the blocks are linked using cryptographic techniques. Each block includes a cryptographic hash of the previous block, a timestamp, and transaction data. A current block being added to the blockchain is also termed the head of the blockchain. A cryptographic hash function maps data of arbitrary size to a bit string of a fixed size, which is termed a "hash." Hash functions can be deterministic (the same input will produce the same output) and may be one-way functions that are infeasible to invert (i.e. determine the original data input from the hash value). The transaction data for a block may be represented as a Merkle tree root hash. The term "Merkle tree" or "hash tree" is used to refer to a tree, where every leaf node is labeled with a hash of the transaction data and each non-leaf node is labeled with the cryptographic hash of the labels associated with its child nodes. A block header for a block to be added to the blockchain may include a hash reference to the previous block header and a hash reference to the root of the Merkle tree that contains the transaction data. Blockchains promote data integrity because alterations to data in the blockchain results in inconsistencies in one or more of the hash references. The term record or data record is also used to indicate non-final data that is to be added to a blockchain. Once a data record has been validated and finalized the data record may be added to the blockchain and form a block in the blockchain.

The term "multi-dimensional blockchain" is used to refer to a sequence of multi-dimensional records (also referred to as multi-dimensional blocks), where each multi-dimensional record includes two or more data records. In some instances, each of the data records that may be viewed as forming a dimension of the multi-dimensional blockchain may also form blocks in a distinct blockchain associated with some entity. Thus, in some embodiments, a multi-dimensional block may comprise a data record in each dimension, where the data record corresponding to a dimension may form a block in a distinct conventional blockchain associated with a corresponding entity. For example, a multi-dimensional block may include an EHR data record as one dimension, a DIR data record as another dimension, and a Transaction data record as a third dimension. Further, in some instances, the EHR data record associated with a multi-dimensional block (in the multi-dimensional blockchain) may separately form a block in a distinct EHR blockchain (i.e. distinct from the multi-dimensional blockchain). Similarly, in some instances, the DIR data record and Transaction data record associated with a multi-dimensional block may each form a block in a distinct DIR blockchain (e.g. associated with PMDP 130), and a Transaction record blockchain (e.g. associated with Payer 140), respectively. Thus, in some instances, a data record in the context of the multi-dimensional blockchain may correspond to a block in a distinct conventional blockchain. In some instances, each data record (e.g. associated with a dimension) in the multi-dimensional block may correspond to, form part of, and/or or be derived from corresponding blocks in distinct conventional blockchains. The multi-dimensional block may include a cryptographic hash of a previous multi-dimensional block, a timestamp, and data. The data for the multi-dimensional block may include hashes of the individual data records that make up the multi-dimensional block. In some embodiments, a consensus mechanism between the entities may be used to confirm correctness of data in a proposed multi-dimensional block before that multi-dimensional block is committed and locked.

Thus, the multi-dimensional block may comprise two or more encrypted data records, where each encrypted data record may be associated with a distinct entity (e.g. in the healthcare marketplace). As outlined above, the data records in a multi-dimensional block may separately form blocks in distinct blockchains, where each of the blockchains may be associated with a distinct entity. Each encrypted data record may be decrypted by the corresponding associated entity (e.g. the data record owner). Further, an encrypted data record may include portions (termed "sub-blocks") with data that may have been decrypted by at least one other specific entity in addition to the encrypted data record owner. For example, the sub-block may have been decrypted by at least one other distinct entity (in addition to the data record owner) at the time the corresponding multi-dimensional block was formed. In some embodiments, at or prior to the time of multi-dimensional block formation, the sub-blocks may have been separately encrypted and made available to another entity along with information to decrypt the sub-blocks. Accordingly, a multi-dimensional block may facilitate availability of transaction data to a plurality of entities associated with a healthcare marketplace, while providing a coherent and consistent view of the data to authorized marketplace entities, complying with privacy and/or data sharing regulations, business guidelines, and/or contractual obligations, and promoting data integrity. Entities may also ensure data correlation (e.g. of a record associated with a dimension of a multi-dimensional block in the multi-dimensional blockchain) with a corresponding block in a locally maintained blockchain. In embodiments, when information is exchanged between two entities using sub-blocks, the information exchanged via the decryptable sub-blocks may be based on an informational interface between the two entities. In some embodiments, when exchanging information (e.g. at the time of multi-dimensional block formation), each entity may encrypt blocks associated with a local blockchain maintained by the entity while generating sub-blocks that are decryptable by the other entity. The informational interface may be based on a smart contract associated with the blockchain.

The term "smart contract" is used to refer program code or logic, which, in some instances, may be associated with a blockchain or a blockchain platform. The "smart contract" may encode rules or agreement between two or more entities in relation to data sharing, transactions, access, contract fulfillment, etc. The smart contract may be based on a contract between two or more entities and/or agreements related to the multi-dimensional blockchain platform. For example, "smart contract" program code associated with the multi-dimensional blockchain may process transaction requests and determine the validity of transactions based on program logic.

Figure 2:
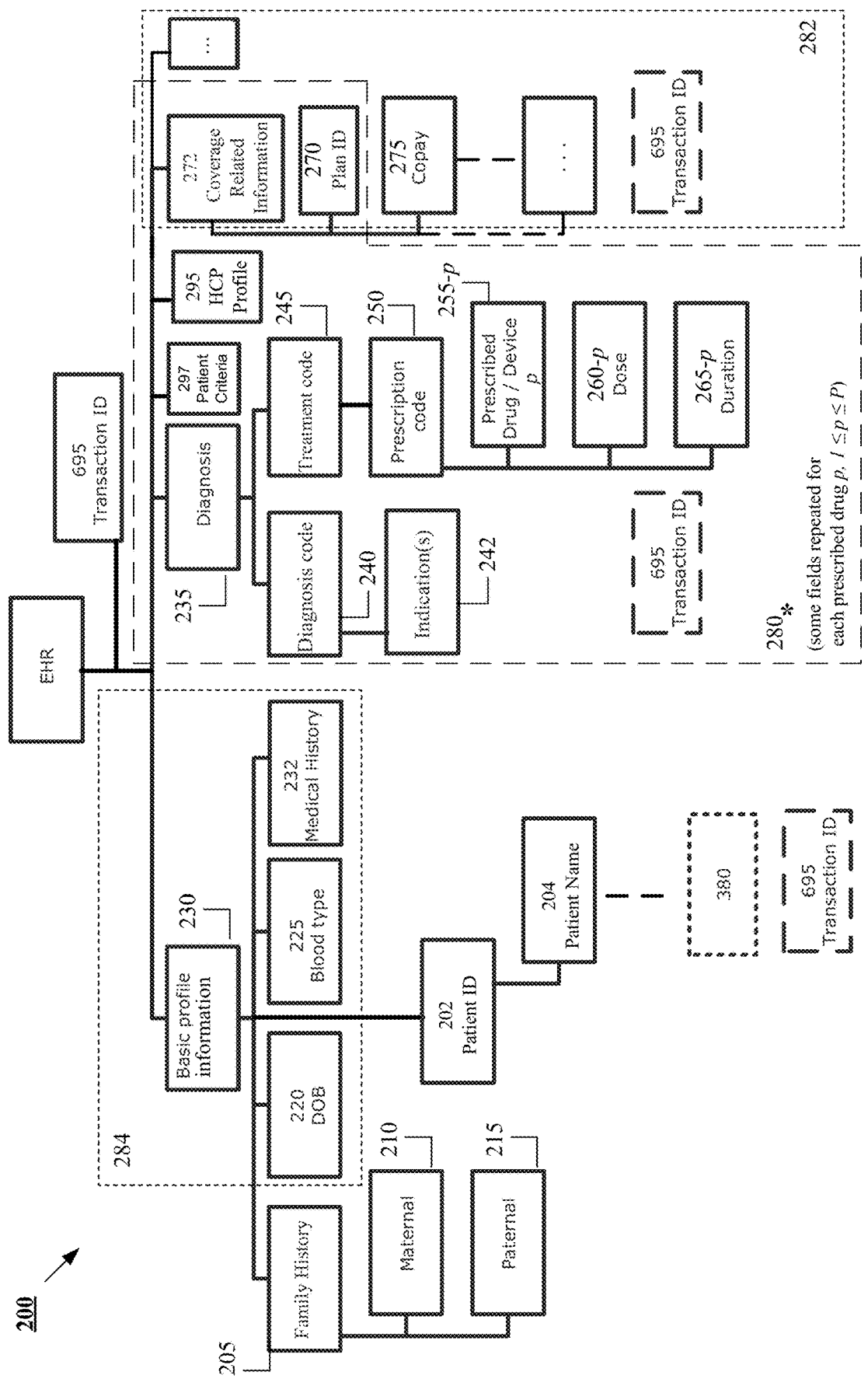
FIG. 2 shows an exemplary Electronic Health Record illustrating some exemplary data fields in a record.

FIG. 2 shows an EHR 200 illustrating some exemplary data fields in a record. In some embodiments, EHR 200 may include information about a patient and may be owned and maintained by HCP 120 (e.g. in HI database 125). In some embodiments, data fields in EHR 200 may be populated and/or updated by HCP 120 based, in part, on information received from a patient. EHR 200 may also include data received (e.g. as sub-blocks) from other entities. The fields shown in EHR 200 are merely exemplary, and EHR 200 may comprise various other additional fields based on laws, standards, HCP practice, and/or industry practice, etc. An EHR may comprise fields different from (fewer or greater than) those shown in relation to exemplary EHR 200.

EHR 200 may be associated with HCP Profile field 295, which may store information pertaining to HCP 120 (e.g. HCP identification, registration and/or licensing information, address, associated medical professionals, medical professional identification/registration information, etc.). In some embodiments, some or all of the information in HCP Profile 295 may be shared with other entities in connection with a transaction. For example, a portion of HCP Profile 295 may be sent to one or more entities such as PMDP 120, Payer 140, PBM 150, and/or Pharmacy 160 (e.g. as part of an encrypted sub-block, which may be decryptable by the designated receiving entity).

For example, as shown in FIG. 2, EHR 200 may comprise basic profile information 230 about a patient, which may change relatively infrequently. Basic Profile information 230 may include Patient Name, Patient ID, Family History 205, Date of Birth (DOB) 220, Blood Type 225, etc. Family History 205 may include Maternal History 210 and Paternal History 215. Basic Profile Information 230 may also medical history 232, which may include information about other prior or current medical conditions associated with the patient.

EHR 200 may further comprise other data fields such as Diagnosis 235 (e.g. for a current ailment), Diagnosis Code 240, which may be a standardized code for the diagnosis (such as an International Classification of Diseases (ICD) code), Treatment Code 245, which may be a standardized code to describe the treatment (e.g. such as a Current Procedural Terminology (CPT) code), Prescription Code 250 for each prescription, which may serve to uniquely identify each prescription. Prescription code 250 is also referred to herein as prescription 250.

In some embodiments, prescription code 250 (for a prescription) may include further include (e.g. for each drug/device being prescribed in the prescription) one or more subfields such as: a Prescribed Drug field 255-$p$, $1 \leq p \leq P$ (e.g. drug ID and/or a Classification Product Code (CPC) for medical devices), Dosage 260-$p$ (strength and frequency), and Duration 265-$p$ (length of time over which the drug is to be taken). In some instances, EHR 200 may also comprise other fields and/or sub-fields such as an indication of whether a prescription is a new prescription, or a refill. EHR 200 may also include Medical Device Report (MDR) adverse event codes, or other (e.g. ICD-10) codes to document adverse drug effects. EHR 200 may also include Patient Criteria 297, which may specify one or more criteria for drug/device selection and/or cost metric determination that may be provided by a patient. For example, Patient Criteria 297 may specify a preferred method of administration (e.g. topical, ingested, inhaled, etc.), preferred pharmacies, an area or location where prescribed drugs/devices are to be obtained, types of cost metrics desired, etc.

In some embodiments, EHR 200 for a patient may be stored as a blockchain, for example, by HCP 120 and each transaction between HCP 120 and the patient and/or another entity may form part of an EHR information block in the EHR blockchain. When an EHR block associated with a transaction is stored in a blockchain, the stored information may, in some instances, be associated with Transaction ID 695, which may serve to uniquely identify the transaction. In some embodiments, Transaction ID 695 may be common to entities associated with a transaction (e.g., all entities associated with a transaction may use the same transaction ID). In some embodiments, a transaction initiator and/or components of a permissioned blockchain platform may provide transaction information such as Transaction ID 695 to one or more entities associated with a transaction. Accordingly, sub-blocks sent or received by entities may be identified as being associated with a transaction and processed appropriately. In some embodiments, the format and content of Transaction ID 695 may be determined and/or agreed to in advance by entities associated with the transaction platform and/or provided by the transaction platform. Other transaction information related fields (not shown in FIG. 2) may include a transaction type, which may be used by an entity to determine and process information in transmitted and/or received sub-blocks and determine an appropriate response. For example, a transaction type may indicate that sub-block 280 is being provided to obtain cost-metrics associated with a prescription.

In the description below, when an EHR is maintained as a blockchain (e.g. by HCP 120), then EHR information record 200 may also be referred to as EHR block 200. EHR block 200 may thus form a block in an EHR blockchain. When an EHR block 200 is to be added to an EHR blockchain, some of the data in EHR block 200 being added to the EHR blockchain may depend on other entities. For example, a treatment (e.g. specified in treatment code 245 for a diagnosis described by diagnosis code 240) may be subject to approval by Payer 140 and/or PBM 150 (not shown in FIG. 2) and may be included as part of an EHR upon approval. As another example, a drug warning label (not shown in FIG. 2), which may form part of EHR block 200 may use input from PMDP 130 to complete, validate, and/or update information in the warning label prior to EHR block 200 being added to the EHR blockchain.

In some embodiments, Patient Criteria 297, Diagnosis 235, Diagnosis Code 240, Treatment Code 245, Prescription Code 250 along with data fields Prescribed Drug/Device 255-$p$, Dosage 260-$p$, and Duration 265-$p$, $1 \leq p \leq P$, may be used to form sub-block 280. In some embodiments, sub-block 280 may further include one or more of: basic profile information 230, patient coverage related information 272 and/or plan ID 270, which may serve to identify an insurance plan (e.g. health insurance plan, pharmacy benefits plan, prescription coverage, etc.) subscribed to by the patient. In some embodiments, (depending on context, applicable laws, and/or patient authorization) sub-block 280 may also include some or all of the information in sub-block 282 and/or 284 described herein. Some or all of the information in sub-block 280 may be shared with one or more other entities and may form part of other records/blocks associated with the transaction.

Prescription 250 may comprise one or more prescribed drugs/devices 255-$p$, $1 \leq p \leq P$, where P represents the number of drugs associated with a prescription 250. Thus, in some embodiments, sub-block 280 may comprise a record for each prescribed drug/device 255-$p$ in prescription 250. Sub-block 280 is merely an example that illustrates some information that may be shared with another specific entity. For example, sub-block 280 may be encrypted and sent to PMDP 130 (e.g. to obtain equivalent classes of drugs, devices, and/or treatments and corresponding cost metrics) and may be decryptable by PMDP 130.

In general, information in any appropriate field or combination of fields in a data record or block may be aggregated into a sub-block, which may be encrypted (e.g. by a first entity), so that the sub-block is decryptable by some other specific entity or entities (e.g. one or more second entities). The encrypted sub-block may be sent (e.g. by the first entity) to the other specified entity or entities (e.g. the one or more second entities), which may decrypt and act as appropriate (e.g. based on the transaction type) on the received information. The information that is used to form sub-blocks from a data record or a block in a locally maintained blockchain (e.g. an EHR blockchain) by a first entity and shared with another (second) entity may depend on regulations (e.g. healthcare and/or privacy), laws governing information sharing (e.g. which may determine information that can or cannot be shared between specific entities), business guidelines (e.g. which may govern sharing/protection of trade secret or sensitive information) and/or contractual obligations (e.g. between or related to the entities sharing information) and/or agreements (e.g. as part of a subscription to an electronic transaction platform).

As another example, information in sub-block 282 may include coverage related information 272, Plan ID 270, Co-payment information 275, etc. Some information in sub-block 282 may have been obtained directly from patient, while other coverage related information may have been obtained from and/or confirmed by Payer 140 and/or PBM 150 and decrypted by HCP 120 (e.g. based on one or more encrypted sub-blocks received from the appropriate entity and decrypted by HCP 120—not shown in FIG. 2) in connection with a transaction (e.g. to determine a cost-effective treatment) specified by Transaction ID 695. For example, a transaction type may indicate that sub-block 282 is being provided to obtain, confirm, or complete coverage related information 272.

Further, in some contexts, a portion of EHR information 200 such as some portion of Basic Profile information 230, DOB 220, Blood Type 225, and Medical History 232 may be encrypted by HCP 120 as sub-block 284 and sent to PMDP 130, which may then decrypt sub-block 284 in connection with a transaction (e.g. to determine a level of payment assistance) specified by Transaction ID 695. As a further example, the portion of basic profile information 230 included in sub-block 284 may be non-PII (e.g. exclude name, identification number, etc.) related to a patient. Thus, medical information may be shared (e.g. to determine adverse reactions, medical device malfunctions, etc.) with another specific entity securely without compromising patient privacy. In another instance, where disclosure of PII information is permitted and authorized (e.g. by the patient), a sub-block may include PII information (e.g. for PMDP 130 to determine patient eligibility for payment assistance, or in relation to a prescription (for pharmacy 160 to establish patient identity). For example, (depending on context, transaction type, applicable laws, and/or patient authorizations) some or all of the information present in sub-blocks 282 and/or 284 may also be incorporated into sub-block 280.

As a further example, data in a sub-block 280 may be shared by an entity such as HCP 120 with another healthcare marketplace entity such as Payer 140 to complete a transaction. However, patient profile information (e.g. family history 205, maternal history 210, and/or paternal history 215) associated with Basic Profile Information 230 may be deemed private (e.g. based on patient instructions/privacy, legal, and/or business guidelines) and the first entity (e.g. HCP 120) may not share family history 205, or may limit the portion of Basic Profile Information 230 that is shared.

Accordingly, in some embodiments, data used to form sub-blocks sent by an entity or received from another entity may depend both on the entity and the context (e.g. type or nature of transaction) in which the data is being shared. In some embodiments, the informational interface between any two entities may depend on the transaction type and/or context. In some embodiments, one or more protocols (e.g. agreed to/prearranged by entities and/or set up by a permissioned blockchain platform and/or based on a standard) may specify transaction types and the information to be present in sub-blocks sent/received by an entity for each transaction type. In some embodiments, the data fields included in a sub-block shared between entities in connection with a transaction type may be indicated (e.g. by the protocol and/or agreed upon standard) as mandatory, conditional, optional, on request, etc.

Data in a sub-block (e.g. sub-block 280) may be separately encrypted and may be decryptable only by an authorized entity. In some embodiments, encryption of data that forms a sub-block (e.g. sub-block 280) may be based on any appropriate cryptographic method, including symmetric key encryption techniques (where the entities, such as HCP 120 and Payer 140 share a secret key) such as Advanced Encryption Standard (AES) based techniques or variations thereof. Sub-block 280 may be encrypted (e.g. by HCP 120) prior to being shared with the other entity (e.g. Payer 140). The other entity (e.g. Payer 140) may be able to decrypt sub-block 280, for example, using the shared key.

Further, the data in EHR 200 may also be separately encrypted by HCP 120 using any secure encryption technique to form EHR block 200 prior to being added to a blockchain (e.g. maintained by HCP 120 and/or maintained by an electronic transaction platform). For example, the data in EHR block 200 may be separately encrypted using a private key (e.g. private to HCP 120), so that it is decryptable by and available to HCP 120 but unavailable to and/or not viewable any other entity.

Figure 3A:
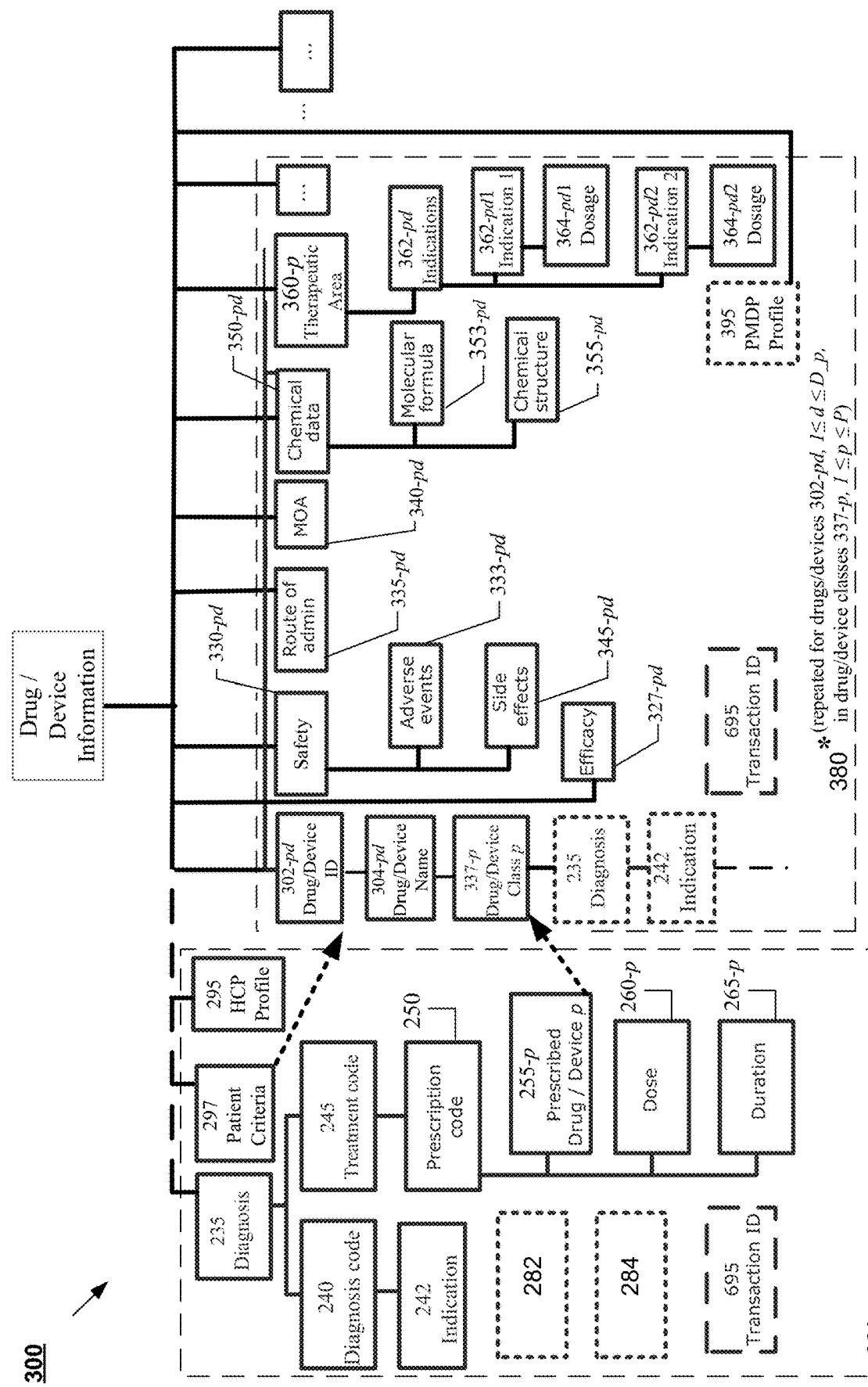
FIGS. 3A and 3B show portions of an exemplary Drug/Device Information Record (DIR) for a drug.
Figure 3B:
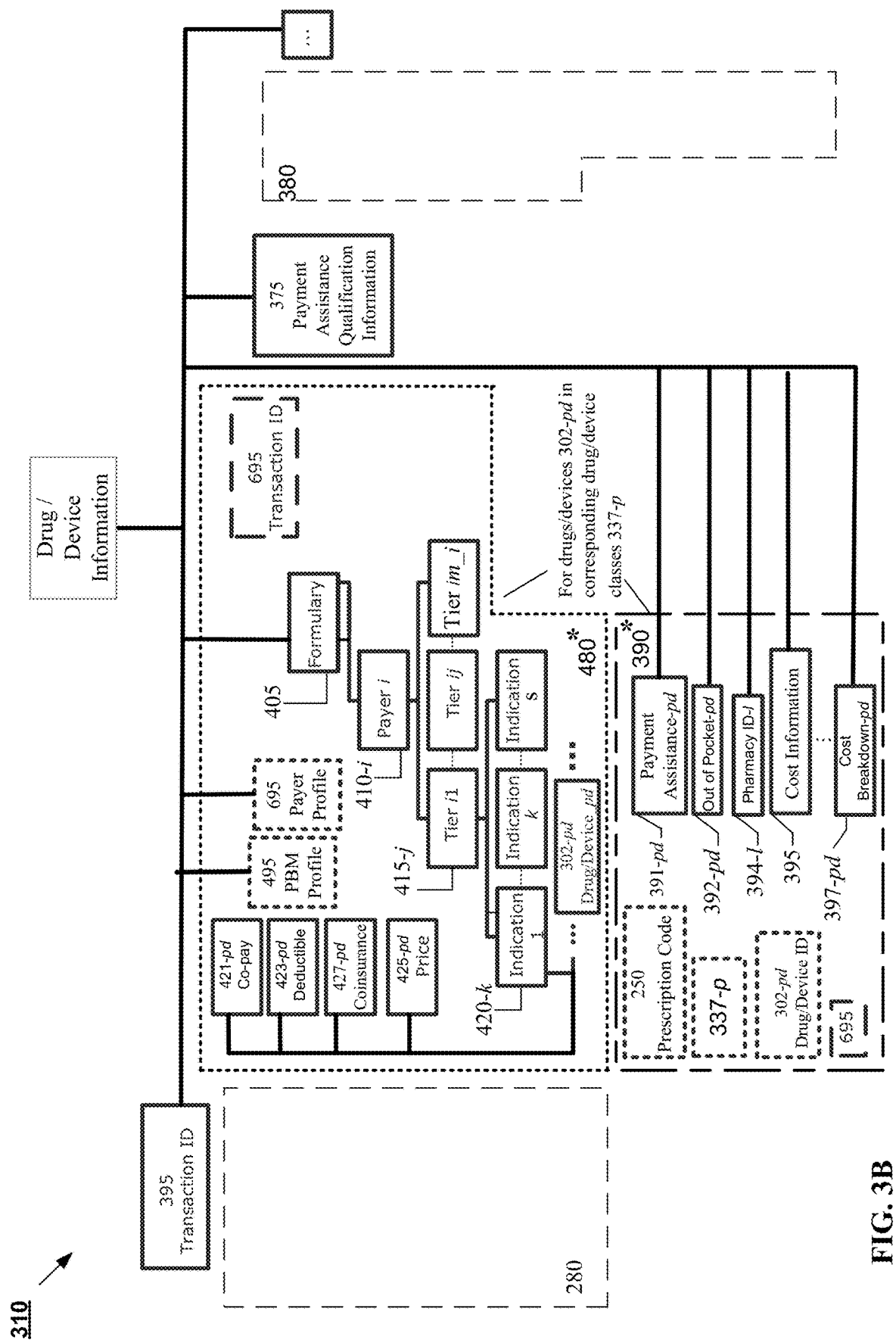

FIGS. 3A and 3B show portions of example Drug/Device Information Record (DIR) 300 for a drug, which may be stored in DIR database 135. In some embodiments, DIR 300 may include information about a treatment (e.g. drug and/or medical device) such as a drug, device, and/or procedure. The fields shown in DIR 300 are merely exemplary, and DIR 300 may comprise various other fields based on laws, standards, industry practice, etc. In addition, a DIR may comprise fields different from (fewer or greater than) those shown in relation to exemplary DIR 300.

DIR 300 may be associated with PMDP Profile field 395, which may store information pertaining to PMDP 120 (e.g. PMDP identification, contact information, address, etc.). In some embodiments, some or all of the information in PMDP Profile 395 may be optionally shared with other entities in connection with a transaction. For example, a portion of PMDP Profile 395 may be sent to one or more entities such as Payer 140, PBM 150, and/or Pharmacy 160 (e.g. as part of an encrypted sub-block, which may be decryptable by the designated receiving entity).

Referring to FIG. 3A, PMDP 130 may use information in prescribed drug/device field 255-$p$ (e.g. received as part of sub-block 280) to determine (e.g. for each drug/device 255-$p$ associated with prescription code 250) a corresponding drug/device class 337-$p$. Drug/Device Class 337 field may specify one or more drug/device classes associated with drugs/devices 255. In some embodiments, sub-block 280 may also include some or all of the information in sub-blocks 282 and/or 284.

Figure 3C:
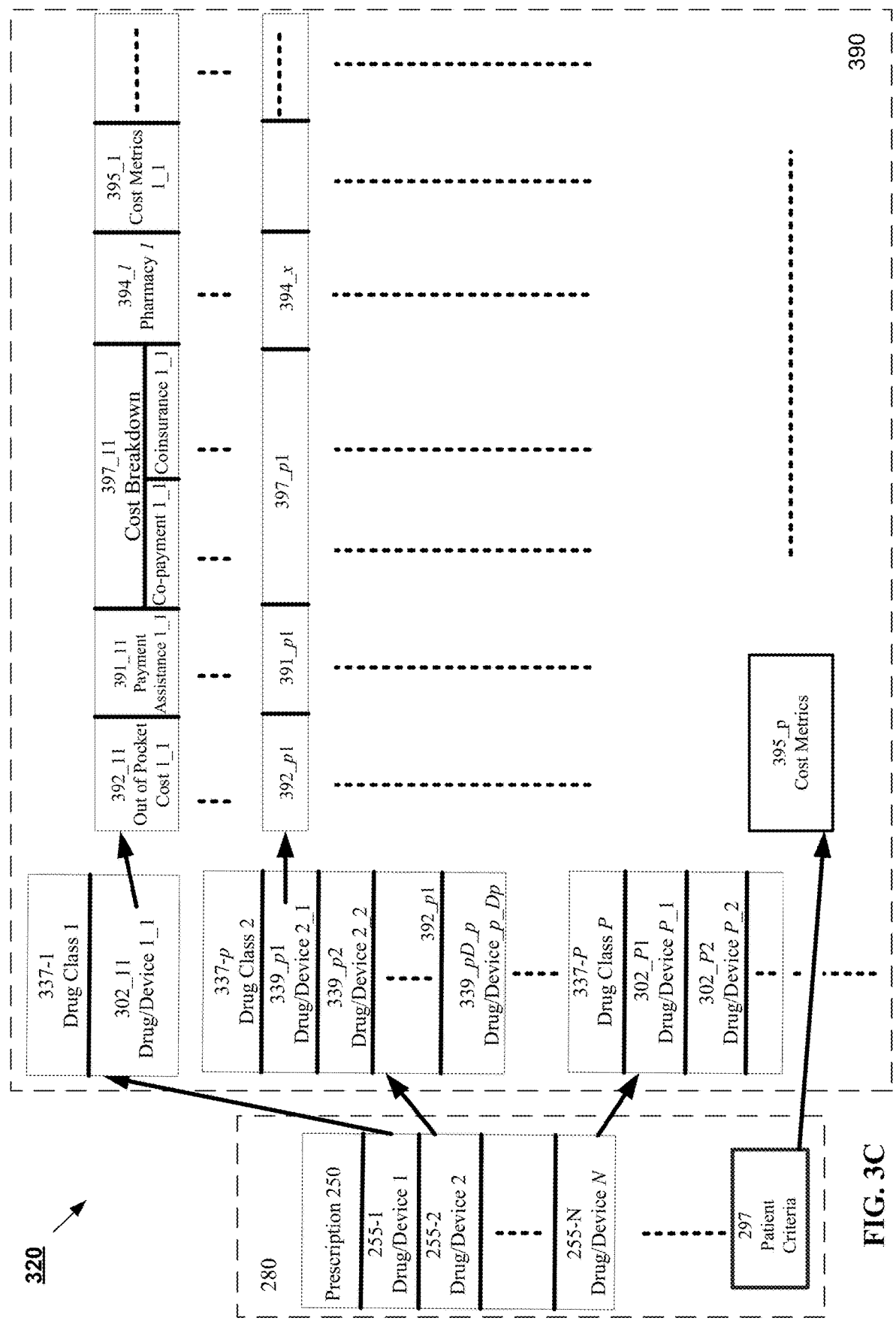
FIG. 3C shows an example data flow from an initial proposed prescription to alternatives that may be presented to a patient and/or an HCP along with cost information.

A drug/device class may be a set of drugs/devices that may be used to treat the same medical condition. Drugs in a drug class may have: similar chemical structures, and/or similar or related mechanisms of action (e.g. may act on or bind to the same target), and/or related modes of action (induce similar biological or functional effects), and/or may be used to treat the same disease. For example, a drug device class may also include name brand drugs/devices and generic drugs/devices, and/or branded biological products and biosimilars, and/or different dosages of the same treatment, etc. In FIGS. 3A-3C, drugs within an individual drugs/device class 337-$p$ are indicated by drug/device 302-$pd$, where $1 \le d \le D\_p$, where $D\_p$ is the number of drugs in drug/device class 337-$p$.

In some embodiments, Drug/Device Class 337-$p$ field may indicate one or more of: an organ or biological system that the drug device treats, and/or a therapeutic area, which may be specified by Therapeutic Area field 360-$pd$ comprising repeating Indications sub-fields 362-$pd$1, 362-$pd$2 . . . ; repeating Dosage sub-fields 364-$pd$1, 364-$pd$2 . . . for a corresponding indication; mechanism of action and/or mode of action, which may be specified by MOA field 340-$pd$; general chemical properties of a drug, which may be specified by Chemical Data field 350-$pd$, which may further include sub-fields Molecular Formula field 353-$pd$ describing the drug's chemical components and Chemical Structure sub-field 355-$pd$.

Referring to FIG. 3A, DIR 300 may comprise various other data fields including Drug Name(s) 304-$pd$ for a drug/device ID 302-$pd$, Efficacy 327-$pd$ (which may be a measure of therapeutic effect for a medical condition), Route of Administration 335-$pd$ (e.g. topical, oral, intravenous, etc.), Safety 330-$pd$ (e.g. drug interactions, toxicity, contraindications, etc.), which may include Side Effects sub-field 345 (e.g. secondary effects), and. Adverse Events sub-field 333-$pd$ (e.g. adverse events reported for the drug). DIR 300 may also include various other fields related to the drug/device.

In some embodiments, Drug/Device ID 302-$pd$. Drug/Device Name 304-$pd$, Safety 330-$pd$ (and sub-fields), and Efficacy 327-$pd$, Drug/Device class 337-$p$, Therapeutic Area 360-$p$, Indications 362-$pdh$ (e.g. Indications 362-$pd$1, Indications 362-$pd$2, etc.), and corresponding Dosages 364-$pdh$ (e.g. Dosage 364-$pd$1, Dosage 364-$pd$2, etc.), may form part of sub-block 380. The information in sub-block 380 (and any other sub-block) may be pre-arranged between the entities, determined by protocol, and/or specified by the platform (e.g. based on laws, regulations, authorizations, and/or contractual obligations). Thus, information in sub-block 380 (and any other sub-block) may be more or less than that shown for an example sub-block (e.g. example sub-block 380) and may also depend transaction type, transaction context, and the interacting entities. Sub-block 380 may further optionally include Route of Administration 335-$pd$, MOA 340-$pd$, Chemical Data 350-$pd$, and other related fields/sub-fields. In FIG. 3A, fields associated with example sub-block 380 are shown enclosed within a dashed perimeter.

DIR sub-block 380 may be provided to another entity (e.g. HCP by PMDP 130 in connection with a transaction e.g. identified by Transaction ID 695). In some embodiments, DIR sub-block 380 may comprise information for a plurality of drugs/devices that form part of Drug/Device class 337-$p$ or share one or more characteristics (e.g. treat the same medical condition, and/or have similar mechanisms or modes of action, and/or have similar chemical structures). In some embodiments, information in sub-block 380 may be associated with a transaction (e.g. identified by Transaction ID 695 and a transaction type) and may be encrypted and transmitted by PMDP 120 to another entity (e.g. HCP 120) during the transaction and/or prior to transaction finalization.

In some embodiments, a DIR record 300 may be associated with a transaction (e.g. specified by transaction ID 695) and may be stored upon transaction finalization as a DIR block a DIR blockchain by an entity such as PMDP 130. In the description below, when DIR record 300 forms part of a DIR blockchain, then DIR information record 300 may also be referred to as DIR block 300. DIR block 300 may thus form a block in a DIR blockchain.

A transaction (e.g. specified by transaction ID 695) between two or more entities (e.g. patient, HCP 120, PMDP 130, Payer 140, PBM 150 and/or Pharmacy 160) may involve information (e.g. related to a drug/device) that is maintained (or owned) by another entity. For example, HCP 120 may request information from PMDP 130. Prior to transaction confirmation, some of the data (e.g. maintained by PMDP 120 in a DIR information block 300), which is being integrated into records maintained by other entities (i.e. other the PMDP 130) may depend on input from, validation by, and/or confirmation by PMDP 130. Conversely, PMDP 130 may receive input from another entity (e.g. HCP 120 and/or Payer 140 and/or PBM 150) in the form of sub-blocks. Some or all of the received information may be incorporated into DIR record 300 and/or used to determine information in DIR record 300.

For example, HCP 120 may send sub-block 280 to PMDP 130. PMDP 130 may use information in sub-block 280 (e.g. a Prescribed Drug 255-$p$) to determine a corresponding Drug/Device class 337-$p$ and obtain the information in sub-block 380, which may be sent to Payer 140 and/or PBM 150. In addition, PMDP 130 may store some of the information in a current (e.g. last received) sub-block 280 prior to transaction finalization as part of DIR record 300. For example, information pertaining to the diagnosis (e.g. Diagnosis code 240), dosage (e.g. Dose 260) etc. may be stored as part DIR record 300 and associated with corresponding Drug/Device IDs 302-$p$ upon confirmation (e.g. from HCP 120) that the drug in Drug/Device ID field is being prescribed (e.g. as may be indicated by the value of Prescribed Drug field 255 in sub-block 280 at the time of transaction confirmation).

Accordingly, when information (e.g. related to the drug/ device) pertinent to a transaction is requested, the owner (e.g. PMDP 130) may respond by sending the information (e.g. in sub-block 380) to the requesting entity (e.g. HCP 120). The information (e.g. in sub-block 380) may be encrypted (e.g. by PMDP 130) prior to sending and may be decryptable by the requesting entity (e.g. HCP 120) so that the information in sub-block 380 is private between the requesting (HCP 120) and sending (PMDP 130) entities. In addition, information in the sub-blocks exchanged between entities may be restricted so that the information shared is compliant with existing regulations, privacy laws, contractual obligations, and/or authorizations received from a designated owner of the information (e.g. a patient).

FIG. 3B shows example DIR record 300 with some additional information that may be included in DIR record 300 in connection with a transaction. In FIG. 3B, sub-blocks 280 and 380 are shown by blocks with dashed outlines. For simplicity and ease of description, information in sub-blocks 280 and 380 is not shown. As outlined previously, some or all of the information in sub-block 280 may form part of DIR record 300.

As shown in FIG. 3B, DIR record 300 may further include Formulary 405, which may include a list of approved prescription drugs (e.g. generic and brand name) related to a therapeutic class. The drug formulary may be used by to identify drugs and/or devices covered by a drug plan and/or an insurance plan. The formulary may be updated periodically and/or published. For example, laws, regulators, health insurance exchanges, and/or private employers may specify that formularies for available/approved insurance plans be published and updated at specified times. Accordingly, in some instances, formulary information for various plans may be publicly available, and/or available to plan subscribers (e.g. an organization subscribing to the plan on behalf of its members/employees) and/or available from other entities (e.g. regulators, health exchanges, etc.).

Formularies may distinguish between products by dividing treatments into "tiers." Each tier may have a different level of patient cost sharing. For example, for drugs/devices in a preferred tiers, patient cost sharing may be $0 or limited to co-payments specified in the patient's insurance plan (subject to deductibles). Drugs/devices in non-preferred tiers may be subject to additional patient cost sharing, often referred to as "coinsurance." For example, a patient prescribed a non-preferred drug may pay some percentage of the drug price (e.g. 30%) as coinsurance in addition to copayments. The amount of coinsurance may depend on the tier. Similar "tiers" may also apply to devices and/or other medical treatments.

Accordingly, Formulary 405 may include repeating Payer-i field 410-$i$, (1≤i≤n) each with information about a corresponding payer i. Further, Formulary 405 may include, for each Payer-i 410-$i$, information about corresponding drug tiers, which may appear in repeating Tier-j field 410-$j$, (1≤j≤T_i), where T_i is the number of tiers associated with Payer-i. The tier associated with a drug may depend on the indication (e.g. as listed in Indication field 420-$k$) for which the drug is being used and Payer-i 410-$i$. For example, Formulary 405 in DIR record 300 for a drug may specify (e.g. for Payer 1 410-1 and some Indication 320-$k$) that a first generic drug is a Tier 1 415-1, while a more expensive second generic drug is a Tier 2 415-2 drug, and a brand name drug is a Tier 3 415-3 drug. Further, each Tier-j field 410-$j$ may include repeating Indication-k field 420-$k$, (1≤k≤s). The Indication-k field 420-$k$ under a tier may specify medical conditions (indications) for which the formulary has been approved (e.g. by Payer 1 410-1 and/or PBM 150) as treatment.

Thus, patient out-of-pocket costs (e.g. coinsurance) may vary depending on one or more of: medical treatment guidelines for a medical condition; available treatment options; the treatment regimen ultimately selected by a patient or HCP 120; the Tier 415 associated with the selected treatment; the Indication 420 for the selected treatment; and Payer 140 and/or PBM 150. However, such out-of-pocket cost information is often difficult to obtain or unavailable to the patient and/or HCP 120 at the time of prescription, which can result in higher ongoing costs to the patient (e.g. if cheaper treatment options are available), and/or may result additional transactions such as a prescription/treatment change, and/or a revisit of the treatment decision by HCP 120 and the patient. Further, when viewed in aggregate, the sub-optimal decisions and/or transactional overhead detrimentally impact overall systemic costs and efficiencies.

As shown in FIG. 3B, DIR 300 may comprise various other data fields including Price 425-$pd$, which may list a price at which a treatment (e.g. drug or device) is being made available. Price 425-$pd$ may be a Payer 140 or PBM 150 provided estimate of patient cost (as seen by Payer 140/PBM 150 based on current patient coverage information). Patient cost (as estimated by Payer 140/PBM 150) may be a function of any unmet deductible, patient copay, coinsurance (e.g. based on Tier 415), cost share (e.g. from Payer 140), and the negotiated price of the drug/device (e.g. between Payer 140/PBM 150 and PMDP 120/Pharmacy 160). As outlined above, for a specific payer and treatment, Tier 415 may depend on indication 420 associated with the treatment. As another example, Price 425-$pd$ may reflect the negotiated price (e.g. with PMDP 120 and/or Pharmacy 160 and/or another entity), and additional cost breakdown (g. copay 421, deductible 423, information may be provided in relation to patient out-of-pocket cost.

In some situations, formulary 405 (including sub-fields) and related information may be obtained (e.g. from Payer 140 and/or PBM 150 and/or another entity such as a health exchange) as formulary sub-block 480. In some embodiments, a portion of sub-block 480 such as Price 425, Co-pay 421, Deductible 423, and Coinsurance 429 may be obtained (e.g. from Payer 140 and/or PBM 150) along with updated formulary 405 during a transaction and/or prior to transaction finalization. Thus, information in sub-block 480 may be current (or made current/updated) at transaction time. Data fields Price 425, Co-pay 421, Deductible 423, and Coinsurance 429 (e.g. which may be part of one or more sub-blocks 480) may be provided for corresponding drugs/devices 302 based on coverage related information 272 and/or plan ID 270 received from HCP 120 (e.g. as part of sub-block 280).

In some instances (e.g. when sub-block 280 does not include coverage related information 272 and/or plan ID 270), Payer 140 and/or PBM 150 and Payer 140 and/or PBM 150 may determine Price 425, Co-pay 421, Deductible 423, and Coinsurance 429 and provide the information to PMDP 130 in sub-block 480. For example, Payer 140 and/or PBM 150 may determine Price 425, Co-pay 421, Deductible 423, and Coinsurance 429, and/or other information in sub-block 480 by using transaction ID 695 and transaction type to correlate the request for information from PMDP 120 with prior information (e.g. in sub-blocks 280 and/or 284) received from HCP 120.

In some embodiments, PMDP 130 may use information in block 480 including Price 425-*pd*, Co-pay 421-*pd*, Deductible 423-*pd*, and Coinsurance 429-*pd* to determine Payment Assistance 391-*pd* for a drug/device (e.g. specified by Drug/Device ID field 302-*pd*). PMDPs 130 may often provide Payment Assistance 391-*pd* (e.g. for a drug/device manufactured and/or supplied by PMDP 130) to increase affordability and/or to offset patient out-of-pocket costs. The payment assistance provided by PMDP 130 (or on behalf of PMDP 130) may be based on various patient eligibility criteria. Accordingly, an updated patient cost breakdown may be provided along with Cost Metrics 395 for the prescription. The updated patient cost breakdown may include for a corresponding drug/device 302-*pd*: (a) a patient out of pocket cost Out of Pocket 392-*pd*; (b) Payment Assistance 391-pd, (c) Pharmacy ID 394-*l* at which the out of pocket cost in (a) above is applicable, and (d) one or more other optional fields.

In some instances (e.g. when a patient wants to avail of payment assistance), upon patient authorization, HCP 120 may provide PII information for a patient along with coverage information (e.g. in sub-block 280), which may be correlated with patient insurance plan information provided by Payer 140 and/or PBM 150 (e.g. in sub-block 480) and patient application information (e.g. which may have been separately provided by the patient to PMDP 130 and/or affiliated entities acting on behalf of PMDP 130) to determine eligibility and Payment Assistance 391-*pd* for a drug/device. Since prescription 250 may comprise multiple drugs/devices, Payment Assistance 391-*pd* may be determined for each corresponding Drug/Device 302-*pd* in prescription 250 for which payment assistance is applicable.

In some embodiments, a PMDP 130 and/or another entity, and/or a user (e.g. patient) application (e.g. running on a mobile device such as a smart phone, handheld computing device, tablet, etc.) may obtain payment assistance information from a plurality of PMDPs 130 to determine cost information 395 associated with each drug/device 302 in a prescription identified by Prescription code 250. For example, the application may aggregate any Payment Assistance 391-pd received from one or more PMDPs 130 (or entities affiliated with the one or more PMDPs 130) to determine cost metrics 395. In instances where an entity payment assistance programs may be coordinated and/or administered by an entity other than PMDP 130 (i.e. by an affiliate, a patient access program provider/coordinator, community agency, non-profit, government, or other entity), then payment assistance information may be provided (e.g. via the application on the patient's mobile computing device) by the administering entity based on information received from each PMDP 130 (e.g. as reflected in sub-block 390). In some embodiments, the application on the patient's mobile computing device may be authorized by an entity (e.g. HCP 120 and/or a patient access program coordinator and/or a Health Exchange and/or PMDP 130) associated with the permissioned blockchain platform and may communicate with the entity authorizing/providing the application via a secure channel to exchange information with entities associated with the permissioned blockchain platform.

Cost information 395 may be based on Patient Criteria 297, which may specify criteria or preferences used to determine cost information 395 (such as locations where the prescription will be filled, preferred pharmacies, etc.). Cost metrics 395 may be at a drug level indicated by 395_*pd* (e.g. cost breakdowns for a specific drug/device 302-*pd*; lowest cost pharmacy at which a specific drug/device 302-*pd* may be obtained, lowest cost drug 302-*pd* in a class 337-*p* over a specified period such as the duration of treatment and/or the duration of coverage), and/or at a prescription level indicated by 395_*p* (e.g. lowest cost to fill a prescription when one or more specific drugs/devices 302 are selected; sets of drugs/devices 302, which, if selected, would provide the lowest cost to fill the prescription; set of drugs/devices 302 that would provide the lowest cost over the duration of treatment for the prescription; set of drugs/devices 302 that would provide the lowest cost over a specified period such as the current insurance/benefits coverage period, etc.)

FIG. 3C shows an example data flow from an initial proposed prescription 250, (which may be part of a first EHR sub-block 280) to alternatives (e.g. in DIR sub-blocks 380 and/or 390) that may be presented to a patient/HCP 120 along with cost information 395 to facilitate treatment selection.

As outlined above, in some embodiments, information pertaining to initial proposed prescription 250 may be obtained (e.g. by PMDP 130 and/or another entity) via a first EHR sub-block 280. EHR sub-block 280 may also include other information (e.g. patient medical coverage information). As shown in FIG. 3C, example proposed prescription 250 may comprise a plurality of first treatments (e.g. proposed drugs/devices 255-*i*, $(1 \le i \le N)$. Sub-block 280 may be encrypted and decryptable by PMDP 130 and/or another authorized entity.

In some embodiments, a drug/device class 337-*p* $(1 \le p \le P)$ may be determined corresponding to one or more drugs/devices 255-*p*, $(1 \le p \le P)$ in proposed prescription 250. As shown in FIG. 3C, drugs/devices 302_*pd* $(1 \le d \le D\_p$, where D_p is the number of selected drugs/devices in class p) corresponding to each drug/device class 337-*p* may be determined.

For each drug/device 302_*pd* in a drug/device class 337-*p*, patient out of pocket cost 392_*pd*, Payment Assistance 391_*pd*, Cost Breakdown 397_*pd*, and Pharmacy information (e.g. Pharmacy ID 394_*l* at which the patient Out of Pocket cost 392_*pd* is applicable, etc.), and Cost information 395_*pd* (at the level of drug 302_*pd*) may be determined. Cost information 395_*pd* may be determined based on patient coverage information and/or information received from PBM 150 and/or Payer 140 and/or another entity. In some embodiments, Pharmacy ID 394_*l* may be determined based on patient criteria 297 (e.g. provided in block 280). The Pharmacy ID 394_*l* may include and/or be used to look up pharmacy related information. In some embodiments, the information above may be provided to HCP 120, a patient, and/or another entity. For example, the information above may be encrypted in sub-block 390 and may be decrypted and read by an authorized receiving entity. As one example, HCP 120 and/or a patient may receive the above information in an application running on a smart phone or other mobile computing device.

In some embodiments, the cost information for drugs/devices 302_*pd* may be aggregated based on based on one or more user (e.g. patient) specified criteria to determine cost metrics 395_*p* (at the level of prescription 255_*p*). As one example, the (potential) cost information 395-*p* at the prescription level may be based, for example, by assuming that a drug/device 302-*pd* and/or one or more drugs/devices 302 may be selected.

As another example, the cost information associated with a potential equivalent prescription may be analyzed to determine cost metrics 395_p such as the lowest total cost to satisfy the potentially equivalent prescription at a single pharmacy within some threshold distance of a location (e.g. current or provided location). As a further example, the cost information associated with a potential equivalent prescription may be analyzed to determine cost metrics 395_p such as the lowest total cost for the potential prescription within some threshold distance of a location (e.g. a current location or provided location such as a zip code or address) without regard to the number of pharmacies used to fulfill the prescription. As an additional example, the cost information associated with a potentially equivalent prescription may be analyzed to determine cost metrics 395_p so that the total cost of the prescription within some threshold distance of a location (e.g. a current location or provided location such as a zip code or address) is within some user-specified threshold of the lowest cost prescription while limiting the number of pharmacies used fulfill the prescription. As another example, the cost information associated with a prescription may be analyzed to determine cost metrics 395_p such as the total cost of treatment over an expected treatment duration and/or over some specified time period (e.g. for a current or remaining insurance term). Patient criteria 297 may also specify other considerations such as a preferred pharmacy, mail order options, etc., which may be used when determining cost-metrics, out of pocket costs, etc. For example, if a user specifies that mail order is acceptable, then sub-block may include costs associated with mail order pharmacies in addition to pharmacies 160 within a region.

When DIR block 300 is to be added to a DIR blockchain, some of the data in a DIR information block 300 may depend on input from, validation by, and/or confirmation by other entities. For example, information in formulary 405 related to a payer (e.g. payer 140 specified in Payer i 410-i) may form part of DIR block 300 and may depend on validation by the payer (e.g. Payer 140). DIR block 300 may be added to the DIR blockchain once validation has been provided and a transaction confirmation has been received. The validation may be obtained in the form of a sub-block (e.g. sub-block 480) from Payer 140. The information in sub-block 480 may be specific to the transaction (e.g. as identified by transaction ID 695), encrypted by Payer 140, and may be decryptable by PMDP 120. In some instances, encrypted sub-block 480 (or information present in sub-block 480) may be intended specifically for PMDP 120 and may not be decryptable by an entity other than PMDP 120.

In some embodiments, for a transaction at a point in time, information in data fields Formulary 405, Payer 1 140-1, tier information in each of the Tier-j fields 415-j associated with the payer in Payer 1 140-1, information in each of the Indication-k fields 410-k associated with each Tier-j field may be part of a sub-block 480 received from Payer 1 140-1. However, information related to any other payers may not form part of sub-block 480 because these payers may not be party to the transaction. Thus, in transactions involving a single payer (e.g. Payer 1 140-1), DIR record 300 may include information (e.g. in sub-block 480) for that specific payer.

When multiple payers are involved in a transaction, then multiple encrypted sub-blocks (e.g. each from a corresponding payer 140-i) may be received by PMDP 130 and integrated by PMDP 130 into DIR record 300. The information in each sub-block received from Payer-i may be private between PMDP 130 and the corresponding Payer-i. Sub-block 480 is merely an example that illustrates some information that may be shared with another specific entity. In general, the information used to form sub-blocks from a data record or block in a locally maintained blockchain (e.g. DIR 300) may depend on regulations (e.g. healthcare and/or privacy), laws governing information sharing (e.g. determining information that can or cannot be shared by entities), business guidelines (e.g. trade secret or sensitive information) and/or contractual obligations (e.g. between or related to the entities sharing information).

Accordingly, in some embodiments, data in a sub-block sent to PMDP 130 may be separately encrypted by the corresponding sending entity (e.g. Payer-i 140-i) and may be decryptable by PMDP 130 and unavailable to unauthorized entities. In some embodiments, encryption of data in a sub-block (e.g. received by PMDP 130) may be based on any appropriate encryption technique including symmetric key cryptography. The encryption may be based, for example, on a secret key shared between the entities (e.g. Payer 140-i, identified in Payer 1 140-1 field and PMDP 130). The receiving entity (e.g. PMDP 130) may be able to decrypt the received sub-block, for example, based on the secret shared key.

Further, prior to being added to a blockchain, data in DIR block 300 may also be separately encrypted by a first entity (e.g. PMDP 130) using any secure encryption technique, so that it is decryptable by and available to the first entity (e.g. PMDP 130) but is unavailable and cannot be viewed by other entities (e.g. HCP 120 and/or Payer 140).

Figure 4:
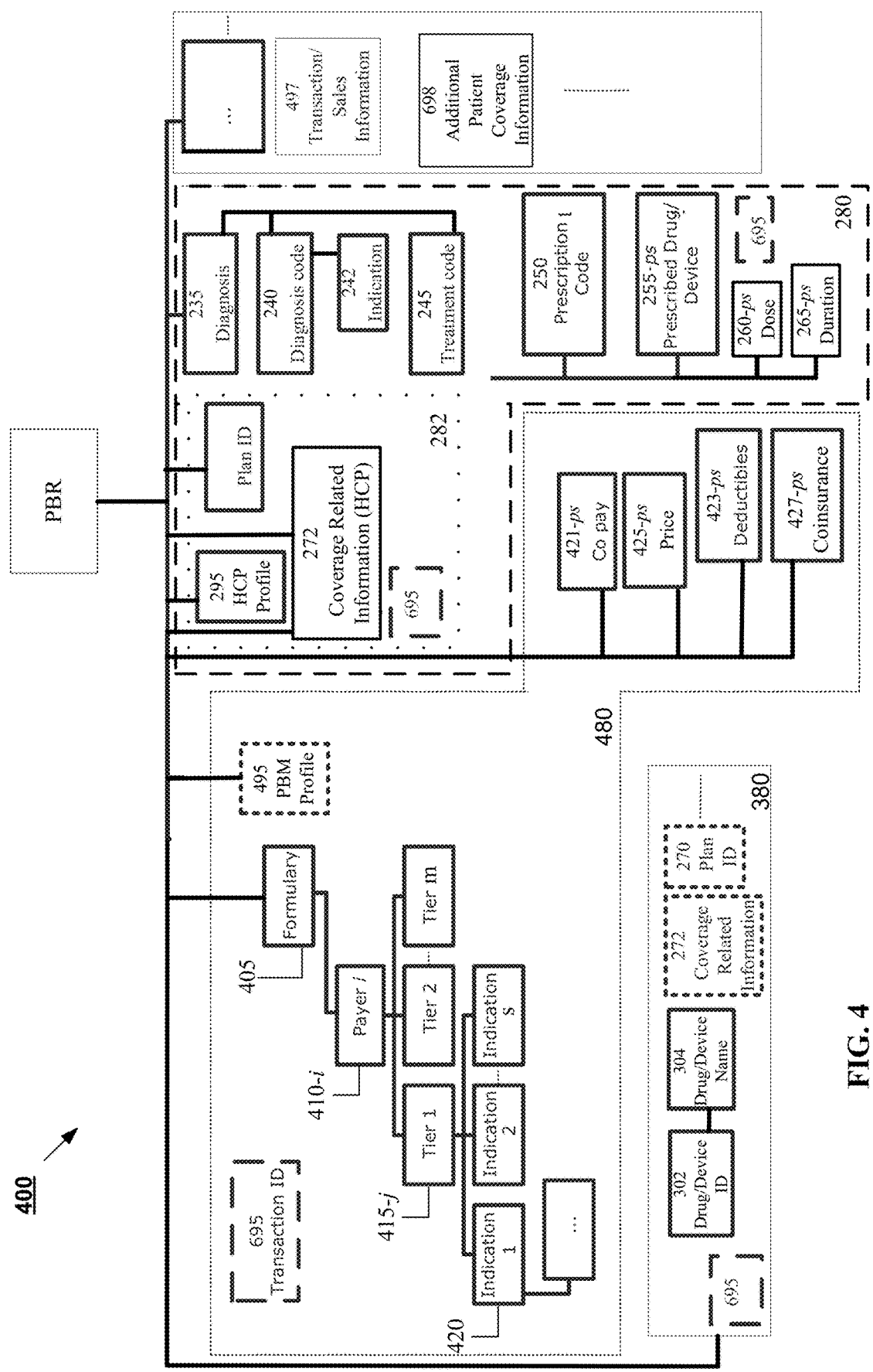
FIG. 4 shows a portion of exemplary Pharmacy Benefits Record (PBR), which may be maintained by a pharmacy benefits manager.

FIG. 4 shows a portion of exemplary Pharmacy Benefits Record (PBR) 400, which may be maintained by PBM 150. The term PBM is used to refer to any entity that serves to administer a portion of benefits (e.g. pharmaceutical and/or medical device prescriptions) on behalf of a payer (e.g. Payer 140). In some instances, PBMs may be affiliated with insurers/payers. In some instances, insurers/payers may administer drug/device benefits directly so that payer 140 and PBM 150 may be viewed as a single entity and portions of the description below may also be applicable to the single (Payer+PBM) entity.

PBR 400 may include information pertaining to payers and associated benefit plans, available benefits, patient/subscriber information, payer drug/device tiers, cost sharing, etc. and may be owned and maintained by PBM 150 (e.g. in PBI database 155). In some embodiments, data fields in PBR 400 may be populated and/or updated by PBM 150 based, in part, on information received from patient/HCP 120 and/or Payer 140 and/or other entities. PBR 400 may also include data received (e.g. as sub-blocks) from other entities. The fields shown in PBR 400 are merely exemplary, and PBR 400 may comprise various other additional fields based on laws, standards, PBM practice, and/or industry practice, etc. A PBR may comprise fields different from (fewer or greater than) those shown in relation to exemplary PBR 400.

PBMs may determine drug tiers for prescribed drugs, which may determine coinsurance amounts. PBMs may also set or determine retail prices for pharmaceutical products, obtain payments or rebates from manufacturers based on the sales volumes of a particular product or a basket of products, and, in some instances, may also obtain post-sale price concessions and payments from pharmacies on formularies. Accordingly, PBR 400 may include Sales Information field 497, which may store transaction and other sales information for each drug. PBR 400 may also include various other fields (not shown in FIG. 4) to track aggregate payer-specific and pharmacy-specific sales volumes for drugs/devices, discount/rebate information, etc. PBM 150 may exchange information (e.g. via encrypted sub-blocks with HCP 120, Payer 140 and/or Pharmacy 160 and/or PMDP 130).

In some embodiments, PBR 400 may be associated with PBM Profile field 495, which may store information pertaining to PBM 150 (e.g. PBM identification, contact information, address, etc.). In some embodiments, some or all of the information in PBM Profile 495 may be optionally shared with other entities in connection with a transaction. For example, a portion of PBM Profile 495 may be sent to one or more entities such as PMDP 130, Payer 140, and/or Pharmacy 160 (e.g. as part of an encrypted sub-block, which may be decryptable by the designated receiving entity).

As shown in FIG. 4, PBR 400 may include a portion the information in sub-block 280 (shown enclosed in a dashed boundary). In some embodiments, some the information in sub-block 280 may be received from HCP 120 and updated and/or validated by PBM 150. In some embodiments, PBM 150 may receive some or all of the information in sub-block 280 (e.g. indirectly) from PMDP 130. In some embodiments, sub-block 280 may include some or all of the information in sub-blocks 284 and/or 284.

Accordingly, as shown in FIG. 4, in some embodiments, the one or more encrypted sub-blocks 280, may include coverage related information 272 (e.g. based on information initially obtained by HCP 120), diagnosis 235, diagnosis code 240, indication 242, diagnosis code 240, treatment code 245, and prescription code 250. Further, PBR 400 may also include one or more of: actual prescribed drugs/devices 255-$ps$ (e.g. corresponding to selected drug/devices 302-$pd$ from drug/device classes 337-$p$), dose 260-$ps$, and/or duration 265-$ps$ along with transaction ID 695 to PBM 150, where $1 \leq p \leq P$, and for each drug/device class p, $1 \leq s \leq D\_p$. Prescription code in sub-block 280 and associated prescribed drugs/devices 255-$ps$, dose 260-$ps$, and/or duration 265-$ps$, etc. may represent a selection of drugs/device (e.g. selected by a patient and/or prescribed by HCP 120) after evaluation of the drugs/devices 302-$pd$. For example, HCP 120 and/or a patient (in consultation with HCP 120) may select one drug/device 302-$ps \equiv 255$-$ps$ from each drug/device class 337-$p$ and the selected drugs/devices 255-$ps$ may be associated with a final/selected prescription 250-$s$. PBM 150 may incorporate some or all of the information in sub-block 280 into PBR 400 (e.g. at the time of transaction confirmation/finalization). Transaction ID 695, which may uniquely identify transactions between entities, may facilitate information exchange and coordination between entities. For example, a unique transaction ID 695 shared between entities that are parties to a transaction may be used to correlate, aggregate, validate, and process information received from one or more entities with locally stored information and/or with information received from other entities. In some embodiments, the finalized prescription 250-$s$ (e.g. in a second sub-block 280 from HCP 120) may be sent subsequent to DIR sub-blocks 380 (with drugs/devices 302-$pd$).

PBR 400 may also include a portion the information in sub-block 380, which may be received from PMDP 130 along with transaction ID 695. For example, in some embodiments, PMDP 130 may send (e.g. in one or more encrypted sub-blocks 380) drug/devices 302-$pd$ corresponding to drug/device classes 337-$p$ (where each drug/device class 337-$p$ may be associated with at least one prescribed drug 255-$p$ (e.g. in an initial prescription 250 sent to PMDP 130). PBR 400 may further include drug/device Name 304-$pd$ (which may be received as part of sub-block 380) corresponding to drugs/devices 302-$pd$. PBM 150 may process the information in sub-block 380 and return a list of approved drugs, tiers, costs, etc. (e.g. in sub-block 480)

In some embodiments, Transaction ID 695 may be used by PBM 150 to determine that sub-blocks 282 and 380 are associated with the same transaction. PDM 150 may then use coverage related information 272 in sub-block 280 to determine the information (e.g. Formulary, Triers, etc.) in in sub-block 480. In some embodiments, sub-block 380 may also include Plan ID 270 and Coverage related information 272 (e.g. when provided to PMDP 120), which may be used by PBM 150 determine information in sub-block 480. For example, PBM 150 may use coverage related information 272 (for a patient and a payer 140-$i$) along with Additional Patient Coverage information 495 (which may be locally maintained and/or obtained from Payer i 410-$i$) to determine information in sub-block 480.

As shown in FIG. 4, sub-block 280 in PBR 400 may include for Payer 140-$i$ (e.g. determined based on coverage information 272 and/or Plan ID 270) and drugs/devices 302-$pd$ (e.g. determined based on sub-block 380): formulary 405, including tier information 415-$j$, and indications 420-$k$.

In some embodiments, sub-block 480 may further include one or more of: diagnosis 235, diagnosis code 240, indication 242, treatment code 245, prescription code 250, prescribed drugs/devices 255, corresponding doses 260, and/or durations 265 (e.g. determined based on sub-block 280). PBR 400 may also include transaction ID 695. PBM 150 may incorporate some portion of the information in sub-blocks 280 and/or 380 into PBR 400 (e.g. at the time of transaction confirmation/finalization).

In some embodiments, PBM 150 may further include (e.g. as part of sub-block 480) various other data fields including Price 425, which may list a price at which a treatment (e.g. drug or device 302-$pd$) is being made available (per plan, tier, and indication information). Price 425-$pd$ may be a Payer 140 or PBM 150 provided estimate of patient cost (as seen by Payer 140/PBM 150 for a drug/device 302-$pd$, or the negotiated price (e.g. as negotiated with PMDP 120 and/or Pharmacy 160 and/or another entity). In some embodiments, an additional cost breakdown (g. copay 421-$pd$, deductible 423-$pd$, coinsurance 427-$pd$, patient out-of-pocket cost for the drug/device 302-$pd$ may be provided as part of sub-block 480.

As outlined above, information in sub-blocks received or sent by PBM 150 may be encrypted. The received sub-blocks may be decrypted by PBM 150, when intended for PBM 150, while sub-blocks transmitted by PBM 150 may be decryptable by the intended recipient.

Figure 5:
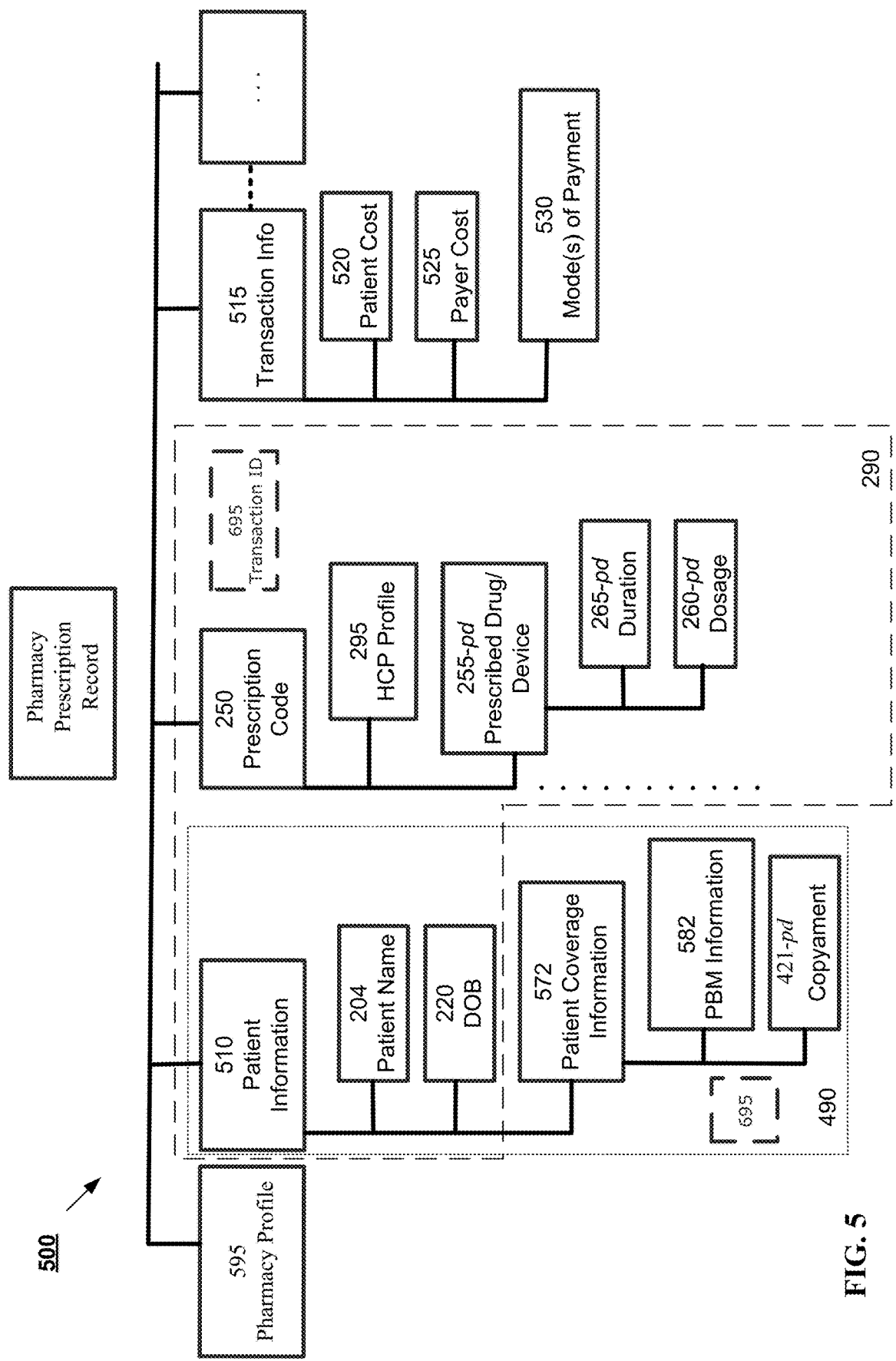
FIG. 5 shows example Pharmacy Prescription Record, which may be maintained by an entity such as a pharmacy.

FIG. 5 shows example Pharmacy Prescription Record (PPR) 500, which may be maintained by an entity such as Pharmacy 160. Pharmacies refer to any entity (physical, virtual, or mail order) that fulfills prescriptions written by a medical provider such as HCP 120. Pharmacies may receive prescriptions from HCPs 120, validate patient coverage information with Payers 140 and/or PBMs 150, and interact with patients to fulfill prescriptions and receive payment from the patient (e.g. based on coverage by collecting one or more of: negotiated prices for drugs/devices, copayments, deductibles, coinsurance, etc.) in accordance with any contract and/or payment arrangements with Payer 140/PBM 150.

In some embodiments, PPR 500 may be owned and maintained by Pharmacy 160 (e.g. in PPI database 165). In some embodiments, data fields in PPR 500 may be populated and/or updated by Pharmacy 160 based, in part, on information received from patient/HCP 120 and/or Payer 140 and/or other entities. PPR 500 may also include data received (e.g. as sub-blocks) from other entities. The fields shown in PPR 500 are merely exemplary, and PPR 500 may comprise various other additional fields based on laws, standards, pharmacy practice, and/or industry practice, etc. A PPR may comprise fields different from (fewer or greater than) those shown in relation to exemplary PPR 500.

In some embodiments, PPR 500 may include Pharmacy Profile field 595, which may store information pertaining to pharmacy 160 (e.g. pharmacy identification, contact information, address, etc.). In some embodiments, some or all of the information in pharmacy profile 595 may be optionally shared with other entities in connection with a transaction. For example, a portion of pharmacy profile 595 may be sent to one or more entities such as PMDP 130, Payer 140, and/or Pharmacy 160 (e.g. as part of an encrypted sub-block, which may be decryptable by the designated receiving entity) and/or shared with a patient.

In some embodiments, PPR 500 may include Patient Information field 510, which may include sub-fields Patient Name 204, DOB 220, Patient Coverage Information 572, PBM Information 582, and Patient Copayment 421-*pd*. PPR 500 may also include Prescription Code 250 for a prescription 255-*p*, HCP profile 295 (e.g. a health care provider ID, registration number, contact information etc.) associated with the prescribing entity for prescription 255-*p*, prescribed drugs/devices 255-*ps* associated with prescription 255-*p*, duration 265-*ps*, and dosage 260-*ps*. In some embodiments, PPR 500 may include various other fields (not shown in FIG. 5) such as prescription date(s), fulfillment status (e.g. whether ready for pickup, picked up and/or delivered to patient, etc.).

In some embodiments, Patient Information 510 (including sub-fields Patient Name 204, DOB 206, portions of Patient Coverage Information 572, Prescription Code 250, Prescribed drugs/devices 255-*ps*, duration, dosage, and HCP profile information may be received by Pharmacy 160 from HCP 120 as encrypted sub-block 290 decryptable by Pharmacy 160 upon finalization of a prescription. For example, HCP 120 and/or patient may select one drug/device 255-*ps* form each drug/device class 337-*p*, and provide the selected drugs/devices 255-*ps* to pharmacy 160 as part of sub-block 290.

In some embodiments, upon receiving and decrypting sub-block 290, Pharmacy 160 may use patient coverage related information (e.g. coverage related information 272, which may be received as part of sub-block 290) to determine a PBM and/or Payer associated with the prescription.

In some embodiments, pharmacy may send some or all of the information in sub-block 290 to Payer 140 and/or PBM 150 (e.g. in accordance with any prevailing regulations). The information sent by Pharmacy 160 to Payer 140 and/or PBM 150 may be in the form of an encrypted sub-block (not shown in FIG. 5) decryptable by the designated entity (e.g. Payer 140 and/or PBM 150). In response, Pharmacy 160 may receive and decrypt encrypted sub-block 490 from Payer 140 and/or PBM 150. Sub-block 490 may include validation information (e.g. in relation to patient coverage), which may be used by Pharmacy 160 to validate and update patient coverage information 572, and to update PBM information 582. In some embodiments, PBM 150 and/or Payer 140 may further include co-payment information 421-*ps* for prescribed drugs/devices 255-*ps* associated with prescription 250-*s*.

In some embodiments, PPR 500 may further include Transaction information 515, which may store information pertaining the to the transaction such as patient cost 515 (such as coinsurance 421-*ps*—as seen by Pharmacy 160), Payer cost 525 (e.g. amount billed/to be billed to Payer 140 and/or PBM 150), and modes of payment (e.g. used by the patient). For example, in some instances, where PMDP 120 provides patient assistance (e.g. as part of a patient assistance program) with co-payments (or other out-of-pocket patient costs), PMDP 120 (or an entity acting on behalf of PMDP 120) may provide a discount card, discount code, or prepaid card, which may be presented to pharmacy 160 as payment and recorded in mode of payment field 530.

Figure 6:
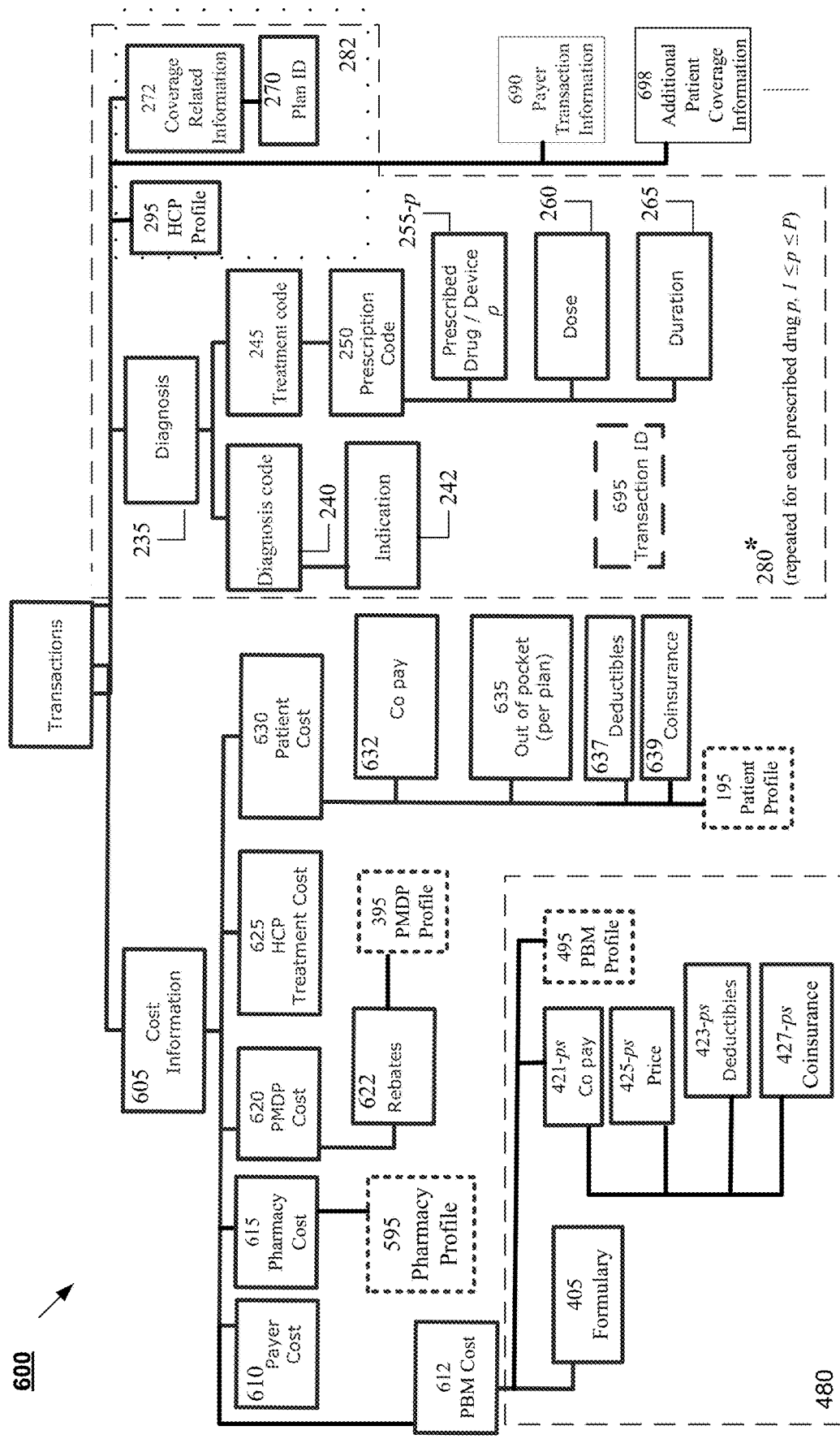
FIG. 6 shows an example Health Transaction Record

FIG. 6 shows an exemplary Health Transaction record (HTR) 600. As shown in FIG. 6, HTR 600 may include treatment and cost related information for a transaction associated with a patient. The fields shown in HTR 600 are merely exemplary, and HTR 600 may comprise various other fields based on laws, standards, industry practice, etc. In addition, an HTR may comprise fields different from (fewer or greater than) those shown in relation to exemplary HTR 600. In some embodiments, HTR 600 may be owned and maintained by entity such as Payer 140 (e.g. health insurer and form part of Transaction Information database 147), which may be responsible for transaction approval and/or payments to one or more entities associated with a transaction.

HTR 600 may comprise various data fields including information about entities associated with and/or authorized to transact with Payer 140 including Patient profile 195, HCP profile 295, PMDP profile 395, PBM profile 495, and Pharmacy profile 595. The stored profiles may include information to effectuate transactions between the entities (e.g. payments, rebates, validations of coverage, authorizations for treatments/prescriptions, etc.)

HTR 600 may include Cost information 605, which may include Payer's view of costs associated with the transaction. For example, Cost information 605 may include Payer cost 610, which may record the net cost to Payer 140 for the transaction. Payer cost 610 may be a function of one or more of: PBM cost 612, Pharmacy Cost 615 (e.g. price charged by Pharmacy 160 to Payer 140), PMDP Cost 620 (e.g. negotiated price between Payer 140 and PMDP 120), rebates 622 (e.g. received by Payer 140 from PMDP 120), HCP treatment cost 625 (e.g. cost for treatment provided by HCP 120 related to the diagnosis), and Patient cost 630 (e.g. patient out of pocket costs 635 as seen by Payer 140 under the plan, which may include patient copayments 632 for the treatment and prescription, deductibles 637, and coinsurance 639). Some of the information associated with Cost information 605 may be available to Payer 140 (e.g. based on contracts etc.), while some cost information 605 may be provided by other entities (e.g. via encrypted sub-blocks decryptable by Payer 140) prior to transaction finalization. For example, PBM cost information 612 may be determined from by decrypting information included in an encrypted sub-block 480, which may be sent by PBM 150 to Payer 140.

As another example, HCP 120 may send encrypted sub-block 282 with coverage related information 272, Plan ID 270 and/or HCP profile 295 to Payer 140. Payer 140 may decrypt the information sub-block 282 and validate patient coverage using additional patient coverage information 698. Validation of patient coverage may be provided to HCP 120 by sending to HCP 120 an encrypted sub-block, decryptable by HCP 120, with the validation information. Some or all of Additional Patient Coverage Information 698 may also be sent (e.g. as an encrypted sub-block, decryptable by PBM 150) to PBM 150 to facilitate validation of patient coverage (e.g. in relation to prescriptions) by PBM 150.

As a further example, encrypted sub-block 280 (which, in some instances, may include information in sub-block 282) may be sent by HCP 120 (e.g. once a prescription has been finalized) to Payer 140 for validation and transaction approval. In some embodiments, encrypted sub-block 280 may be decrypted by Payer 140 and Payer 140 may approve the transaction by sending one or more confirmation messages (e.g. to HCP 120 and/or to other entities).

In some embodiments, upon transaction finalization, EHR 600 may be stored as part of a local blockchain maintained by and accessible to Payer 140. EHR 600, in encrypted form (and decryptable by Payer 140) may also form part of a multi-dimensional block in a multi-dimensional block. Information not in the EHR block 600 of the multi-dimensional blockchain may be encrypted by other entities and may not be decryptable by Payer 140. Conversely, EHR block 600 in the multi-dimensional block may not be decryptable by other entities associated with Payer 140 and/or the platform. Thus, while each entity has a consistent view of the transaction, which is recorded as a multi-dimensional block in a multi-dimensional blockchain, an entity cannot view information in blocks (stored as part of a multi-dimensional block) that are owned by other entities. Accordingly, information in a block (stored as part of a multi-dimensional block) owned a first entity is securely shielded from view by other second entities.

Figure 7A:
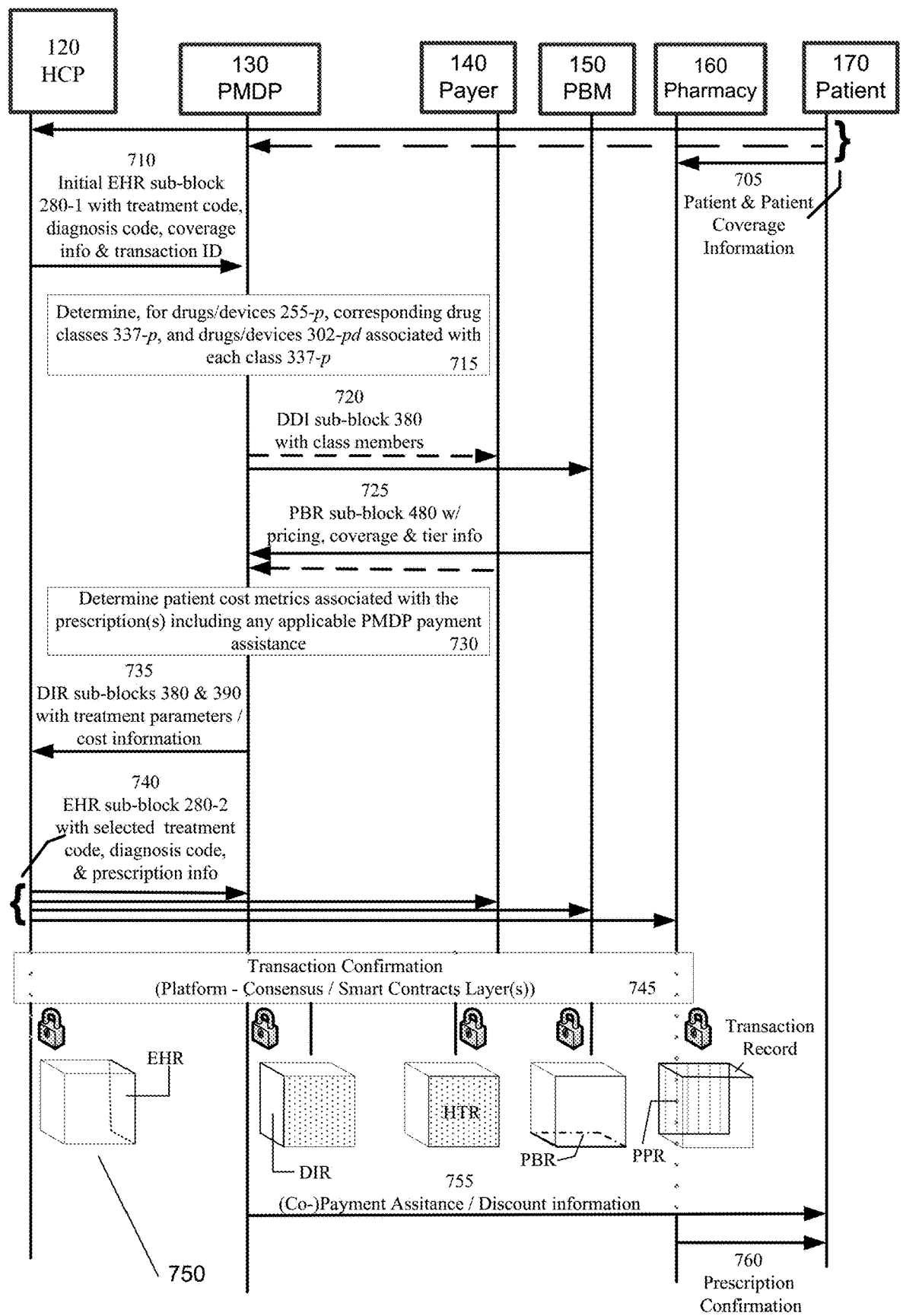
FIG. 7A shows a flow diagram illustrating an example process flow to facilitate healthcare cost determination, healthcare information security and facilitate interoperability between a plurality of entities.

FIG. 7A shows a flow diagram illustrating process flow 700 to facilitate healthcare cost determination, healthcare information security and facilitate interoperability between a plurality of entities. In some embodiments, portions of process flow 700 may occur on a permissioned blockchain platform, which may be made available to subscribing and/or authorized entities. In some embodiments, some or all of flow 700 may be implemented using applications running on computing devices associated with the entities. In flow diagram 700 some routine messages (e.g. patient coverage validation, etc.) have not been shown for ease of description.

As one example, patient 170 may use an application running on a mobile computing device (e.g. smartphone, tablet, laptop, etc.) to initiate a transaction. In some embodiments, the application may be provided and/or authorized by an entity associated with the permissioned blockchain platform. For example, the application (e.g. running on a mobile computing device associated with patient 170) may have been provided by a first entity (e.g. HCP 120, PMDP 130, Health Exchange, and/or a patient access program (not shown in FIG. 7)), and use an Application Programming Interface (API) and/or other network and communication protocols to communicate with the first entity.

In some embodiments, at 705, a patient 170 may provide profile and coverage information to one or more of HCP 120, Pharmacy 160, and optionally to PMDP 130, and/or one or more other entities. For example, patient 170 may provide (or may have previously provided) patient profile and coverage related information to HCP 120 at or prior to the time of obtaining treatment, and/or to Pharmacy 160 at or prior to the time of fulfilling a prescription. In some instances, Patient 170 may have provided patient profile and coverage information to PMDP 130 to participate in and/or to obtain payment assistance. As outlined above, patient profile and coverage information may be provided (or have been) using an application on a mobile device that interacts with and/or is associated with an entity authorized to transact on the permissioned blockchain platform.

In some embodiments, HCP 120 may provide coverage related information 272 and Plan ID 270 to Payer 140 and/or PBM 150 in encrypted sub-blocks 282 (not shown in FIG. 7A), which may be decryptable by the respective receiving entity. Payer 140 and/or PBM 150 may respond with additional encrypted sub-blocks (not shown in FIG. 7A) decryptable by HCP 120 validating patient coverage.

In some embodiments, at 710, HCP 120 may determine diagnosis 235 and may initially provide a corresponding diagnosis code 240 and indication(s) 242, treatment code 245 associated with a treatment for the diagnosed condition, and prescription 250 (e.g. drugs/devices 255-$p$, corresponding doses 260-$p$ each associated with a corresponding duration 265-$p$). In some embodiments, HCP may further obtain or determine a transaction ID 695 (as the initiator of the transaction). In some embodiments, the information outlined above along with patient criteria 297, HCP profile 295, plan ID 270, and, optionally, coverage information 272 may be sent to PMDP 130 as encrypted EHR sub-block decryptable by PMDP 130. For example, coverage information 272 may be sent to PMDP 130 (in EHR sub-block 280), when authorized by patient (e.g. when patient is participating or wants to apply to a payment assistance program associated with PMDP 130).

In some embodiments, in step 715, PMDP 130 may determine, for each drug/device 255-$p$, in prescription 250, a corresponding drug class 337-$p$. Further, PMDP 130 may determine one or more drugs/devices 302-$pd$ associated with each class 337-$p$.

At 720, PMDP 130 may send encrypted DIR sub-block 380 (or a portion thereof) with class members drugs/devices 302-$pd$, along with diagnosis 235 (and related fields such as corresponding diagnosis codes 240 and indication(s) 242, treatment code(s) 245) and transaction ID 695 to PBM 150. DIR sub-block 380 may further include information about each drug/device 302-$pd$ (e.g. as described above in relation to FIGS. 3A-3C). In some situations (e.g. when Payer 140 performs functions of PBM 150 and/or no PBM is used), DIR sub-block 380 may be sent to Payer 140. DIR sub-block may be decryptable by the specified receiving entity.

At 725, PBM 150 (or Payer 140) may respond to PMDP 130 with encrypted PBR sub-block 480, which may include information about formulary 405 for Payer 140, tiers 415-$j$ associated with each drug/device 302-$pd$, pricing information for each drug/device 302-$pd$, including one or more of: copay 421-$pd$, coinsurance 423-$pd$, deductible 423-$pd$, and price 425-$pd$. Sub-block 480 may reference transaction ID 695. For example, PBM 150 (or Payer 140) may determine information in sub-block 480 based on plan information (Plan 1D 270 and/or coverage related information 272) in DIR sub-block 380 and/or by using transaction ID 695 and the transaction type to look up coverage information associated with patient 170. PBR sub-block 480 may be decryptable by PMDP 130.

In step 730, PMDP 130 may decrypt PBR sub-block 480 and use tier 415-$j$ and pricing information (e.g. one or more of: copay 421-$pd$, coinsurance 423-$pd$, deductible 423-$pd$, and price 425-$pd$) for each drug 302-$pd$ along with patient criteria (e.g. location, number of pharmacies, time period, etc.) to determine cost information 395 associated with the prescription. The cost information 395 may take into account any payment assistance to be received by patient (when eligible) through a payment assistance program. In some embodiments, cost metrics 395 may include the cost breakdown 307-$pd$, which may patient out-of-pocket cost for each drug/device 302-$pd$.

In 735 PMDP 130 may send encrypted DIR sub-blocks 380 and 390 with cost information, to HCP 120. DIR sub-blocks 380 and/or 390 may include transaction ID 695, prescription code 250, drug/device classes 337-$p$ corresponding to each drug/device 255-$p$ in the initial prescription (e.g. at 710), drugs/devices 302-*pd* corresponding to each drug/device class 337-*p*.

At 740, HCP 120 may send encrypted sub-blocks 280-2 with transaction ID 695 with a transaction type indicating HCP approval of the prescription to one or more of HCP 120, PBM 130, and/or Payer 140. Encrypted sub-blocks 280-2 may further include selected drugs devices 255-*ps*, where 1≤p≤P, and for each drug/device class p, 1≤s≤D_p. For example, one drug/device 255-*ps* may be selected from each drug/device class 337-*p*. In some embodiments, encrypted EHR sub-block 280-2. Each encrypted EHR sub-block 280-2 may be decrypted by the designated receiving entity. The information in encrypted sub-blocks 280-2 may be similar to sub-block 280 (e.g. in FIG. 2).

At 745, upon approval by Payer 140 and/or PBM 150, the platform (e.g. private permissioned blockchain platform) may send transaction ID 695 and a transaction type indicating transaction confirmation to entities associated with the transaction. Upon receiving the confirmation each entity may add its respective encrypted record (e.g. EHR 200 for HCP 120, DIR record for PMDP 120, PBR form PBM 140, PPR for Pharmacy 160, and HTR for Payer 140) to a local blockchain. In addition, two or more of the above encrypted records may form part of a multi-dimensional block 750 in a multi-dimensional blockchain (not shown in FIG. 7A). An encrypted block (e.g. EHR 200 for HCP 120, DIR 300 for PMDP 120, PBR 400 for PBM 140, PPR 500 for Pharmacy 160, and HTR 600 for Payer 140) in the multi-dimensional block may be decrypted by the entity encrypting the block and may not be decrypted by any other entity. Thus, while each block represents an entity's view of the transaction, the view is consistent with the views of other entities in relation to the same transaction because each block includes (via received sub-blocks) approved information from other related entities at the time of transaction finalization. In addition, while each multi-dimensional block in the multi-dimensional blockchain represents a snapshot of a finalized transaction as seen by entities that are party to the transaction, information in any single encrypted block (e.g. one of EHR 200, DIR 300, PBR 400, PPR 500, or HTR 600 in FIG. 7A) that is owned and encrypted by a specific entity (e.g. one of HCP 120, PMDP 120, PBM 140, Pharmacy 160, or Payer 140, respectively, in FIG. 7A) is shielded from non-owning entities. As shown in FIG. 7A, multi-dimensional block 750 is visualized as a cube (a multi-dimensional volume) with each face of the cube representing a block associated with an entity that is party to the transaction. In the event that the transaction is not approved by PBM 150 and/or Payer 140 and/or another entity, one or more of steps 715 through 740 may be repeated.

At 755, PMDP 130 or the platform may send payment assistance information to patient 170 (e.g. via the application on a mobile computing device associated with the patient). The payment assistance information may take the form of an electronic credit, code, or any other payment type (e.g. virtual debit/credit card, physical debit or credit card, etc.) that may be used to cover some or all of the patient's out-of-pocket costs (e.g. for one or more specific drugs/devices 255-*ps* in the prescription and/or the prescription as a whole).

Figure 7B:
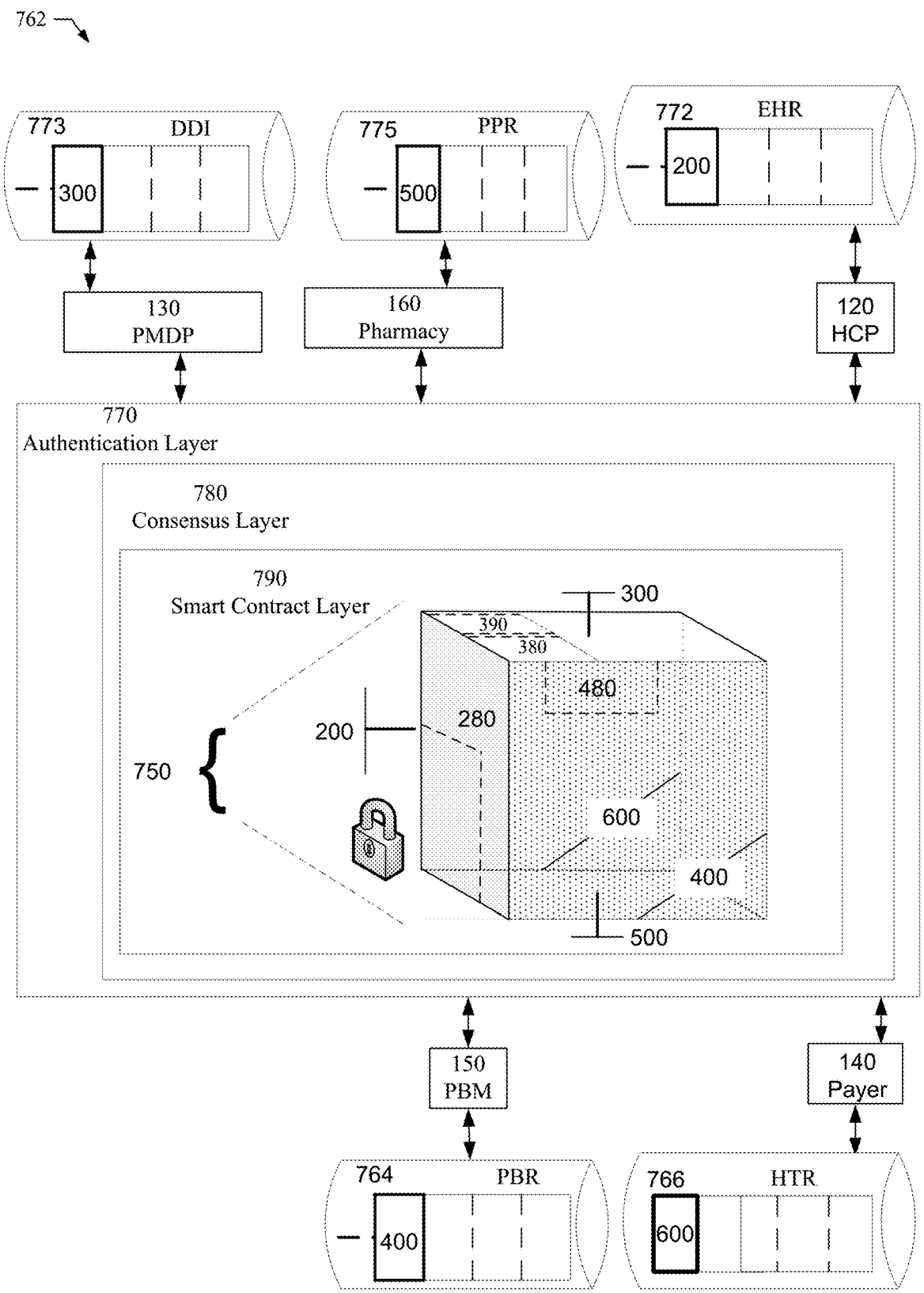
FIG. 7B illustrates entities and layers associated with an example platform to facilitate healthcare system security and interoperability.

In 760, Pharmacy 160 send a prescription confirmation to patient 170 (e.g. via the application and/or any other permissible communication such as a secure text message, secure e-mail, etc.) indicating receipt and/or availability of the prescription. In some embodiments, when obtaining the prescription (e.g. in person, online, etc.), patient 170 may present the payment assistance information to reduce out-of-pocket FIG. 7B depicts entities and layers associated with an example platform to facilitate healthcare system security and interoperability. In some embodiments, the various entities HCP 120, PMDP 130, Payer 140 etc. may form part of a permissioned blockchain platform. In a permissioned blockchain platform, trusted entities may form a platform and invite other trusted entities to join the network. In some embodiments, the permissioned blockchain platform may also be private (e.g. to invited and/or authorized entities). In some embodiments, the permissioned blockchain platform may support multi-dimensional blockchains. Rules pertaining to access and adding blocks to the multi-dimensional blockchain, program code to determine contracts between the entities (e.g. smart contracts), applications that leverage platform functionality (e.g. on behalf of a patient 170), validation of updates, etc. may be determined and/or authorized by entities associated with the permissioned blockchain platform.

In some embodiments, the permissioned blockchain platform may take the form of a cloud-based system. A cloud-based system refers to infrastructure, applications, services, and/or other resources (including hardware resources) that may be made available over a network (e.g. the Internet). Cloud-based systems may be based on underlying hardware and software resources and may be public (e.g. available on a fee basis to all), private (e.g. limited to an organization), or a hybrid (using some combination of public and private clouds). In some embodiments, the entities associated with the platform may be represented by servers (hardware and/or software), which, in some instances, may be cloud based. For example, HCP 120, PMDP 130, and/or Payer 140 may include agents running on servers, and/or agents running on cloud-based platforms including Virtual Machines (VMs).

In some embodiments, access to functionality afforded by the permissioned blockchain platform may be facilitated through a layer or an API associated with the platform. For example, patients 170 and/or another authorized entity acting on behalf of a patient (e.g. an entity facilitating access to payment assistance programs offered by PMDPs 130) may provide a mobile application (e.g. running on a smartphone or other mobile computing device) that interacts with the cloud based permissioned blockchain platform to facilitate: (a) determination of patient choices and associated cost metrics associated with an initial prescription (e.g. as indicated by data in sub-block 280-1 in FIG. 7A) for a patient 170 based on patient criteria 297 and (b prescription finalization (e.g. as indicated by data in sub-block 280-2 in FIG. 7A) in conjunction with the delivery of payment assistance to patient 170.

As shown in FIG. 7B, multi-dimensional block 750 includes EHR information block 200, DIR information block 300, PBR information block 400, PPR information block 500, and HTR information block 600. In some embodiments, multi-dimensional block 750 may form part of a multi-dimensional blockchain. In multi-dimensional block 750, EHR information block 200, DIR information block 300, PBR information block 400, PPR information block 500, and HTR information block 600 may be encrypted and decryptable by HCP 120, PMDP 130, PBM 150, Pharmacy 160, and Payer 140, respectively.

Further, EHR information block 200, DIR information block 300, PBR information block 400, PPR information block 500, and HTR information block 600 may also form blocks in EHR blockchain 772, DIR blockchain 773, PBR blockchain 764, PPR blockchain 775, and HTR blockchain 766, respectively. As shown in FIG. 7B, EHR blockchain 772, DIR blockchain 773, PBR blockchain 764, PPR blockchain 775, and HTR blockchain 766 may be owned and locally maintained by HCP 120, PMDP 130, PBM 150, Pharmacy 160, and Payer 140, respectively. FIG. 7B also depicts sub-blocks 280 (which forms part of EHR block 200), sub-blocks 380 and 390 (which form part of DIR block 300) and sub-block 480 (which forms part of PBR block 400). As outlined above, information in the sub-locks may have been shared between some of the entities associated with a transaction prior to transaction finalization and (at the time of transaction finalization) may be consistent across a plurality of blocks that form part of multi-dimensional block 750. In some embodiments, each field associated with information blocks 200, 300, 400, 500 and/or 600 may have a unique global field id, which may uniquely identify the field within the multi-dimensional blockchain system and/or to relevant entities, when information pertaining to that field is shared between entities. Multi-dimensional blocks may include data and a timestamp. Timestamps may determine the order in which multi-dimensional blocks (once finalized) are linked.

As shown in FIG. 7B, HCP 120, PMDP 130, PBM 150, Pharmacy 160, and Payer 140 may interact with authentication layer 770. Authentication layer 770, may include functionality for identification and management (adding, registering, authorizing, and deleting) of system entities and/or applications (e.g. mobile applications) that use (or request use to) functionality provided by the permissioned blockchain platform. In addition, authentication layer may include functionality to validate permissions related to operations involving: (a) the multi-dimensional blockchain (adding new blocks, creating links, etc.); (b) transaction types (e.g. whether an entity may initiate or participate in a specified transaction type), etc. Authentication layer 770 may interact with consensus layer 780, which may include functionality to determine the ordering of transactions and validate correctness of a set of transactions related to multi-dimensional block 750.

In some embodiments, consensus layer 780 may confirm the correctness of transactions that constitute the multi-dimensional block. At the time of transaction finalization, a consensus technique applied by consensus layer 780 may confirm the correctness of transactions (including shared data between entities) that constitute the multi-dimensional block. In some embodiments, consensus techniques such as Byzantine Fault Tolerance (BFT) or variations thereof such as Redundant BFT, Fast Byzantine Consensus, Dynamic Quorums, or some other voting-based consensus technique may be used to determine if a multi-dimensional block 750 may be formed using component blocks (e.g. EHR information block 200, DIR information block 300, PBR information block 400, PPR information block 500, and HTR information block 600). When an authorized entity (e.g. Payer 140 or a designated authoritative entity for a transaction/transaction type) or some specified number (e.g. all or a majority) of entities validates a transaction or block, then consensus is achieved. Determination of consensus or transaction validation may vary depending on the transaction type.

If the transaction is confirmed as correct by the consensus technique, then a first instance of an unlocked multi-dimensional block 750 may be formed. As shown in FIG. 7B, unlocked multi-dimensional block 750 may be locked and added to the multi-dimensional block when the transaction is finalized. In some embodiments, blocks that form part of multi-dimensional block 750 (e.g. EHR information block 200, DIR information block 300, PBR information block 400, PPR information block 500, and HTR information block 600) may also be added as blocks to respective local blockchains (e.g. EHR blockchain 772, DIR blockchain 773, PBR blockchain 764, PPR blockchain 775, and HTR blockchain 766, respectively) at the time of transaction finalization and upon locking of multi-dimensional block 750. Thus, information in the locally stored block (e.g. EHR information block 200, DIR information block 300, PBR information block 400, PPR information block 500, and HTR information block 600) is also consistent with information in multi-dimensional block 750.

On the other hand, if, for example, a patient identified in Patient ID 425 in sub-block 480 does not match a Patient ID (e.g. in sub-block 280), the transaction may be deemed incorrect and the block addition request may be rejected. In some embodiments, the platform, or each entity may maintain a log of rejected transactions for traceability and debugging purposes. The log may indicate reasons or codes associated with transaction rejection.

In some embodiments, consensus layer 780 may apply consensus techniques and may interact with a smart contracts layer 790 to establish transaction correctness and/or validity and initiate further actions. Smart Contracts layer 790 may comprise program code that implements logic related to a blockchain. For example, "smart contract" program code associated with the multi-dimensional blockchain may process transaction requests and determine the validity of transactions based on program logic. The logic may depend on rules agreed to by the entities for transactions related to the blockchain. For example, Smart Contracts layer 790 may reject a transaction (e.g. from HCP 120) because of incompatibility between two or more drugs prescribed to a patient. Smart contracts may operate at validation time and at commit time before a block is locked and/or committed. In some embodiments, smart contracts layer 790 may encode rules or agreement between two or more entities in relation to data sharing, transactions, etc., which may be based on a real-world contract between the entities. In some embodiments, each update on a traditional blockchain (e.g. one of EHR blockchain 772, DIR blockchain 773, PBR blockchain 764, PPR blockchain 775, or HTR blockchain 766) may be validated by smart contract program code associated with the platform. The smart contract program code may reflect agreements between the entities in relation to data sharing, authentication, payments, etc. The smart contract layer may be viewed as an automation tool that facilitates interaction between entities without manual intervention. In some embodiments, the smart contract layer may initiate actions based on rules associated with one or more contracts when those rules have been satisfied. Each update to the multi-dimensional blockchain, and/or the passage of time, and/or other events and/or specific requests related to a contract (e.g. identified by a contract ID) may trigger actions by the smart contract layer.

The linking of updated records (e.g. updated record 520 and updated record 540) may be performed based on pre-defined rules agreed upon by the entities (e.g. HCP 120 and Payer 140). In some embodiments, the linking of blocks (e.g. updated block 520 and updated block 540) may be performed based on smart contract(s) associated with the multi-dimensional blockchain. After linking updated block 520 and updated blocks 540 may be rehashed. As outlined above, the links may allow an entity to correlate information in its blockchain with information in a blockchain maintained by another entity. In addition, the entities may be able to determine a transaction or transactions associated with information in a specific block maintained by that entity. Accordingly, two or more entities may have a coherent and consistent view of transactions associated with blocks in distinct blockchains. During the process of formation multi-dimensional block 750 may be (at least initially) not fully formed (or a multi-dimensional block in progress)—so that blocks received from other entities may transform the current in progress (not fully formed) multi-dimensional block by adding another dimension. For example, finalized HTR 200 (with a prescription from HCP 120) may be added to current in progress multi-dimensional block as a dimension. Another dimension may then be added to the in progress multi-dimensional block—for example, a dimension with PPR 500 (with the prescription information). The process may continue until the multi-dimensional block is fully formed (e.g. includes dimensions from all relevant parties to a transaction).

Multi-dimensional block (and its component records) may be locked upon transaction finalization to prevent further modifications and ensure a consistent view. Any subsequent modifications may result in a new multi-dimensional block being added to the multi-dimensional blockchain. For example, a new multi-dimensional block may be formed with updates to a data record for a single dimension while substantive information associated with the other dimensions may remain unchanged. For example, drug related information (e.g. new contraindications) associated with a drug prescribed to a patient may be updated (e.g. by PMDP 130) in a new multi-dimensional block without updates to other records.

The multi-dimensional block may take the form of a Merkle tree associated with a multi-dimensional block chain that includes component data records (e.g. EHR 200, DIR record 300, PBR 400, PPR 500 and HTR 600). As outlined earlier, the data records may also be associated with distinct individual blockchains.

Accordingly, cryptographic hashes of individual records (e.g. separate cryptographic hashes (or "hash") of EHR 200, DIR record 300, PBR 400, PPR 500 and HTR 600) in the distinct individual blockchains (772, 773, 764, 775, and 766, respectively) may be obtained using distinct cryptographic hash functions so that records owned by an entity are not decryptable or visible to other entities. Separate cryptographic functions (e.g. which may be known to entities associated with the permissioned blockchain platform) may be used to obtain cryptographic hashes of combinations of records so that a top hash is associated with the multi-dimensional block as a whole. In some embodiments, each multi-dimensional block may include a block header with a timestamp, top hash, information related to the previous block, a pointer to the root of Merkle tree, and other appropriate information. The hash references may take the form of uniform resource locator (URL) on the private permissioned blockchain platform and/or local (entity specific) addresses.

FIG. 7B shows a committed and locked multi-dimensional block 750, where information from sub-blocks 480, 280, 380, and 390 has been shared between corresponding authorized relevant entities. In addition, multi-dimensional block 750 includes linkages between individual component blocks. Multi-dimensional block 750 may represent a holistic view of transaction at a point in time, in part, because it may include real world physical states associated with a drug (dosage, effects, etc.), a patient (medical condition, treatment, effect, etc.), and cost at that point in time. Multi-dimensional block 750 may also include links to a previous block in the blockchain. Validated and finalized multi-dimensional block 750 may include finalized data records 200, 300, 400, 500 and 600, which may correspond to finalized information blocks 200, 300, 400, 500, and 600, respectively, in corresponding distinct local blockchains 772, 773, 764, 775, and 766, respectively.

Figure 8:
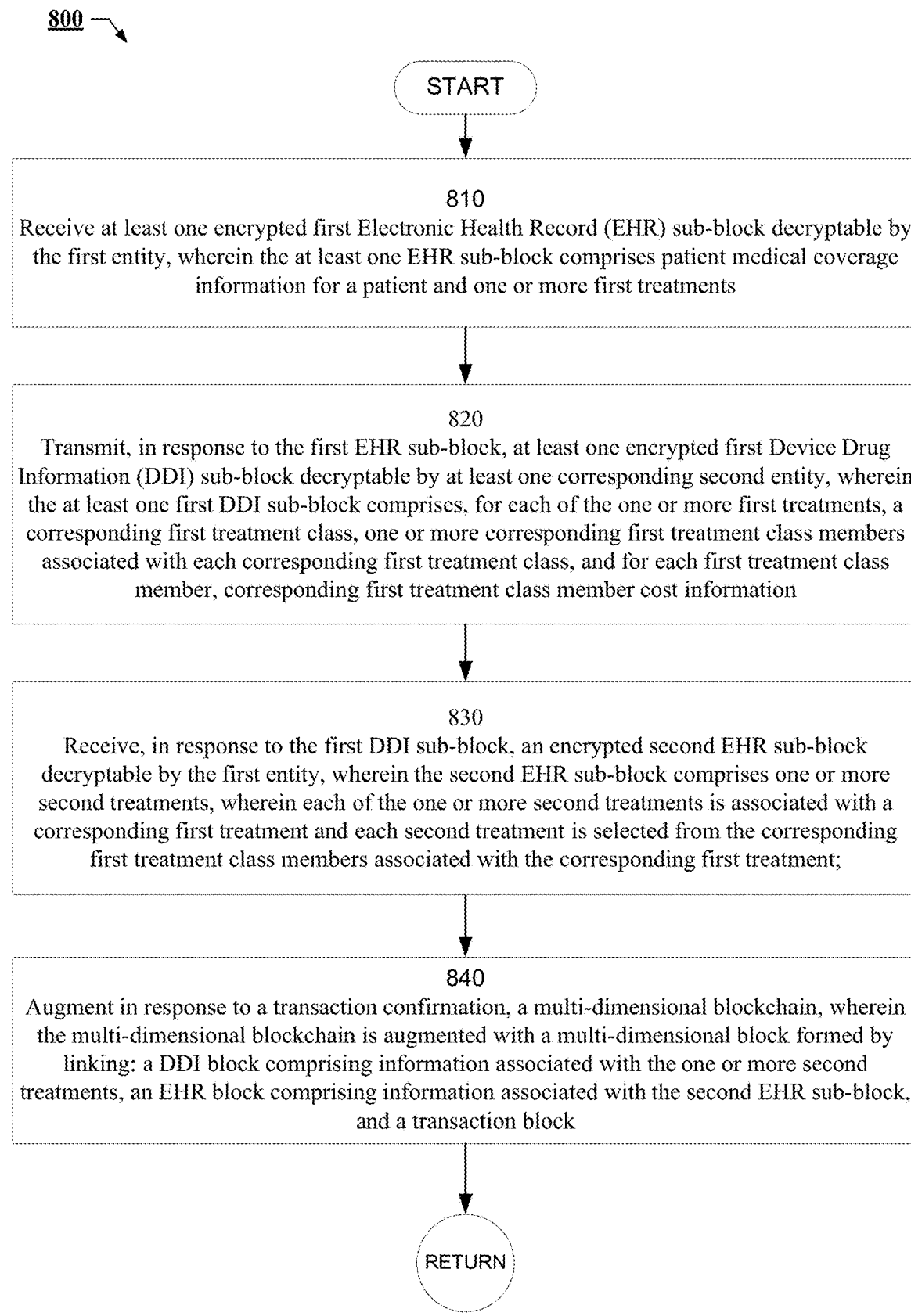
FIG. 8 shows a flowchart of an exemplary method to facilitate healthcare information security and interoperability while facilitating patient treatment selection and transparency in treatment costs.

FIG. 8 shows a flowchart of an exemplary method 800 to facilitate healthcare information security and interoperability while facilitating patient treatment selection and transparency in treatment costs. In some embodiments, method 800 may use multi-dimensional blockchains, which may be based on distinct blockchains maintained by the individual entities in a system. In some embodiments, method 800 may be performed (at least in part) on a private permissioned blockchain platform, which, in some instances, may take the form of a cloud-based system. Method 800 may also be performed by a processor, computer or networks of computers such as distributed computing systems, servers (hardware and software), including application servers, mobile computing devices (e.g. smartphones, smart wearable devices, handheld computers, tablets, laptops, etc.), as well as cloud-based systems.

In some embodiments, method 800 may be performed at a first entity. For example, the first entity may comprise at least one server or a computer system associated with at least one of a pharmaceutical provider or a medical device provider such as PMDP 130. In some embodiments, the first entity may interact with one or more second entities. The second entities may include one or more servers or computer systems associated with healthcare providers such as HCP 120, PBMs 150, Pharmacies 160, or insurance providers such as Payer 140, or patients 170. In some embodiments, the first entity and the one or more second entities may form computing nodes in a distributed computing system and the multi-dimensional blockchain may form part of a permissioned private blockchain platform such as permissioned private blockchain platform.

In some embodiments, method 700 may be invoked when an entity such as the first entity initiates a transaction (e.g. with a transaction ID and/or transaction type) to add a block to locally maintained blockchain. The addition of the block to the local blockchain may involve inputs from one or more other entities and the permissioned private blockchain platform may invoke method 800.

In some embodiments, in step 810, a first entity may receive at least one encrypted first Electronic Health Record (EHR) sub-block (e.g. sub-block 280-1) decryptable by the first entity, wherein the at least one EHR sub-block comprises patient medical coverage information for a patient and one or more first treatments (prescription 250 with drugs/devices (first treatments) 255-$p$, $1 \le p \le P$). For example, the one or more first treatments may include drugs D1, D2, D3, and D4.

In step 820, the first entity may transmit, in response to the first EHR sub-block, at least one encrypted first Device Drug Information (DIR) sub-block (e.g. DIR sub-block 390) decryptable by at least one corresponding second entity (e.g. HCP 120), wherein the at least one first DIR sub-block comprises, for each of the one or more first treatments (255-$p$), a corresponding first treatment class (337-$p$), one or more corresponding first treatment class members (302-$pd$, $1 \le d \le D\_p$) each associated with the corresponding first treatment class, and for each first treatment class member (302-$pd$), corresponding first treatment class member cost information (395, 397-$pd$).

For example, the first treatment class may comprise classes C1, C2, C3, and C4 corresponding to drugs D1, D2, D3, and D4, respectively. Further, each class may include members as outlined below: C1={D11, D12}; C2={D21}; C3={D31, D32, D33, D34}; and C4={D41, D42, D43}, where D1εC1, D2εC2, D3εC3, and D4εC4. Cost information may be provided for each class member (e.g. individually as in cost breakdown 397-pd and in the aggregate as in cost metrics 395).

In step 830, the first entity may receive, in response to the first DIR sub-block, an encrypted second EHR sub-block (e.g. sub-block 280-2) decryptable by the first entity, wherein the second EHR sub-block comprises one or more second treatments (e.g. treatments 255-ps selected from treatments 302-pd), wherein each of the one or more second treatments (255-ps) is associated with a corresponding first treatment (302-pd) and each second treatment (255-ps) is selected from the corresponding first treatment class members (337-pd) associated with the corresponding first treatment (255-p); For example, the second treatments may include second treatments D12, D21, D31, and D43 selected from classes C1, C2, C3, and C4, respectively, where second treatments D12, D21, D31, and D43 are associated (e.g. via classes C1, C2, C3, and C4, respectively) with corresponding first treatment class members (D1, D2, D3, and D4, respectively) in the first treatment (e.g. initial prescription). In some embodiments, the one or more second treatments in the second EHR block may be based on patient-specific cost metrics.

In block 840, the first entity may augment a multi-dimensional blockchain, wherein the multi-dimensional blockchain is augmented with a multi-dimensional block (e.g. multi-dimensional block 750) formed by linking: a DIR block (e.g. DIR block 300) comprising information associated with the one or more second treatments, an EHR block (e.g. EHR block 200) comprising information associated with the second EHR sub-block (e.g. sub-block 280-2), and a transaction block (e.g. HTR 600). In some embodiments, the transaction block may comprise a prescription for the second treatment at the specified location at a specified patient cost.

In some embodiments, upon receiving the first EHR sub-block (e.g. in step 810), the first entity may: determine, for each of the one or more first treatments (255-p—e.g. D1, D2, D3, and D4), the corresponding first treatment class (337-p—e.g. classes C1, C2, C3, and C4, respectively), wherein each corresponding first treatment class comprises one or more corresponding first treatment class members (302-pd-members of C1, C2, C3, and C4, which include at least D1, D2, D3, and D4, respectively). Further, the first entity may determine, for each corresponding first treatment class (337-p—e.g. C1, C2, C3, and C4), one or more corresponding first treatment class member cost information ((e.g. individually as in cost breakdown 397-pd for each drug in C1, C2, C3, and C4 and/or in the aggregate as in cost metrics 395) for the one or more corresponding first treatment class members associated with the first treatment class.

In some embodiments, the first EHR sub-block (e.g. 280-1) may comprise patient-specific parameters (e.g. including patient criteria 297) and the at least one treatment class is determined based on the patient-specific parameters. The patient-specific parameters may include one or more of: patient co-morbidity information; route of administration information (335-pd), safety (330-pd) and efficacy (337-pd) information; and/or patient location information.

In some embodiments, for each first treatment (255-p), the corresponding first treatment class (337-p) and the corresponding first treatment class member cost information (395, 397-pd) for each treatment class member (302-pd) may be determined based on the patient medical coverage information. For example, the cost information may be determined based further on one or more of: (a) providers (e.g. pharmacies 160) located within a specified distance of a patient location, wherein location information for the patient is comprised in the first EHR sub-block (e.g. coverage related information 272 and/or a portion of patient profile 230 in sub-block 280, which may include information in sub-blocks 282 and/or 284); and/or (b) a patient specific out-of-pocket cost (corresponding to each corresponding first treatment class member (302-pd) for a corresponding treatment unit (e.g. dose and/or duration); and/or (c) a patient-specific estimated total out-of-pocket cost (392-pd) corresponding to each corresponding first treatment class member (302-pd) for a typical treatment duration; and/or (d) a patient-specific estimated total out-of-pocket cost corresponding to each corresponding first treatment class member (302-pd) for the remaining duration (e.g. till the date that current patient coverage ends) of a medical coverage plan associated with the patient.

In some embodiments, upon receiving the second EHR sub-block (e.g. in step 830), the first entity may determine payment assistance information for at least one of the one or more second treatments; and transmit the payment assistance information with a transaction confirmation to a patient. In some embodiments, upon receiving the second EHR sub-block (e.g. in step 830), the first entity may transmit a transaction confirmation comprising at least one prescription for the one or more second treatments along with payment assistance information to the patient.

The payment assistance information may take the form of an electronic credit, code, or any other payment type (e.g. virtual debit/credit card, physical debit or credit card, etc.) that may be used to cover some or all of the patient's out-of-pocket costs (e.g. for one or more specific drugs/devices 255-ps in the prescription and/or the prescription as a whole). Thus, in some instances, the payment assistance information may include an actual monetary payment to patient 170 and/or to pharmacy 160. For example, in some instances, the payment assistance may specify a drug and/or pharmacy (or a pharmacy company), where the payment assistance may be used.

Figure 9:
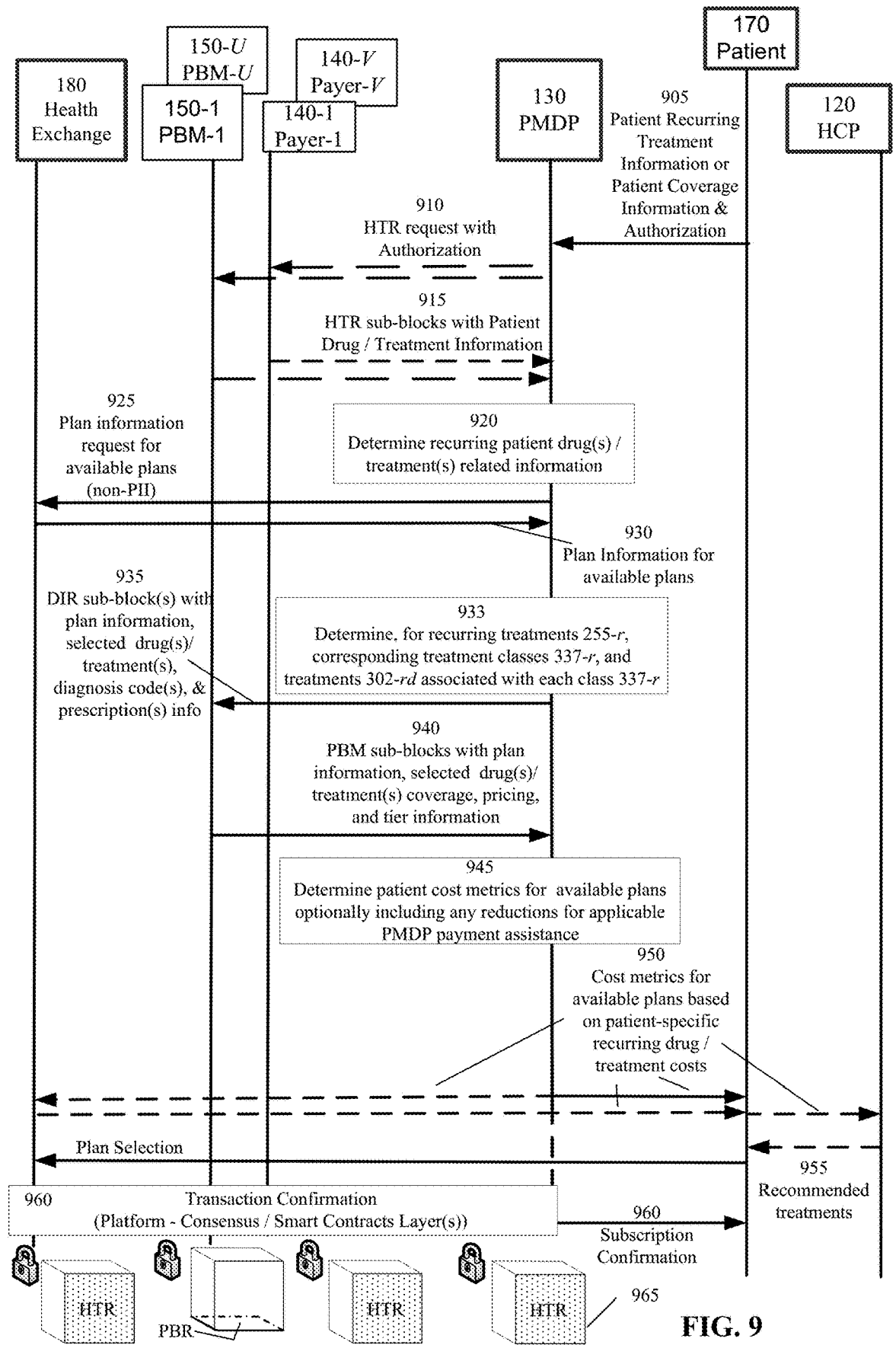
FIG. 9 shows a flow diagram illustrating an example process flow to facilitate healthcare insurance selection and cost determination, while maintaining healthcare information security and facilitating interoperability between a plurality of entities.

FIG. 9 shows a flow diagram illustrating process flow 900 to facilitate healthcare insurance selection and cost determination, while maintaining healthcare information security and facilitating interoperability between a plurality of entities. In some embodiments, portions of process flow 900 may occur on a permissioned blockchain platform, which may be made available to subscribing and/or authorized entities. In some embodiments, some or all of flow 700 may be implemented using applications running on computing devices associated with the entities. In flow diagram 900 some routine messages have not been shown for ease of description.

As one example, patient 170 may use an application running on a mobile computing device (e.g. smartphone, tablet, laptop, etc.) to initiate a transaction. In some embodiments, the application may be provided and/or authorized by an entity associated with the permissioned blockchain platform. For example, the application (e.g. running on a mobile computing device associated with patient 170) may have been provided by a first entity (e.g. HCP 120, PMDP 130, and/or a patient access program (not shown in FIG. 9)), and use an Application Programming Interface (API) and/or other network and communication protocols to communicate with the first entity. In some embodiments, patient 170 may invoke an application that communicates with an entity such as PMDP 130 (as shown in FIG. 9), or a patient assistance program, patient access program, etc. associated with the permissioned blockchain platform. Thus, in some embodiments, the application may act on behalf of an entity (e.g. PMDP 130) and valid and authorized transactions, communications etc. related to the application may appear as if the entity (e.g. PMDP 130) was performing the transaction or may be forwarded (after authorization, validation, and appropriate processing/encoding) by the entity (e.g. PMDP 130).

For the purposes of the description below, PMDP 130 has been used as an example. However, process flow 900 may also be practiced by other entities such as a patient assistance program, and/or patient access program, which may assist patients 170 to obtain health coverage and/or qualify for patient assistance. As outlined above, the application (e.g. used by patient 170) may act on behalf of an entity in a manner transparent to patient 170. Thus, in some instances, actions indicated as being performed by patient 170 in FIG. 9 may occur through and/or be attributed to another entity (e.g. PMDP 130). In some embodiments, a private entity that offers a choice of several insurance plans may offer an application implementing process flow 900 to potential subscribers (e.g. shown as patients 170 in FIG. 9) to facilitate selection of appropriate coverage.

In many situations, patients often need or use treatments (drugs, devices, and/or procedures) recurrently. The term recurring treatment is used herein to refer to medications, devices, and/or procedures that have been prescribed to a patient for a medical condition that is present (ongoing), and/or chronic, and/or likely to occur, and/or will recur/manifest itself (e.g. without the recommended treatment) over an extended period (e.g. several weeks, months, or years). For example, various conditions (e.g. diabetes, blood pressure, heart disease, kidney disease requiring dialysis, etc. and/or other chronic conditions) may require extended periods over which a treatment is applied or prescribed. In these situations, a drug (e.g. medications), device (e.g. drug delivery device), or treatment (e.g. physiotherapy, dialysis, etc.) may be used and/or prescribed repeatedly over an extended period. However, at the time of insurance plan selection, patients typically do not have information about how total medical costs (premiums paid to the plan, deductibles paid, copayments paid, coinsurance paid, less any payment assistance received) are affected by a plan selection and/or drug/device selection. In some embodiments, some disclosed embodiments, which may utilize process flow 900, can facilitate intelligent plan selection to lower costs while maintaining appropriate levels of treatment as described herein.

At 905, patient 170 may initiate the transmission of one or more of: patient recurring treatment information (e.g. drugs/devices that are being used by patient 170 on an ongoing/recurring basis) and/or coverage related information 272. For example, patient 170 may indicate (e.g. using an application on the mobile computing device) that stored coverage related information 272 and stored prescription information related to some (e.g. selected by patient 170) or all prescriptions be sent to an entity such as PMDP 130 and/or (e.g. stored either locally on the device and/or in the cloud, and/or stored by an entity). As one example, a patient application, which may track and store patient prescriptions and coverage information may send or initiate the sending of local or cloud-based coverage and prescription information to PMDP 130 upon authorization by patient 170. In some embodiments, the application, which may take the form of a health management application, may include one or more other functionalities: such as tracking patient prescriptions, indicate when premium payments/renewals are due, make payments, indicate when a prescribed treatment is to be taken, provide reminders for refills, automatically reorder prescriptions/refills, track costs, schedule and provide reminders for appointments, etc. When an application sends coverage related information 272 and prescription information to PMDP 130, events 910 and 915 may not occur.

In some embodiments, the transmission of coverage related information 272 and/or recurring treatment information may also be initiated by providing an authorization (e.g. to Payer 140 and/or PBM 150 and/or to one or more entities that may store patient health related information) to send prescription data to PMDP 130. In instances, when an authorization is provided and coverage related information 272 and/or recurring treatment information is provided by one or more external entities (such as Payer 140 and/or PBM 150), then, at 910, PMDP 130 may transmit a HTR request with the patient authorization to obtain coverage related information 272 and/or recurring treatment information to one or more Payer(s) 140-$v$ ($1 \leq v \leq V$) and/or PBMs 150-$u$. ($1 \leq u \leq U$). At 915, Payer(s) 140-$v$ ($1 \leq v \leq V$) and/or PBMs 150-$u$. ($1 \leq u \leq U$) may respond (e.g. to PMDP 130) with the requested information pertaining to patient 170.

In block 920, PMDP 130 may determine recurring treatment being used by the patient. The term recurring treatment is used to refer to medications, devices, and/or treatments that have been prescribed to a patient for a medical condition that is likely to occur or will be present over an extended time (e.g. several days, weeks, or months) during the period of coverage. Recurring treatment differs from one time treatment (e.g. for an isolated medical condition such as a one-time/brief antibiotic regimen to cure an opportunistic/difficult to predict infection). In some embodiments, information in HTR sub-blocks may be analyzed to determine recurring patient treatments (e.g. via treatment code(s) 245, prescribed drugs/devices 255-$p$, doses 260-$p$, and durations 265-$p$) contained in the HTR sub-blocks. In instances, where patient treatment information is available (e.g. via the application used by patient 170), the patient treatment may be provided by the application and PMDP 130 may determine recurring patient treatments (e.g. in step 920) based on the provided information.

In some embodiments, at 925 PMDP 130 may send a request for available plan information to Health Exchange (HEX) 180. HEX 180 may be any entity that offers plans for consumer subscription. For example, HEX 180 may be a government authorized entity that offers plans under the Affordable Care Act (ACA), or a department of or contractor affiliated with a private employer that offers multiple plans to employees for selection/enrollment (e.g. during an open enrollment period). The request for plan information may not include PII information pertaining to patient 170 and may specify the type of information requested. In some embodiments, request for plan information may request a list of payers 140-$v$ and PBMs 150-$u$ offering plans in a location specified by patient 170, and plan identification (e.g. Plan ID and/or Group ID) for each offered plan. In some instances, where the list of payers 140-$v$ and PBMs 150-$u$ and plan identification information is publicly available (e.g. via published information) then, the published information may be accessed by PMDP 130 to obtain the information without the PMDP 130 request (at 925) and HEX 180 response (at 930).

In some embodiments, at 930, HEX 180 may respond with a list of payers 140-$v$ and PBMs 150-$u$ offering plans in a location specified by patient 170, and plan identification (e.g. Plan ID and/or Group ID) for each offered plan (or, alternatively, the above information may be determined by PMDP 130 using publicly available information as outlined above).

In some embodiments, in step 933, PMDP 130 may determine, for each recurring treatment (drug, device and/or procedure) 255-$r$ associated with patient 170, a treatment class 337-$r$, and treatment class members 302-$rd$, where $1 \leq d \leq D\_r$, where $D\_r$ is the number of class members in treatment class 337-$r$. Drugs/devices 302-$rd$ in a treatment class 337-$r$ may: (a) treat a similar therapeutic area 360-$r$, and/or (b) have similar modes/methods of action 340-$r$, and/or (c) have similar chemical structure 350-$r$. In addition, drugs/devices 302-$rd$ in a treatment class 337-$r$ may also share routes of administration 335-$rd$ and meet other patient criteria 297. For medical procedures, members 302-$rd$ of a treatment class 337-$r$ may: (a) treat a similar indication and/or (b) specify alternate facilities (e.g. in some location) where the same/similar treatment may be obtained (although potentially at a different price point).

In step 935 PMDP 130 may send DIR sub-block (e.g. DIR sub-block 380 including treatment code 245 and/or other information in block 280) along with plan identification information (e.g. Plan ID and/or Group ID) to one or more PBMs 150-$u$ and/or Payers 140-$v$ as part of a request for pricing and coverage information (e.g. whether the treatment is covered by the corresponding plan (e.g. available to patient 170).

At 940, in some embodiments, PBMs 150-$u$ and/or Payers 140-$v$ may respond with formulary information for each plan (e.g. as in sub-block 480) and/or authorized providers (e.g. for a procedure).

Alternatively, in some embodiments. when formulary information for each plan (e.g. as in sub-block 480) and/or authorized providers (e.g. for a procedure) are publicly available (and/or available through HEX 180), then, the publicly available information may be used and/or the information obtained from HEX 180. For example, regulations may require plans (payers 140 and/or PBMs 150) to publish and update formulary and other coverage information, so, the most recent published information or update may be used to determine formulary information for each plan (e.g. as in sub-block 480) and/or authorized providers (e.g. for a procedure). Accordingly, in some embodiments, events 935 and 940 may not form part of process flow 900 and PMDP 130 may determine formulary information for each plan (e.g. as in sub-block 480) and/or authorized providers (e.g. for a procedure) as part of step 933, as a separate intermediate step between step 933 and 945, and/or as part of step 945.

In some embodiments, in step 945, PMDP 130 may determine overall patient-specific cost information associated with each plan. For example, a cost C_hs may be assigned to each plan h and based on selecting one treatment 302-$rs$ from each treatment class 337-$r$. For example, for a plan h, where the recurring treatments (e.g. determined in step 920) are associated with four treatment classes with one or more treatments in each treatment class 337-$r$, then, one treatment 302-$rs$ from each of the four treatment classes may be selected to determine a patient specific cost C_hs associated with the plan and selected treatments. As one example, $$C\_hs = (\text{Premia over period}) + (\text{Copayments}) + (\text{Coinsurance}) + (\text{Deductibles}) - (\text{Payment Assistance over period})$$

In some embodiments, a patient specific cost C_hs may be provided for various selections of treatments in each plan h. Thus, patient 170 and/or HCP 120 may be able to determine, prior to plan selection, a potential or likely cost associated with the plan. The payment assistance may be provided by PMDPs 130 and/or by other entities (e.g. by the government toward insurance premiums under the ACA, or by a non-profit, by an organization/program affiliated with PMDP 130, and/or by tax rebates, etc.).

In some embodiments, the information may be provided in the form of a table (or database) as shown in Table 1 below. The table may comprise information about a Plan h, Selected Treatment Set (s), Cost C_hs, and Providers for each selected treatment 302-$rs$ (e.g. pharmacy, location, etc.). In some embodiments, Cost C_hs may further include a cost breakdown (copayment, coinsurance, etc.) for each selected treatment 302-$rs$ in a treatment set.

TABLE 1

| Plan h | Treatment Set (s) | Cost C_hs | Providers |
|---|---|---|---|
| H1 (h = 1) | s = 1 | C_11 | |
| | x | | A |
| | y | | B |
| | z | | C |
| | w | | D |
| H1 (h = 1) | s = 2 . . . | C_12 | . . . |
| H2 (h = 2) | s = 1 . . . | C_21 | . . . |
| . . . | . . . | . . . | . . . |

In some embodiments, at 950, cost information C_hs and other cost metrics may be sent to patient 170 either directly or indirectly (e.g. via HEX 180, as shown by the dashed lines). In some embodiments, patient 170 may authorize PMDP 130 to share the treatment and cost information be shared with HCP 120 and/or patient 170 may optionally share and discuss the treatment information with HCP 120.

At 955, HCP 120 may recommend one of the treatment sets as appropriate and patient 170 may make a plan selection (e.g. by selecting the plan shown on a mobile device screen) and confirming the selection. The plan selected by patient 170 may be the same as the one recommended by HCP 120 and/or any other available plan. Upon confirmation, at 955, the plan selection may be sent to HEX 180.

At 960, upon approval by Payer 140 and/or PBM 150, the platform (e.g. private permissioned blockchain platform) may indicate transaction confirmation to entities associated with the transaction. Upon receiving the confirmation each entity may add its respective encrypted record (e.g. PBR for PBM 140, HTR for Payer 140 and a corresponding HEX record (not shown in FIG. 9)) to a local blockchain. In some embodiments, when authorized, transaction confirmation may also be sent to PMDP 130 to facilitate participation and payment of benefits from a payment assistance program. In some embodiments, at 960, the platform (e.g. private permissioned blockchain platform) may indicate transaction confirmation by sending a plan subscription confirmation to patient 170. In addition, two or more of the above encrypted records may form part of a multi-dimensional block 965 thereby augmenting a multi-dimensional blockchain.

Figure 10B:
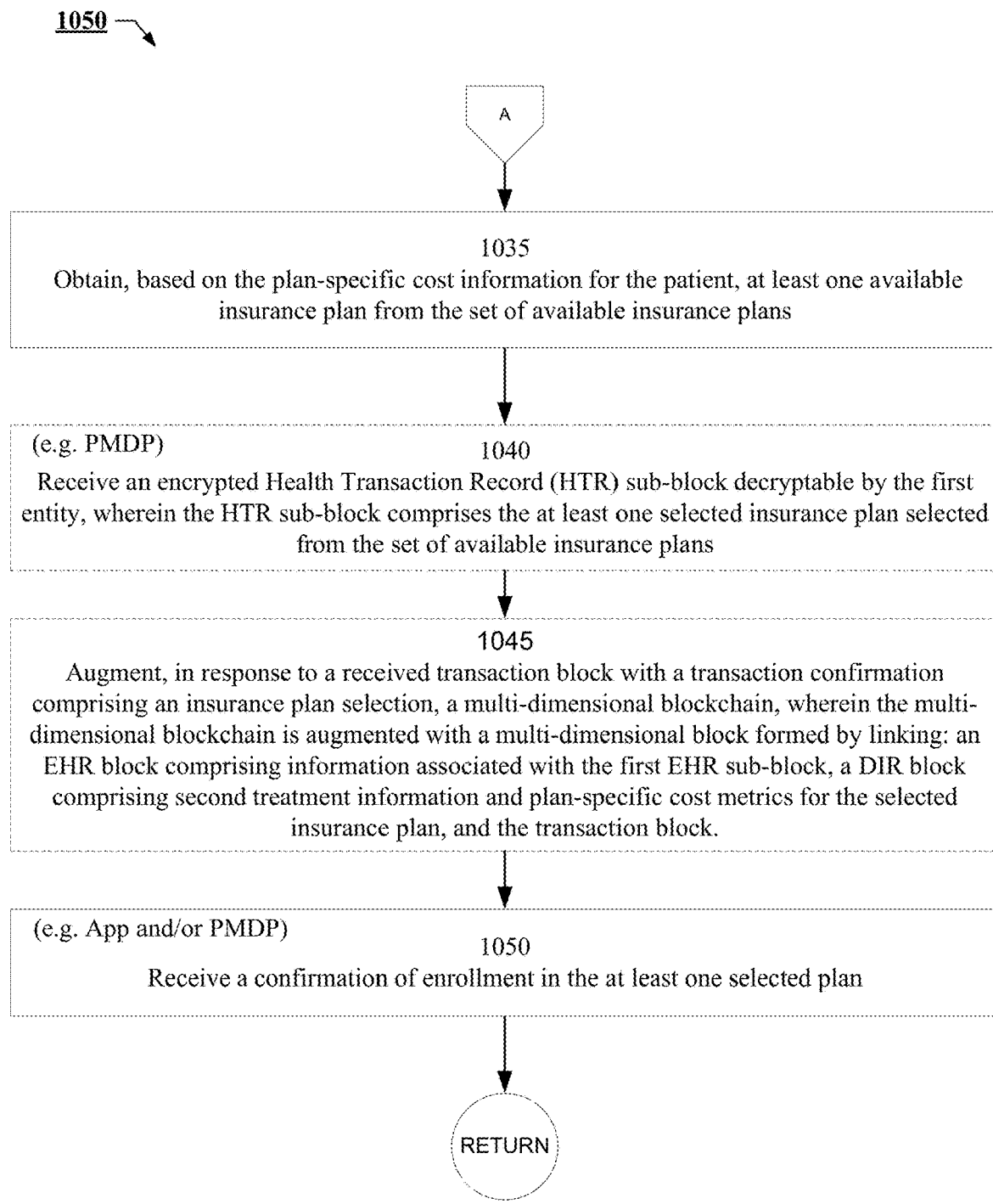

FIGS. 10A and 10B show a flowchart of an exemplary method 1000 to facilitate healthcare insurance selection and cost determination, while maintaining healthcare information security and facilitate interoperability between a plurality of entities. In some embodiments, method 1000 may use multi-dimensional blockchains, which may be based on distinct blockchains maintained by the individual entities in a system. In some embodiments, method 1000 may be performed (at least in part) on a private permissioned blockchain platform, which, in some instances, may take the form of a cloud-based system. Method 1000 may also be performed by a processor, computer or networks of computers such as distributed computing systems, servers (hardware and software), including application servers, mobile computing devices (e.g. smartphones, smart wearable devices, handheld computers, tablets, laptops, etc.), as well as cloud-based systems.

In some embodiments, method 1000 may be performed at a first entity. For example, the first entity may comprise at least one server or a computer system associated with at least one of a pharmaceutical provider such as PMDP 130 and/or an application (e.g. provided by PMDP 130 or another entity) used by a patient (that may interact and utilize functionality provided by the permissioned blockchain platform when authorized on behalf of PMDP 130 and/or the other entity). In some embodiments, the first entity may interact with one or more second entities. The second entities may include one or more servers or computer systems associated with healthcare exchanges such as HEX 180, pharmacy benefit managers such as PBMs 150-$u$, insurance providers such as Payers 140-$v$, or patients 170. In some embodiments, the first entity and the one or more second entities may form computing nodes in a distributed computing system and the multi-dimensional blockchain may form part of a permissioned private blockchain platform.

In some embodiments, method 1000 may be invoked when an entity such as the first entity initiates a transaction (e.g. with a transaction ID and/or transaction type) to add a block to locally maintained blockchain. The addition of the block to the local blockchain may involve inputs from one or more other entities and the permissioned private blockchain platform may invoke method 1000.

Referring to FIG. 10A, in step 1010, a first entity (e.g. PMDP 130 and/or an application running a patient computing device such as a smartphone and/or another entity) may obtain from at least one encrypted first Health Transaction Record (HTR) sub-block (e.g. sub-block 280 and/or other treatment related information in HTR 600) decryptable by the first entity. In some embodiments, the HTR sub-block may be received in response to a request comprising a patient authorization. The first entity may obtain (e.g. based on information in the at least one first HTR sub-block) a first set of first treatments for the patient over a time period, wherein each first treatment comprises a first diagnosis code (e.g. diagnosis code 240) and a first treatment code (e.g. treatment code 245). In some embodiments, the first EHR sub-blocks may include treatment code(s) 245, prescribed drugs/devices 255-$p$, doses 260-$p$, and durations 265-$p$ associated with the first (recurring) treatments 255-$p$. In some embodiments, the time period may include several prior coverage periods and include multiple Payers 140-$v$, which may facilitate determination of recurrent and ongoing treatments.

In some embodiments, the first set of first treatments may be determined based on one or more of: treatment code(s) 245-$p$, prescribed drugs/devices 255-$p$, doses 260-$p$, and durations 265-$p$ contained in the HTR sub-blocks. The first treatments may comprise recurring treatments such as drugs, devices, and/or procedures 255-$p$ that may have been prescribed and/or are likely to be prescribed over the specified time period. In some embodiments, information in the at least one first HTR sub-block (e.g. received by the first entity) may be analyzed (e.g. mathematically and/or statistically) to determine the first set of first treatments (e.g. recurring patient treatments). For example, a monthly prescription may be projected as continuing until the end of the specified time period (e.g. based on duration 265-$p$, a determined or projected frequency). In some embodiments, projections and/or determined recurring treatments may be subject to patient confirmation. In some embodiments, locally stored data (e.g. as part of a health management application) may be used to obtain the first set of first treatments.

In some embodiments, treatments associated with certain medical conditions (e.g. discernible via diagnosis code 240) known to be chronic or long lasting may be automatically identified as recurring treatments. In other instances, treatments that occur repeatedly over the time period may be determined to be recurring treatments. As another example, a treatment may be determined to be recurring based, in part, on additional information such as a patient's calendar (e.g. as part of a health management application) indicating a pattern of scheduled appointments for a specific diagnosis code with a provider. In instances, where an application (e.g. health management or other application) stores patient treatment and/or appointment information, the recurring patient treatment information may be determined based on the stored patient treatment and/or appointment information. The first set of first treatments may be obtained from HTRs 600 maintained by Payer 140 and/or PBRs 400 PBM 150, which may include records for treatments over a long period. In some embodiments, a plurality of Payers 140-$v$ and/or PBMs 150-$u$ used by the patient (e.g. over some specified prior period) may be contacted to obtain information in the first HTR sub-block(s).

In some embodiments, in step 1015, the first entity (e.g. PMDP 130) may determine, based on the first set: (a) one or more second sets, wherein each second set comprises corresponding second treatments, wherein each corresponding second treatment is associated with: a distinct first treatment in the first set, and (b) a corresponding number of recurrences (e.g. over the specified time period such as the intended duration of coverage). The number of recurrences may be used to determine cost (e.g. by multiplying the cost per treatment with a pro-rated or normalized number of recurrences over a time period). In some embodiments, an application (e.g. running a patient computing device such as a smartphone) may obtain the one or more second sets, corresponding second treatments, and recurrences corresponding to each second treatment, from PMDP 130 (e.g. via a secure API).

As one example, each first treatment (255-$p$) in the set of first treatments may be associated with a corresponding first treatment class (337-$p$). Each treatment class (337-$p$) may comprise a one or more treatment class members (302-$pd$, $1 \le d \le D\_p$). Each second set may comprise corresponding second treatments (302-$pd$) associated with a distinct first treatment (255-$p$) via the first treatment class (337-$p$). Thus, as one example, the corresponding second set may comprise one treatment class member (302-$pd$) from each treatment class (337-$p$) (that corresponds to a first treatment 255-$p$). Step 1015 may be viewed as expanding a set of currently prescribed recurring treatments for patient 170 to similar classes of available treatments.

In step 1020, a set of available insurance plans (e.g. Plan ID, Group ID, etc.) available to the patient and corresponding coverage related information (e.g. premiums, deductibles, copayments, coinsurance, formulary information, etc.) for each available insurance plan may be obtained (e.g. by PMDP 130 and/or an application running a patient computing device such as a smartphone). The available insurance plans and coverage related information may be obtained from HEX 180, and/or Payers 140-*v*, and/or PBMs 150-*u*, and/or an employer (e.g. when the plans are employer sponsored) and/or from publicly available information (e.g. by published information available from government or other public sources). The set of available insurance plans and corresponding coverage related information may be obtained based on non-personal information (e.g. without providing patient PII) associated with the patient such as location (country, state, county, city, zip code), age, etc. In some embodiments, an application (e.g. running a patient computing device such as a smartphone) may obtain the set of available insurance plans and corresponding coverage related information by using published information and/or from PMDP 130 (e.g. via an API).

In step 1025, for one or more available insurance plans, corresponding plan-specific cost information for the patient may be determined based on: (a) the one or more sets of second treatments, and (b) corresponding coverage related information. In some embodiments, the corresponding plan-specific cost information for the patient may reflect applicable payment assistance each second set. For example, for available plans, plan-specific cost information may be determined for patient 170 based on the recurring treatments in each second set. In some embodiments, the cost information may be ranked (e.g. from highest projected cost to lowest projected cost). In some embodiments, step 1015 may be skipped, and, in block 1025, plan-specific cost information may be determined for the patient based on the first set of first treatments thereby providing plan-specific cost estimates for existing treatments used by the patient. In some embodiments, an application (e.g. on a smartphone or other mobile computing device associated with patient 170) may determine the plan specific cost information and provide a list of plan options, which may be ranked by cost or other patient criteria 297 to patient 170. In some embodiments, the plan specific cost information for the patient may be received by the application from PMDP 130 (e.g. via a secure API).

In some embodiments, optionally in step 1030, when determined by PMDP 130, the plan specific cost information may optionally be transmitted (e.g. by PMDP 130 in a DIR sub-block comprising information in DIR sub-block 380 and 390 and/or other information in DIR record 300) to a second entity (e.g. to an HCP 120 authorized by the patient 170). In some embodiments, plan specific cost information (e.g. in the DIR sub-blocks) may also be provided to an application (e.g. on a smartphone or other mobile computing device associated with patient 170) via a secure API.

For example, the cost information may include aggregate cost metrics 395-*p* (e.g. aggregate plan specific cost information associated with treatments 302-*pr* in the corresponding second set). For example, (as shown in Table 1), DIR sub-blocks (e.g. 380 and/or 390) may comprise information about a Plan h, Selected Treatment Set (s), Cost C_hs, and Providers for each selected treatment 302-*rs* (e.g. pharmacy, location, etc.) in the corresponding second set. In some embodiments, Cost C_hs may further include a cost breakdown (copayment, coinsurance, etc.) for each selected treatment 302-*rs* in a treatment set. In some embodiments, an application (e.g. on a smartphone or other mobile computing device associated with patient 170) may determine the plan specific cost information and provide a list of plan options, which may be ranked by cost or other patient criteria 297 to patient 170.

Referring to FIG. 10B, in step 1035, based on the plan-specific cost information for the patient, at least one available insurance plan from the set of available insurance plans may be obtained. For example, a patient may select at least one available insurance plan from the set of available insurance plans. As another example, PMDP 130 may receive the at least one selected available insurance plan from an application (e.g. on a smartphone or other mobile computing device associated with patient 170) via a secure API.

In optional step 1040, PMDP 130 may further receive a second encrypted Health Transaction Record (HTR) sub-block decryptable by PMDP 130, wherein the HTR sub-block comprises the selected insurance plan selected from the set of available insurance plans.

In optional step 1045 (which may be performed when PMDP 130 receives HTR sub-blocks in step 1040 and/or is deemed to be a party to the transaction), then PMDP 130 may augment a multi-dimensional blockchain with a multi-dimensional block formed by linking: an HTR block comprising information associated with the second HTR sub-block and a DIR block comprising second treatment information, plan-specific cost metrics for the selected insurance plan, and the transaction block. In some embodiments, the multi-dimensional blockchain may be augmented in response to a received transaction block (e.g. from HEX 180 and/or Payer 140 and/or PBM 150) with a transaction confirmation comprising an insurance plan selection.

In block 1050, the application (e.g. on a smartphone or other mobile computing device associated with patient 170) may receive a confirmation of enrollment in the at least one selected plan (e.g. via a secure message from HEX 180, and/or Payer 140 and/or PBM 150 and/or from PMDP 130 via a secure API).

Figure 11:
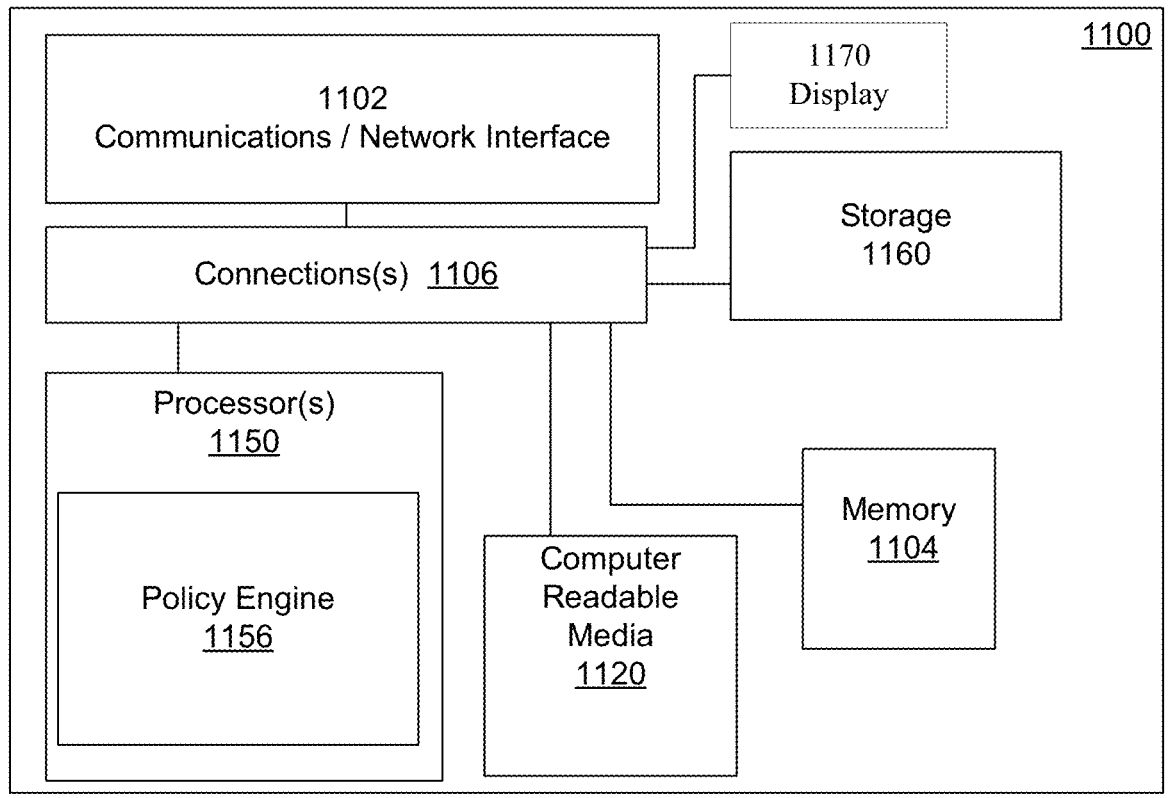
FIG. 11 shows a schematic of an exemplary computer or computing device capable of facilitating healthcare system security and promoting interoperability.

FIG. 11 shows a schematic of an exemplary computer 1100 or computing device capable of facilitating healthcare system security and promoting interoperability. In some embodiments, computer 1100 may host and/or interact with a permissioned private blockchain platform. Computer 110 may be a computing device associated with an entity (e.g. HCP 120, PMDP 130, Payer 140, PBM 150, Pharmacy 160, and/or HEX 180) and/or patient 170 and/or may be used to implement the permissioned blockchain platform. Computer 130 is merely an example, and several computers may be used in a networked and/or distributed fashion to implement methods and process flows disclosed herein.

In some embodiments, exemplary computer 1100 may be include (physical) servers or run servers (e.g. application servers) for one or more entities (such as HCP 120, PMDP 130, Payer 140, PBM 150, Pharmacy 160, and/or HEX 180). In some embodiments, one computer 1100 may implement some or all of the process flows and/or methods and/or other techniques disclosed herein including those in FIGS. 7-10. In some embodiments, computer 1100 may form part of a distributed computing system, which may implement the permissioned private blockchain platform. In some embodiments, the distributed computing system and/or computer 1100 may be cloud-based. In some embodiments, computer 1100 may be a mobile computing device such as a smartphone, tablet, handheld, notebook, and/or laptop, which may run applications to interact with other computers 1100 and/or other applications to implement techniques disclosed herein.

In some embodiments, computer 1100/processor(s) 1150 may be able to process transaction requests, including requests related to the addition of blocks to a blockchain, including multi-dimensional blockchains. Further, computer 1100/processor(s) 1150 may be able to run encryption and/or decryption algorithms, obtain hashes of information blocks, verify hashes, perform digital signing, and may be capable of executing and/or support various methods to promote security and authentication. Authentication may refer to both the verification of the integrity of stored information (e.g. in a block in a blockchain to determine any unauthorized alterations) and ensuring that entities accessing the permissioned private blockchain platform are trustworthy and have permissions to perform any requested transactions. In some embodiments, computer 1100/processor(s) 1150 may also augment (create or add to) blockchains with new blocks (including augmenting multi-dimensional blockchains with multi-dimensional blocks).

In some embodiments, computer 1100/processor(s) 1150 may also store and execute smart contracts associated with blockchains to implement agreements related to privacy, information sharing, contractual execution, etc. between entities (e.g. HCP 120, PMDP 130, Payer 140, and/or patient(s)).

In some embodiments, computer 1100/processor(s) 1150 may be capable of mathematically analyzing and statistically compiling health related data including determining treatment classes (e.g. drug classes, device classes, and/or procedural classes) associated with a treatment, determining cost metrics, individually, and in the aggregate, associated with treatments from the treatment classes and using patient criteria to filter and/or narrow selections. In some embodiments, computer 1100/processor(s) 1150 may also be able to initiate the display (e.g. on display 1170) of the information on a smartphone (e.g. using a Graphical User Interface (GUI). Computer 1100/processor(s) 1150 may also be capable of using machine learning techniques to determine relationships between various health parameters. For example, computer 1100/processor(s) 1150 may comprise one or more neural network processor(s), and/or distributed processors capable of being configured as a neural network, and/or be capable of executing software to model and/or simulate neural networks, which may be used to implement machine learning. For example, a PMDP 130 may use machine learning techniques based RWE information available through the multi-dimensional blocks (e.g. demographic information, side effects, drugs used in combination with a specified drug of interest, treatment outcomes etc.) to tailor usage of drug. For example, machine learning may be used to determine an effective dosage, target drugs based on demographics, improve drug interaction information, increase safety, determine the relative efficacy of various modes of administration, etc.

In some embodiments, computer 1100 may be coupled to other computers using communications/network interface 1102, which may include wired (e.g. Ethernet including Gigabit Ethernet) and wireless interfaces. Wireless interfaces may be based on: Wireless Wide Area Network (WWAN) standards such as cellular standards including 3G, 4G, and 5G standards; IEEE 802.11x standards popularly known as Wi-Fi. and/or Wireless Personal Area Networks (e.g. Bluetooth, Near Field Communication (NFC), etc.). In some embodiments, computer 110 may include Global Positioning System and/or location determination units to automatically determine location (e.g. of a patient), which may be used in conjunction with the techniques disclosed in FIGS. 7-10.

Computer 1100 may include memory 1104, which may include one or more of: Read Only Memory (ROM), Programmable Read Only Memory (PROM), Random Access Memory (RAM) of various types, Non-Volatile RAM, etc. Memory 1104 may be implemented within processor(s) 1150 or external to processor(s) 1150. As used herein, the term "memory" refers to any type of long term, short term, volatile, nonvolatile, or other memory and is not to be limited to any particular type of memory or number of memories, or type of media upon which memory is stored.

Memory may comprise cache memory, primary memory, and secondary memory. Secondary memory may include computer-readable media 1120. Computer-readable media may include magnetic and/or optical media, which, in some instances, may be removable media. Removable media may comprise optical disks such as compact-discs (CDs), laser discs, digital video discs (DVDs), blu-ray discs, and other optical media and further include USB drives, flash drives, solid state drives, memory cards etc. Computer 1100 may further include storage 1160, which may include hard drives, solid state drives (SSDs), flash memory, other non-volatile storage, and cloud-based storage.

Communications/Network interface 1102, storage 1160, memory 1104, and computer readable media 1120 may be coupled to processor(s) 1150 using connections 1106, which may take the form of a buses, lines, fibers, links, etc.

The methodologies described herein may be implemented by various means depending upon the application. For example, these methodologies may be implemented in hardware, firmware, software, or any combination thereof. For a hardware implementation, the processor(s) 1150 may be implemented within one or more application specific integrated circuits (ASICs), digital signal processors (DSPs), neural network processors (NNPs), digital signal processing devices (DSPDs), programmable logic devices (PLDs), field programmable gate arrays (FPGAs), processors, controllers, micro-controllers, microprocessors, electronic devices, other electronic units designed to perform the functions described herein, or a combination thereof.

For a firmware and/or software implementation, the methodologies may be implemented with microcode, procedures, functions, and so on that perform the functions described herein. Any machine-readable medium tangibly embodying instructions may be used in implementing the methodologies described herein. For example, software may be stored in storage 1160 and/or on removable computer-readable media. Program code may be resident on computer readable media 1120, storage 1160, and/or memory 1104 and may be read and executed by processor(s) 1150.

If implemented in firmware and/or software, the functions may also be stored as one or more instructions or code computer-readable medium 1120, storage 1160, and/or memory 1104. Examples include computer-readable media encoded with data structures and computer programs. For example, computer-readable medium 1120 may include program code stored thereon may include program code to support methods to facilitate healthcare system security and promote system interoperability, including by supporting multi-dimensional blockchains, smart contracts, consensus determination and performing other function associated with a permissioned private blockchain platform as described herein.

Processor(s) 1150 may be implemented using a combination of hardware, firmware, and software. In some embodiments, computer 1100 may be coupled to a display to facilitate viewing of GUIs and interaction with administrators and other users.

Although the present disclosure is described in connection with specific embodiments for instructional purposes, the disclosure is not limited thereto. Various adaptations and modifications may be made to the disclosure without departing from the scope. Therefore, the spirit and scope of the appended claims should not be limited to the foregoing description.

What is claimed is:

1. A processor-implemented method at a first entity comprising:
   receiving at least one encrypted first Electronic Health Record (EHR) sub-block decryptable by the first entity, wherein the at least one EHR sub-block comprises patient medical coverage information for a patient and one or more first treatments;
   transmitting, in response to the first EHR sub-block, at least one encrypted first Device Drug Information (DIR) sub-block decryptable by at least one corresponding second entity, wherein the at least one first DIR sub-block comprises, for each of the one or more first treatments, a corresponding first treatment class, one or more corresponding first treatment class members associated with each corresponding first treatment class, and for each first treatment class member, corresponding first treatment class member cost information;
   receiving, in response to the first DIR sub-block, an encrypted second EHR sub-block decryptable by the first entity, wherein the second EHR sub-block comprises one or more second treatments, wherein each of the one or more second treatments is associated with a corresponding first treatment and each second treatment is selected from the corresponding first treatment class members associated with the corresponding first treatment; and
   augmenting, in response to a transaction confirmation, a multi-dimensional blockchain, wherein the multi-dimensional blockchain is augmented with a multi-dimensional block formed by linking: a DIR block comprising information associated with the one or more second treatments, an EHR block comprising information associated with the second EHR sub-block, and a transaction block.

2. The processor-implemented method of claim 1, wherein, upon receiving the first EHR sub-block, the method further comprises:
   determining, for each of the one or more first treatments, the corresponding first treatment class, wherein each corresponding first treatment class comprises the one or more corresponding first treatment class members; and
   determining, for each corresponding first treatment class, the one or more corresponding first treatment class member cost information.

3. The processor-implemented method of claim 2, further comprising:
   determining, based on the corresponding first treatment class member cost information for each first treatment class, aggregate cost metrics based on at least one of: the one or more first treatments, or the one or more second treatments, or a combination thereof.

4. The processor-implemented method of claim 1, wherein the first EHR sub-block comprises patient-specific parameters and the at least one treatment class is determined based on the patient-specific parameters.

5. The processor-implemented method of claim 4, wherein the patient-specific parameters comprise patient co-morbidity information.

6. The processor-implemented method of claim 4, wherein the patient-specific parameters comprise route of administration information.

7. The processor-implemented method of claim 4, wherein the patient-specific parameters comprise safety and efficacy information.

8. The processor-implemented method of claim 4, wherein the patient-specific parameters comprise patient location information.

9. The processor-implemented method of claim 1, wherein, for each first treatment, the corresponding first treatment class and the one or more corresponding first treatment class member cost information for each treatment class member are determined based on the patient medical coverage information.

10. The processor-implemented method of claim 9, wherein the one or more corresponding first treatment class member cost information is determined based further on providers located within a specified distance of a patient location, wherein location information for the patient is comprised in the first EHR sub-block.

11. The processor-implemented method of claim 1, wherein the one or more corresponding first treatment class member cost information includes one or more of:
   a patient specific out-of-pocket cost corresponding to each corresponding first treatment class member for a corresponding treatment unit; or
   a patient-specific estimated total out-of-pocket cost corresponding to each corresponding first treatment class member for a typical treatment duration; or
   a patient-specific estimated total out-of-pocket cost corresponding to each corresponding first treatment class member for the remaining duration of a medical coverage plan associated with the patient.

12. The processor-implemented method of claim 1, wherein, upon receiving the second EHR sub-block, the method further comprises:
   determining payment assistance information for at least one of the one or more second treatments; and
   transmitting the payment assistance information with a transaction confirmation to a patient.

13. The processor-implemented method of claim 1, further comprising:
   transmitting a transaction confirmation comprising at least one prescription for the one or more second treatments along with payment assistance information to the patient.

14. A computing device for a first entity comprising:
   a memory,
   a communications interface, and
   a processor coupled to the memory and the communications interface, wherein the processor is configured to:
   receive at least one encrypted first Electronic Health Record (EHR) sub-block decryptable by the first entity, wherein the at least one EHR sub-block comprises patient medical coverage information for a patient and one or more first treatments;
   transmit, in response to the first EHR sub-block, at least one encrypted first Device Drug Information (DIR) sub-block decryptable by at least one corresponding second entity, wherein the at least one first DIR sub-block comprises, for each of the one or more first treatments, a corresponding first treatment class, one or more corresponding first treatment class members associated with each corresponding first treatment class, and for each first treatment class member, corresponding first treatment class member cost information;
   receive, in response to the first DIR sub-block, an encrypted second EHR sub-block decryptable by the first entity, wherein the second EHR sub-block comprises one or more second treatments, wherein each of the one or more second treatments is associated with a corresponding first treatment and each second treatment is selected from the corresponding first treatment class members associated with the corresponding first treatment; and augment, in response to a transaction confirmation, a multi-dimensional blockchain, wherein the multi-dimensional blockchain is augmented with a multi-dimensional block formed by linking: a DIR block comprising information associated with the one or more second treatments, an EHR block comprising information associated with the second EHR sub-block, and a transaction block.

15. The computing device of claim 14, wherein, upon receiving the first EHR sub-block, the method further comprises:

determine, for each of the one or more first treatments, the corresponding first treatment class, wherein each corresponding first treatment class comprises the one or more corresponding first treatment class members; and determine, for each corresponding first treatment class, the one or more corresponding first treatment class member cost information.

16. The computing device of claim 15, further comprising:

determine, based on the corresponding first treatment class member cost information for each first treatment class, aggregate cost metrics based on at least one of: the one or more first treatments, or the one or more second treatments, or a combination thereof.

17. The computing device of claim 14, wherein the first EHR sub-block comprises patient-specific parameters and the at least one treatment class is determined based on the patient-specific parameters.

18. The computing device of claim 14, wherein the one or more corresponding first treatment class member cost information includes one or more of:

a patient specific out-of-pocket cost corresponding to each corresponding first treatment class member for a corresponding treatment unit; or a patient-specific estimated total out-of-pocket cost corresponding to each corresponding first treatment class member for a typical treatment duration; or a patient-specific estimated total out-of-pocket cost corresponding to each corresponding first treatment class member for the remaining duration of a medical coverage plan associated with the patient.

19. The computing device of claim 14, wherein, upon receiving the second EHR sub-block, the method further comprises:

determine payment assistance information for at least one of the one or more second treatments; and transmit the payment assistance information with a transaction confirmation to a patient.

20. A non-transitory computer-readable medium comprising executable instructions to configure a processor to:

receive at least one encrypted first Electronic Health Record (EHR) sub-block decryptable by the first entity, wherein the at least one EHR sub-block comprises patient medical coverage information for a patient and one or more first treatments;

transmit, in response to the first EHR sub-block, at least one encrypted first Device Drug Information (DIR) sub-block decryptable by at least one corresponding second entity, wherein the at least one first DIR sub-block comprises, for each of the one or more first treatments, a corresponding first treatment class, one or more corresponding first treatment class members associated with each corresponding first treatment class, and for each first treatment class member, corresponding first treatment class member cost information;

receive, in response to the first DIR sub-block, an encrypted second EHR sub-block decryptable by the first entity, wherein the second EHR sub-block comprises one or more second treatments, wherein each of the one or more second treatments is associated with a corresponding first treatment and each second treatment is selected from the corresponding first treatment class members associated with the corresponding first treatment; and augment, in response to a transaction confirmation, a multi-dimensional blockchain, wherein the multi-dimensional blockchain is augmented with a multi-dimensional block formed by linking: a DIR block comprising information associated with the one or more second treatments, an EHR block comprising information associated with the second EHR sub-block, and a transaction block.

* * * * *